United States Patent [19]
Pavlakis et al.

[11] Patent Number: 6,027,881
[45] Date of Patent: Feb. 22, 2000

[54] **MUTANT *AEQUOREA VICTORIA* FLUORESCENT PROTEINS HAVING INCREASED CELLULAR FLUORESCENCE**

[75] Inventors: George N. Pavlakis, Rockville; George A. Gaitanaris, Gaithersburg; Roland H. Stauber, Frederick, all of Md.; John N. Vournakis, Hanover, N.H.

[73] Assignee: The United States of America as represented by the Secretary of the Department of Health and Human Services, Washington, D.C.

[21] Appl. No.: 08/646,538

[22] Filed: May 8, 1996

[51] Int. Cl.[7] .............................. C12Q 1/68; C12N 1/20; C07K 1/00; C07H 21/04
[52] U.S. Cl. ......................... 435/6; 435/69.1; 435/69.7; 435/252.3; 435/320.1; 536/23.4; 536/23.5; 530/350
[58] Field of Search .................................. 435/69.1, 69.7, 435/252.3, 320.1, 189, 172.1, 6; 536/23.4, 23.5; 530/350

[56] References Cited

U.S. PATENT DOCUMENTS

| | | | |
|---|---|---|---|
| 5,625,048 | 4/1997 | Tsien et al. | 536/23.4 |
| 5,804,387 | 9/1998 | Cormack et al. | 435/6 |

FOREIGN PATENT DOCUMENTS

| | | |
|---|---|---|
| WO 95 07463 | 3/1995 | WIPO . |
| WO 95/07463 | 3/1995 | WIPO . |
| WO 96 23810 | 8/1996 | WIPO . |
| WO 97 11094 | 3/1997 | WIPO . |

OTHER PUBLICATIONS

Cormack et al. (Apr. 1996) CLONTECHniques, p. 21.
Htun, H. et al., *Proc. Natl. Acad. Sci. USA*, 93:4845–4850 (1996).
Lewis, P.J. et al., *Microbiology*, 142:733–740 (1996).
Ha, D.S. et al., *Mol. Biochem. Parasitol.*, 77:57–64 (1996).
Stone, K.D. et al., *Mol. Microbiol.*, 20:325–337 (1996).
Chiu, W. et al., *Curr. Biol.*, 6:325–330 (1996).
Heim, R. et al., *Curr. Biol.*, 6:178–182 (1996).
Rizzuto, R. et al., *Curr Biol*, 6:183–188 (1996).
Wolk, C.P., *Annu. Rev. Genet.*, 30:59–78 (1996).
Mitra, R.D. et al., *Gene*, 173 (1 Spec No) :13–17 (1996).
Yang, T.T. et al., *Gene*, 173 (1 Spec No) :19–23 (1996).
Cormack, B.P. et al., *Gene*, 173 (1 Spec No) :33–38 (1996).
Dopf, J. et al., *Gene*, 173 (1 Spec No) :39–44 (1996).
Burlage, R.S. et al., *Gene*, 173 (1 Spec No) :53–58 (1996).
Ropp, J.D. et al., *Cytometry*, 21:309–317 (1995).
Lim, C.R. et al., *J. Biochem.* (Tokyo) 118:13–17 (1995).
Ehrig, T. et al., *FEBS Lett.*, 367:163–166 (1995).
Heim, R. et al., *Proc. Natl. Acad. Sci. USA*, 91:12501–12504 (1994).
Delagrave, S. et al., *Bio/Technology*, 13:151–154 (1995).
Heim, R. et al., *Nature*, 373:663–664 (1995).
Galbraith, D.W. et al., *Methods in Cell Biology*, 50:1–12 (1995).
Kaether, C. et al., *FEBS Lett.*, 369:267 (1995).
Prendergast, F.G. et al., *Biochemistry*, (17) :3448–3453 (1978).
Shimomura, O., *FEBS Lett.*, 104:220–222 (1979).
Ward, W.W. et al., *Photochem. Photobiol.*, 35:803–808 (1982).
Chalfie, M. et al., *Science*, 263:802 (1994).
Cubitt, A.B. et al., *TIBS Elsevier Trends Journals* 448 Nov. (1995).
Kain, S.R. et al., *BioTechniques* 19:650 (1995).
Kitts, P. et al., *CLONTECHniques* X:1 (1995).
Prasher, D.C. et al., *Gene* 111:229 (1992).
Crameri, A. et al., *Nature Biotechnology* 14:315 (1996).
Marshall, J. et al., *Neuron* 14:211 (1995).
Wang, S. et al., *Nature* 369:400 (1994).
Adams, M. et al., Annual Meeting of the American Society for Biochemistry and Molecular Biology, Molecular Cloning: Vectors and Techniques Abstract No. 465 May 21–25 (1995).
Proceedings of the National Academy of Sciences of USA, vol. 91, Dec. 1, 1994, pp. 12501–12504, XP000574454 Heim R et al: "Wavelength Mutations and Posttranslational Autoxidation of Green Fluorescent Protein".
Nature, vol. 373, Feb. 23, 1995, p. 663/664 XP002029558 Heim R et al.: "Improved Green Fluorescence".
Bio/Technology, vol. 13, No. 2, Feb. 1995, pp. 151–154, XP002033686 Delagrave S et al: "Red–Shifted Excitation Mutants of the Green Fluorescent Protein".
FEBS LETTERS, vol. 367, Jan. 1, 1995, pp. 163–166, OX000579119 Ehrig T et al: "Green–Fluorescent Protein Mutants With Altered Fluorence Excitation Spectra".
TIBS Trends in Biochemical Sciences, vol. 20, Nov. 1995, pp. 448–455, XP000606919 Cubitt A B et al: "Understanding, Improving and Using Green Fluorescent Proteins".
Gene, vol. 173, No. 1, Jul. 1, 1996, Elsevier Science Publishers, B.V., Amsterdam, NL; pp. 33–38, XP002037756 B.P. Cormack et al.: "FACS–optimized mutants of the green fluorescent protein (GFP)".

*Primary Examiner*—Ponnathapu Achutamurthy
*Assistant Examiner*—Elizabeth Slobodyansky
*Attorney, Agent, or Firm*—Townsend and Townsend and Crew

[57] ABSTRACT

The present invention is directed to mutants of the jellyfish *Aequorea victoria* green fluorescent protein (GFP) having at least 5 and preferably greater than 20 times the specific green fluorescence of the wild type protein. In other embodiments, the invention comprises mutant blue fluorescent proteins (BFPs) that emit an enhanced blue fluorescence. The invention also encompasses the expression of nucleic acids that encode a mutant GFP or BFP in a wide variety of engineered host cells, and the isolation of engineered proteins having increased fluorescent activity. The novel mutants of the present invention allow for a significantly more sensitive detection of fluorescence in engineered host cells than is possible with GFP or with its known mutants. Thus, the mutant fluorescent proteins provided herein can be used as sensitive reporter molecules to detect the cell and tissue-specific expression and subcellular compartmentalization of GFP or BFP mutants, or of chimeric proteins comprising GFP or BFP mutants fused to a regulatory sequence or to a second protein sequence.

21 Claims, No Drawings

MUTANT *AEQUOREA VICTORIA* FLUORESCENT PROTEINS HAVING INCREASED CELLULAR FLUORESCENCE

FIELD OF THE INVENTION

This invention generally relates to novel proteins and their production which are useful for detecting gene expression and for visualizing the subcellular targeting and distribution of selected proteins and peptides, among other things. The invention specifically relates to mutations in the gene coding for the jellyfish *Aequorea victoria* green fluorescent protein ("GFP"), which mutations encode mutant GFP proteins having either an enhanced green or a blue fluorescence, and uses for them.

BACKGROUND OF THE INVENTION

Green fluorescent protein ("GFP") is a monomeric protein of about 27 kDa which can be isolated from the bioluminescent jellyfish *Aequorea victoria*. When wild type GFP is illuminated by blue or ultraviolet light, it emits a brilliant green fluorescence. Similar to fluorescein isothiocyanate, GFP absorbs ultraviolet and blue light with a maximum absorbance at 395 nm and a minor peak of absorbance at 470 nm, and emits green light with a maximum emission at 509 nm with a minor peak at 540 nm. GFP fluorescence persists even after fixation with formaldehyde, and it is more stable to photobleaching than fluorescein.

The gene for GFP has been isolated and sequenced. Prasher, D. C. et al. (1992), "Primary structure of the *Aequorea victoria* green fluorescent protein," *Gene* 111:229–233. Expression vectors that comprise the GFP gene or cDNA have been introduced into a variety of host cells. These host cells include: Chinese hamster ovary (CHO) cells, human embryonic kidney cells (HEK293), COS-1 monkey cells, myeloma cells, NIH 3T3 mouse fibroblasts, PtK1 cells, BHK cells, PC12 cells, Xenopus, leech, transgenic zebra fish, transgenic mice, Drosophila and several plants. The GFP molecules expressed by these different cells have a similar fluorescence as the native molecules, demonstrating that the GFP fluorescence does not require any species-specific cofactors or substrates. See, e.g., Baulcombe, D. et al. (1995), "Jellyfish green fluorescent protein as a reporter for virus infections," *The Plant Journal* 7:1045–1053; Chalfie, M. et al. (1994), "Green fluorescent protein as a marker for gene expression," *Science* 263:802–805; Inouye, S. & Tsuji, F. (1994), "Aequorea green fluorescent protein: expression of the gene and fluorescent characteristics of the recombinant protein," *FEBS Letters* 341:277–280; Inouye, S. & Tsuji, F. (1994), "Evidence for redox forms of the Aequorea green fluorescent protein," *FEBS Letters* 351:211–214; Kain, S. et al. (1995), "The green fluorescent protein as a reporter of gene expression and protein localization," *BioTechniques* (in press); Kitts, P. et al. (1995), "Green Fluorescent Protein (GFP): A novel reporter for monitoring gene expression in living organisms," *CLONTECHniques* X(1):1–3; Lo, D. et al. (1994), "Neuronal transfection in brain slices using particle-mediated gene transfer," *Neuron* 13:1263–1268; Moss, J. B. & Rosenthal, N. (1994), "Analysis of gene expression patterns in the embryonic mouse myotome with the green fluorescent protein, a new vital marker," *J. Cell. Biochem.*, *Supplement* 18D W161; Niedz, R. et al. (1995), "Green fluorescent protein: an in vivo reporter of plant gene expression," *Plant Cell Reports* 14:403–406; Wu, G.-I. et al. (1995), "Infection of frog neurons with vaccinia virus permits in vivo expression of foreign proteins," *Neuron* 14:681–684; Yu, J. & van den Engh, G. (1995), "Flow-sort and growth of single bacterial cells transformed with cosmid and plasmid vectors that include the gene for green-fluorescent protein as a visible marker," Abstracts of papers presented at the 1995 meeting on "Genome Mapping and Sequencing," Cold Spring Harbor, p. 293.

The active GFP chromophore is a hexapeptide which contains a cyclized Ser-dehydroTyr-gly trimer at positions 65–67. This chromophore is only fluorescent when embedded within the intact GFP protein. Chromophore formation occurs post-translationally; nascent GFP is not fluorescent. The chromophore is thought to be formed by a cyclization reaction and an oxidation step that requires molecular oxygen.

Proteins can be fused to the amino (N-) or carboxy (C-) terminus of GFP. Such fused proteins have been shown to retain the fluorescent properties of GFP and the functional properties of the fusion partner. Bian, J. et al. (1995), "Nuclear localization of HIV-1 matrix protein P17: The use of *A. victoria* GFP in protein tagging and tracing," *FASEB J.* 9:AI279; Flach, J. et al. (1994), "A yeast RNA-binding protein shuttles between the nucleus and the cytoplasm," *Mol. Cell. Biol.* 14:8399–8407; Marshall, J. et al. (1995), "The jellyfish green fluorescent protein: a new tool for studying ion channel expression and function," *Neuron* 14:211–215; Olmsted, J. et al. (1994), "Green Fluorescent Protein (GFP) chimeras as reporters for MAP4 behavior in living cells," *Mol. Biol. of the Cell* 5:167a; Rizzuto, R. et al. (1995), "Chimeric green fluorescent protein as a tool for visualizing subcellular organelles in living cells," *Current Biol.* 5:635–642; Sengupta, P. et al. (1994), "The *C. elegans* gene odr-7 encodes an olfactory-specific member of the nuclear receptor superfamily," *Cell* 79:971–980; Stearns, T. (1995), "The green revolution," *Current Biol.* 5:262–264; Treinin, M. & Chalfie, M. (1995), "A mutated acetylcholine receptor subunit causes neuronal degeneration in *C. elegans,*" *Neuron* 14:871–877; Wang, S. & Hazelrigg, T. (1994), "Implications for bcd MRNA localization from spatial distribution of exu protein in Drosophila oogenesis," *Nature* 369:400–403.

A number of GFP mutants have been reported. Delagrave, S. et al. (1995) "Red-shifted excitation mutants of the green fluorescent protein," *Bio/Technology* 13:151–154; Heim, R. et al. (1994) "Wavelength mutations and posttranslational autoxidation of green fluorescent protein," *Proc. Natl. Acad. Sci. USA* 91:12501–12504; Heim, R. et al. (1995), "Improved green fluorescence," *Nature* 373:663–664. Delgrave et al. (1995) *Bio/Technology* 13:151–154 isolated mutants of cloned *Aequorea victoria* GFP that had red-shifted excitation spectra. Heim, R. et al. (1994) "Wavelength mutations and posttranslational autoxidation of green fluorescent protein," *Proc. Natl. Acad. Sci. USA* 91:12501–12504 reported a mutant (Tyr66 to His) having a blue fluorescence, which is herein designated BFP (Tyr$_{67}$→His). These references have neither taught nor suggested that their mutations resulted in an increase in the cellular fluorescence of the mutant GFPs.

In general, the level of fluorescence of a protein expressed in a cell depends on several factors, such as number of copies made of the fluorescent protein, stability of the protein, efficiency of formation of the chromophore, and interactions with cellular solvents, solutes and structures. Although the fluorescent signal from wild type GFP or from the reported mutants is generally adequate for bulk detection of abundantly expressed GFP or of GFP-containing chimeras, it is inadequate for detecting transient low or constitutively low levels of expression, or for performing fine structural subcellular localizations. This limitation severely restricts the use of native GFP or of the reported mutants as a biochemical and structural marker for gene expression and morphological studies.

SUMMARY OF THE INVENTION

It an object of the invention to provide engineered GFP-encoding nucleic acid sequences that encode modified GFP molecules having a greater cellular fluorescence than modified wild type GFP having SEQ ID NO:2 or previously described recombinant GFP.

It is a further object of this invention to provide recombinant vectors containing these modified GFP-encoding nucleic acid sequences, which vectors are capable of being inserted into a variety of cells (including mammalian and eukaryotic cells) and expressing the modified GFP.

It is also an object of this invention to provide host cells capable of providing useful quantities of homogeneous modified GFP.

It is yet another object of this invention to provide peptides that possess a greater cellular fluorescence than native GFP or unaltered recombinant GFP and that can be produced in large quantities in a laboratory, by a microorganism or by a cell in culture.

These and other objects of the invention have been accomplished by providing mutant GFP-encoding nucleic acids whose gene product exhibits an increased cellular fluorescence relative to naturally occurring or recombinantly produced wild type GFP ("wtGFP"). In some embodiments, the modified GFPs possess fluorescent activity that is 50–100 fold greater than that of unmodified GFP.

The modified proteins of the present invention are produced by making mutations in a genetic sequence that result in alterations in the amino acid sequence of the resulting gene product. Our starting material was a GFP-encoding nucleic acid wherein a codon encoding an additional nucleic acid was inserted at position 2 of the previously published GFP amino acid sequence (Chalfie et al., 1994), to introduce a useful restriction site. Due to the amino acid insertion at position 2 of the GFP amino acid sequence, our numbering of the GFP amino acids and description of the amino acid amutations is off by one as compared to the originally reported wild type GFP sequence (Prasher et al., 1992). Thus, amino acid 65 by our numbering corresponds to amino acid 64 of the originally reported wild type GFP, amino acid 168 corresponds to amino acid 167 of the originally reported wild type GFP, etc.

Using the modified modified wild type GFP having SEQ ID NO:2 described herein, a number of the unique mutants described herein derive from the discovery of an unplanned and unexpected mutation called "SG12", obtained in the course of site-directed mutagenesis experiments, wherein a phenylalanine at position 65 of mwtGFP was converted to leucine. A mutant referred to as "SG11," which combined the phenylalanine 65 to leucine alteration with an isoleucine 168 to threonine substitution and a lysine 239 to asparagine substitution, gave a further enhanced fluorescence intensity. The lysine 239 to asparagine substitution does not affect the fluorescence of GFP; indeed the C-terminal lysine or asparagine may be deleted without affecting fluorescence. A third and further improved GFP mutant was obtained by further mutating "SG11." This mutant is referred to as "SG25" and, in addition to the SG11 mutations, contains an additional mutation, a substitution of a cysteine at position 66 for the serine normally found at that position in the sequence.

In addition, the invention encompasses novel GFP mutants that emit a blue fluorescence. These blue mutants are derived from a mutation of the wild type GFP (Heim, R. et al. (1994) "Wavelength mutations and posttranslational autoxidation of green fluorescent protein," *Proc. Natl. Acad. Sci. USA* 91:12501–12504), in which histidine was substituted for tyrosine at amino acid position 66. This mutant emits a blue fluorescence, i.e., it becomes a Blue Fluorescent Protein (BFP).

Novel BFP mutants having an enhanced blue fluorescence were made by further modifying this BFP(Tyr$_{67}$→His). The introduction of the same mutation used to generate SG12, (i.e., phenylalanine to leucine at position 65) into BFP (Tyr$_{67}$→His) resulted in a new mutant having a brighter fluorescence, designated "SuperBlue-42" (SB42). A second independently generated mutation of BFP(Tyr$_{67}$→His), in which a valine at position 164 was converted to alanine, also emitted an enhanced blue fluorescent signal and is referred to as "SB49." A combination of the above two mutations resulted in "SB50", which exhibited an even greater fluorescence enhancement than either of the previous mutations.

The novel GFP and BFP mutants of this invention allow for a significantly more sensitive detection of fluorescence in host cells than is possible with the wild type protein. Accordingly, the mutant GFPs provided herein can be used, among other things, as sensitive reporter molecules to detect the cell and tissue-specific expression and subcellular compartmentalization of GFP or of chimeric proteins comprising GFP fused to a regulatory sequence or to a second protein sequence. In addition, these mutations make possible a variety of one and two color protein assays to quantitate expression in mammalian cells.

DETAILED DESCRIPTION OF THE INVENTION

The present invention comprises mutant nucleic acids that encode engineered GFPs having a greater cellular fluorescence than either native GFP or unaltered recombinant GFP, and the mutant GFPs themselves. It further comprises a subset of mutant GFPs that are mutant blue fluorescent proteins ("BFPs") that are derived from a published BFP, designated BFP(Tyr$_{67}$→His), wherein the mutant BFPs have a cellular fluorescence that is at least five times greater, preferably ten times greater, and most preferably 20 times greater than that of BFP(Tyr$_{67}$→His). The invention also encompasses compositions such as vectors and cells that comprise either the mutant nucleic acids or the mutant protein gene products. The mutant GFP nucleic acids and proteins may be used to detect and quantify gene expression in living cells, and to detect and quantify tissue specific expression and subcellular distribution of GFP or of GFP fused to other proteins.

I. General Definitions

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

The symbols, abbreviations and definitions used herein are set forth below:

DNA, deoxyribonucleic acid

RNA, ribonucleic acid mRNA, messenger RNA cDNA, complementary DNA (enzymatically synthesized from an mRNA sequence)

A—Adenine
T—Thymine
G—Guanine
C—Cytosine
U—Uracil
GFP, Green Fluorescent Protein
BFP, Blue Fluorescent Protein Amino acids are sometimes referred to herein by the conventional one or three letter codes.

Modified wild type green fluorescent protein ("mwtGFP") refers to the 239 amino acid sequence described by Chalfie et al., *Science* 263, 802–805, 1994, the nucleotide sequence of which is set out as SEQ ID NO:1, and the amino acid sequence of which is set out as SEQ ID NO:2. This sequence differs from the original 238 amino acid GFP isolated from the bioluminescent jellyfish *Aequorea victoria* in that one amino acid has been inserted after position 2 of the 238 amino acid sequence. When reference in this application is made to an amino acid position of GFP, the position is made with reference to that described by Chalfie et al., supra and thus of SEQ ID NO:2.

The term "blue fluorescent protein" (BFP) refers to mutants of wtGFP wherein the tyrosine at position 67 is converted to a histidine, which mutants emit a blue fluorescence. The non-limiting prototype is herein designated BFP ($Tyr_{67} \rightarrow His$).

A shorthand designation for mutations that result in a change in amino acid sequence is the one or three letter code for the original amino acid, the number of the position of the amino acid in the mwtGFP sequence, followed by the one or three letter code for the new amino acid. Thus, Phe65Leu or F65L both designate a mutation wherein the phenylalanine at position 65 of the mwtGFP is converted to leucine.

Salts of any of the proteins described herein will naturally occur when such proteins are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and Zwitterions formed by reactions between carboxylic acid and amino acid residues within the same molecule.

The terms "bioluminescent" and "fluorescent" refer to the ability of GFP or of a derivative thereof to emit light ("emitted or fluorescent light") of a characteristic wavelength when excited by light which is generally of a characteristic and different wavelength than that used to generate the emission.

The term "cellular fluorescence" denotes the fluorescence of a GFP-derived protein of the present invention when expressed in a cell, especially a mammalian cell.

The term "nucleic acid" refers to a deoxyribonucleotide or ribonucleotide polymer in either single- or double-stranded form, and unless specifically limited, encompasses known analogues of natural nucleotides that hybridize to nucleic acids in a manner similar to naturally occurring nucleotides. Unless otherwise indicated, a particular nucleic acid sequence implicitly provides the complementary sequence thereof, as well as the sequence explicitly indicated. As used herein, the terms "nucleic acid" and "gene" are interchangeable, and they encompass the term "cDNA."

The phrase "a nucleic acid sequence encoding" refers to a nucleic acid which contains sequence information that, if translated, yields the primary amino acid sequence of a specific protein or peptide. This phrase specifically encompasses degenerate codons (i.e., different codons which encode a single amino acid) of the native sequence or sequences which may be introduced to conform with codon preference in a specific host cell.

The phrase "nucleic acid construct" denotes a nucleic acid that is composed of two or more nucleic acid sequences that are derived from different sources and that are ligated together using methods known in the art.

The term "regulatory sequence" denotes all the non-coding elements of a nucleic acid sequence required for the correct and efficient expression of the "coding region" (i.e., the region that actually encodes the amino acid sequence of a peptide or protein), e.g., binding cites for polymerases and transcription factors, transcription and translation initiation and termination sequences, TATA box, a promoter to direct transcription, a ribosome binding site for translational initiation, polyadenylation sequences, enhancer elements.

The term "isolated" refers to material which is substantially or essentially free from components which normally accompany it as found in its native state (for example, a band on a gel). The isolated nucleic acids and the isolated proteins of this invention do not contain materials normally associated with their in situ environment, in particular, nuclear, cytosolic or membrane associated proteins or nucleic acids other than those nucleic acids which are indicated. The term "homogeneous" refers to a peptide or DNA sequence where the primary molecular structure (i.e., the sequence of amino acids or nucleotides) of substantially all molecules present in the composition under consideration is identical. The term "substantially" used in the preceding sentences preferably means at least 80% by weight, more preferably at least 95% by weight, and most preferably at least 99% by weight.

The nucleic acids of this invention, whether RNA, cDNA, genomic DNA, or a hybrid of the various combinations, are synthesized in vitro or are isolated from natural sources or recombinant clones. The nucleic acids claimed herein are present in transformed or transfected whole cells, in transformed or transfected cell lysates, or in a partially purified or substantially pure form. The nucleic acids of the present invention are obtained as homogeneous preparations. They may be prepared by standard techniques well known in the art, including selective precipitation with such substances as ammonium sulfate, isopropyl alcohol, ethyl alcohol, and/or exclusion, ion exchange or affinity column chromatography, immunopurification methods, and others.

The phrase "conservatively modified variants thereof," when used with reference to a protein, denotes conservative amino acid substitutions in which both the original and the substituted amino acids have similar structure (e.g., the R group contains a carboxylic acid) and properties (e.g., the original and the substituted amino acids are acidic, such as glutamic and aspartic acid), such that the substitutions do not essentially alter specified properties of the protein, such as fluorescence. Amino acid substitutions that are conservative are well known in the art. The phrase "conservatively modified variants thereof," when used to describe a reference nucleic acid, denotes nucleic acids having nucleotide substitutions that yield degenerate codons for a given amino acid or that encode conservative amino acid substitutions, as compared to the reference nucleic acid.

The term "recombinant" or "engineered" when used with reference to a nucleic acid or a protein generally denotes that the composition or primary sequence of said nucleic acid or protein has been altered from the naturally occurring sequence using experimental manipulations well known to those skilled in the art. It may also denote that a nucleic acid or protein has been isolated and cloned into a vector, or that the nucleic acid that has been introduced into or expressed in a cell or cellular environment other than the cell or cellular environment in which said nucleic acid or protein may be found in nature. The phrase "engineered *Aequorea victoria* fluorescent protein" specifically encompasses a protein obtained by introducing one or more sequence alterations into the coding region of a nucleic acid that encodes modified wild type *Aequorea victoria* GFP having SEQ ID NO:2, wherein the gene product of the engineered nucleic acid is a fluorescent protein recognized by antisera to modified wild type *Aequorea Victoria* GFP.

The term "recombinant" or "engineered" when used with reference to a cell indicates that, as a result of experimental manipulation, the cell replicates or expresses a nucleic acid or expresses a peptide or protein encoded by a nucleic acid, whose origin is exogenous to the cell. Recombinant cells can express nucleic acids that are not found within the native (non-recombinant) form of the cell. Recombinant cells can also express nucleic acids found in the native form of the cell wherein the nucleic acids are re-introduced into the cell by artificial means.

The term "vector" denotes an engineered nucleic acid construct that contains sequence elements that mediate the replication of the vector sequence and/or the expression of coding sequences present on the vector. Examples of vectors include eukaryotic and prokaryotic plasmids, viruses (for example, the HIV virus), cosmids, phagemids, and the like. The term "operably linked" refers to functional linkage between a first nucleic acid (for example, an expression control sequence such as a promoter or an array of transcription factor binding sites) and a second nucleic acid sequence, wherein the expression control sequence directs transcription of the nucleic acid corresponding to the second sequence. One or more selected isolated nucleic acids may be operably linked to a vector by methods known in the art.

"Transduction" or "transformation" denotes the process whereby exogenous extracellular DNA is introduced into a cell, such that the cell is capable of replicating and or expressing the exogenous DNA. Generally, a selected nucleic acid is first inserted into a vector and the vector is then introduced into the cell. For example, plasmid DNA that is introduced under appropriate environmental conditions may undergo replication in the transformed cell, and the replicated copies are distributed to progeny cells when cell division occurs. As a result, a new cell line is established, containing the plasmid and carrying the genetic determinants thereof. Transformation by a plasmid in this manner, where the plasmid genes are maintained in the cell line by plasmid replication, occurs at high frequency when the transforming plasmid DNA is in closed loop form, and does not or rarely occurs if linear plasmid DNA is used.

All the patents and publications cited in this disclosure are indicative of the level of skill of those skilled in the art to which this invention pertains and are all herein individually incorporated by reference for all purposes.

II. The GFP Mutants and Their Expression

A. The GFP mutants

The isolated nucleic acids reported here are those that encode an engineered protein derived from Aequorea victoria green fluorescent protein ("GFP") having a fluorescence at maximum emission that is at least five times greater, preferably ten times greater, and most preferably twenty times greater than the fluorescence at maximum emission of modified wild type GFP. In one embodiment, a nucleic acid encodes for leucine at amino acid position 65. This amino acid position is important for the enhanced fluorescence. In another embodiment the engineered isolated GFP nucleic acid also encodes for threonine at amino acid position 168. In an additional embodiment, the engineered isolated GFP nucleic acid further encodes for cysteine at amino acid position 66.

Also described here are GFP mutants that have enhanced blue fluorescent properties. These mutants have an isolated nucleic acid that encode an engineered Aequorea victoria blue fluorescent protein that encodes for histidine at amino acid position 67, leucine at amino acid position 65 and has a cellular fluorescence that is at least five times greater, preferably 10 times greater, most preferably 20 times greater than that of BFP(Tyr$_{67}$→His). An alternative isolated BFP nucleic acid is one that encodes for an engineered *Aequorea victoria* blue fluorescent protein wherein the engineered BFP has histidine at amino acid position 67 and alanine at amino acid position 164. A third engineered isolated BFP nucleic acid sequence is one that has histidine at amino acid position 67, leucine at amino acid position 65 and alanine at amino acid position 164.

The nucleic acid and amino acid sequences for the modified wild type GFP are set out in SEQ ID NO:1 and SEQ ID NO:2. The sequence is well-known, well-described and readily available for manipulation and use. Vectors bearing the nucleic acid sequence are commercially readily available from, for example, Clontech Laboratories, Inc., Clontech Laboratories, Inc., Palo Alto, Calif. Clontech provides a line of reporter vectors for GFP, including the cDNA construct described by Chalfie, et al., supra, a promoterless GFP vector for monitoring the expression of cloned promoters in mammalian cells, and a series of vectors for creating fusion proteins to either the amino or carboxy terminus of GFP.

One of skill in the art will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Berger and Kimmel, *Guide to Molecular Cloning Techniques, Methods in Enzymology* Volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., *Current Protocols*, a joint venture between Greene Publishing Associates, Inc. and John Wiley & Sons, Inc., (1994 Supplement) (Ausubel); Pirrung et al., U.S. Pat. No. 5,143, 854; and Fodor et al., Science, 251, 767–77 (1991). Product information from manufacturers of biological reagents and experimental equipment also provide information useful in known biological methods. Such manufacturers include the SIGMA Chemical Company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill. Using these techniques, it is possible to substitute at will any nucleotide in a nucleic acid that encodes any GFP or BFP disclosed herein or any amino acid in a GFP or BFP described herein for a predetermined nucleotide or amino acid. For example, it is possible to generate at will modified GFPs and BFP(Tyr$_{67}$→His)s that contain leucine at position 65 and one or two or three additional mutations at any other position of the mwtGFP or BFP(Tyr$_{67}$→His).

The sequence of the cloned genes and synthetic oligonucleotides can be verified using the chemical degradation method of A. M. Maxam et al. (1980), *Methods in Enzymology* 65:499–560. The sequence can be confirmed after the assembly of the oligonucleotide fragments into the double-stranded DNA sequence using the method of Maxam and Gilbert, supra, or the chain termination method for sequencing double-stranded templates of R. B. Wallace et al. (1981), *Gene*, 16:21–26. DNA sequencing may also be performed by the PCR-assisted fluorescent terminator method (ReadyReaction DyeDeoxy Terminator Cycle Sequencing Kit, ABI, Columbia, Md.) according to the manufacturer's instructions, using the ABI Model 373A DNA Sequencing System. Sequencing data is analyzed using the commercially available Sequencher program (Gene Codes, Gene Codes, Ann Arbor, Mich.).

B. Expression of Mutant GFP

Clearly, the nucleic acid sequences of the present invention are excellent reporter sequences since the expressed proteins can be readily detected by fluorescence as described below. The sequences can be used in conjunction with any application appreciated to date for GFP and further in applications where a greater degree of fluorescence is required. Expression of the sequences described herein whether expression is desired alone or in combination with other sequences of interest is described below.

Vectors to which selected foreign nucleic acids are operably linked may be used to introduce these selected nucleic acids into host cells and mediate their replication and/or expression. Cloning vectors are useful for replicating the foreign nucleic acids and obtaining clones of specific foreign nucleic acid-containing vectors. Expression vectors mediate the expression of the foreign nucleic acid. Some vectors are both cloning and expression vectors.

Once a nucleic acid is synthesized or isolated and inserted into a vector and cloned, one may express the nucleic acid in a variety of recombinantly engineered cells known to those of skill in the art. As used herein, "expression" refers to transcription of nucleic acids, either without or preferably with subsequent translation.

Expression of a mutant BFP or of modified wild type or mutant GFP can be enhanced by including multiple copies of the GFP-encoding nucleic acid in a transformed host, by selecting a vector known to reproduce in the host, thereby producing large quantities of protein from exogenous inserted DNA (such as pUC8, ptac12, or pIN-III-ompA1, 2, or 3), or by any other known means of enhancing peptide expression. In all cases, mwtGFP or mutant GFPs will be expressed when the DNA sequence is functionally inserted into a vector. "Functionally inserted" means that it is inserted in proper reading frame and orientation. Typically, a GFP gene will be inserted downstream from a promoter and will be followed by a stop codon, although production as a hybrid protein followed by cleavage may be used, if desired.

Examples of cells which are suitable for the cloning and expression of the nucleic acids of the invention include bacteria, yeast, filamentous fungi, insect (especially employing baculoviral vectors), and mammalian cells, in particular cells capable of being maintained in tissue culture.

Host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation and micro-injection of the DNA directly into the cells.

It is expected that those of skill in the art are knowledgeable in the numerous systems available for cloning and expression of nucleic acids. In brief summary, the expression of natural or synthetic nucleic acids is typically achieved by operably linking a nucleic acid of interest to a promoter (which is either constitutive or inducible), and incorporating the construct into an expression vector. The vectors are suitable for replication and integration in prokaryotes, eukaryotes, or both. Typical cloning vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, e.g., Sambrook and Ausbel (both supra).

1. Expression in Prokaryotes

Prokaryotic systems for cloning and/or expressing engineered GFP or BFP proteins are available using *E. coli*, Bacillus sp. and Salmonella (Palva, I. et al. (1983), *Gene* 22:229–235; Mosbach, K. et al. (1983), *Nature* 302:543–545. To obtain high level expression in a prokaryotic system of a cloned nucleic acid such as those encoding engineered GFPs or BFPs, it is essential to construct expression vectors which contain, at a minimum, a strong promoter to direct transcription, a ribosome binding site for translational initiation, a transcription/translation terminator, a bacterial replicon, a nucleic acid encoding antibiotic resistance to permit selection of bacteria that harbor recombinant plasmids, and unique restriction sites in nonessential regions of the plasmid to allow insertion of foreign nucleic acids. The particular antibiotic resistance gene chosen is not critical, any of the many resistance genes known in the art are suitable. Examples of regulatory regions suitable for this purpose in *E. coli* are the promoter and operator region of the *E. coli* tryptophan biosynthetic pathway as described by Yanofsky, C. (1984), *J. Bacteriol.*, 158:1018–1024, and the leftward promoter of phage lambda ($P_L$) as described by Herskowitz, I. and Hagen, D. (1980), *Ann. Rev. Genet.*, 14:399–445 (1980).

The particular vector used to transport the genetic information into the cell is not particularly critical. Any of the conventional vectors used for replication, cloning and/or expression in prokaryotic cells may be used.

The foreign nucleic acid can be incorporated into a nonessential region of the host cell's chromosome. This is achieved by first inserting the nucleic acid into a vector such that it is flanked by regions of DNA homologous to the insertion site in the host chromosome. After introduction of the vector into a host cell, the foreign nucleic acid is incorporated into the chromosome by homologous recombination between the flanking sequences and chromosomal DNA.

Detection of the expressed protein is achieved by methods known in the art as radioimmunoassays, or Western blotting techniques or immunoprecipitation. Purification from *E. coli* can be achieved following procedures described in U.S. Pat. No. 4,511,503.

2. Expression in Eukaryotes

Standard eukaryotic transfection methods are used to produce mammalian, yeast or insect cell lines which express large quantities of engineered GFP or BFP protein which are then purified using standard techniques. See, e.g., Colley et al. (1989), *J. Biol. Chem.* 264:17619–17622, and Guide to Protein Purification, in Vol. 182 of *Methods in Enzymology* (Deutscher ed., 1990), D. A. Morrison (1977), *J. Bact.*, 132:349–351, or by J. E. Clark-Curtiss and R. Curtiss (1983), *Methods in Enzymology* 101:347–362, Eds. R. Wu et al., Academic Press, New York.

The particular eukaryotic expression vector used to transport the genetic information into the cell is not particularly critical. Any of the conventional vectors used for expression in eukaryotic cells may be used. Expression vectors containing regulatory elements from eukaryotic viruses such as retroviruses are typically used. SV40 vectors include pSVT7 and pMT2. Vectors derived from bovine papilloma virus include pBV-1MTHA, and vectors derived from Epstein Barr virus include pHEBO, and p205. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The expression vector typically comprises a eukaryotic transcription unit or expression cassette that contains all the elements required for the expression of the engineered GFP or BFP DNA in eukaryotic cells. A typical expression cassette contains a promoter operably linked to the DNA sequence encoding a engineered GFP or BFP protein and signals required for efficient polyadenylation of the transcript.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression*, Cold Spring Harbor Press, Cold Spring Harbor, N.Y. 1983, which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned nucleic acids or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The DNA sequence encoding the engineered GFP or BFP protein may typically be linked to a cleavable signal peptide sequence to promote secretion of the encoded protein by the transformed cell. Such signal peptides would include, among others, the signal peptides from tissue plasminogen activator, insulin, neuron growth factor, and juvenile hormone esterase of *Heliothis virescens*. Additional elements of the cassette may include enhancers and, if genomic DNA is used as the structural gene, introns with functional splice donor and acceptor sites.

The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired nucleic acid.

The vectors usually comprise selectable markers which result in nucleic acid amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving nucleic acid amplification are also suitable, such as using a bacculovirus vector in insect cells, with the engineered GFP or BFP encoding sequence under the direction of the polyhedrin promoter or other strong baculovirus promoters.

The expression vectors of the present invention will typically contain both prokaryotic sequences that facilitate the cloning of the vector in bacteria as well as one or more eukaryotic transcription units that are expressed only in eukaryotic cells, such as mammalian cells. The prokaryotic sequences are preferably chosen such that they do not interfere with the replication of the DNA in eukaryotic cells.

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign nucleic acidic material into a host cell (see Sambrook et al., supra). It is only necessary that the particular genetic engineering procedure utilized be capable of successfully introducing at least one nucleic acid into the host cell which is capable of expressing the engineered GFP or BFP protein.

3. Expression in insect cells

The baculovirus expression vector utilizes the highly expressed and regulated *Autographa californica* nuclear polyhedrosis virus (AcMNPV) polyhedrin promoter modified for the insertion of foreign nucleic acids. Synthesis of polyhedrin protein results in the formation of occlusion bodies in the infected insect cell. The baculovirus vector utilizes many of the protein modification, processing, and transport systems that occur in higher eukaryotic cells. The recombinant eukaryotic proteins expressed using this vector have been found in many cases to be, antigenically, immunogenically, and functionally similar to their natural counterparts.

Briefly, a DNA sequence encoding an engineered GFP or BFP is inserted into a transfer plasmid vector in the proper orientation downstream from the polyhedrin promoter, and flanked on both ends with baculovirus sequences. Cultured insect cells, commonly *Spodoptera frugiperda* cells, are transfected with a mixture of viral and plasmid DNAs. The virus that develop, some of which are recombinant virus that result from homologous recombination between the two DNAs, are plated at 100–1000 plaques per plate. The plaques containing recombinant virus can be identified visually because of their ability to form occlusion bodies or by DNA hybridization. The recombinant virus is isolated by plague purification. The resulting recombinant virus, capable of expressing engineered GFP or BFP, is self-propagating in that no helper virus is required for maintenance or replication. After infecting an insect culture with recombinant virus, one can expect to find recombinant protein within 48–72 hours. The infection is essentially lytic within 4–5 days.

There are a variety of transfer vectors into which the engineered GFP or BFP nucleic acid can be inserted. For a summary of transfer vectors see Luckow, V. A. and Summers, M. D. (1988), *Bio/Technology* 6:47–55. Preferred is the transfer vector pAcUW21 described by Bishop, D. H. L. (1992) in *Seminars in Virology* 3:253–264.

4. Retroviral Vectors

Retroviral vectors are particularly useful for modifying eukaryotic cells because of the high efficiency with which the retroviral vectors transduce target cells and integrate into the target cell genome. Additionally, the retroviruses harboring the retoviral vector are capable of infecting cells from a wide variety of tissues.

Retroviral vectors are produced by genetically manipulating retroviruses. Retroviruses are RNA viruses because the viral genome is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R. C. (1983), In: *Experimental Manipulation of Gene Expression,* M. Inouye (ed), 155–173; Mann, R. et al. (1983), *Cell,* 33:153–159; Cone, R. D. and R. C. Mulligan (1984), *Proceedings of the National Academy of Sciences, U.S.A.* 81:6349–6353.

The design of retroviral vectors is well known to one of skill in the art. See Singer, M. and Berg, P. supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa (1986), *Biotechniques* 4:504–512, Mann, et al. (1983), *Cell* 33:153–159, Cone and Mulligan (1984), *Proc. Natl. Acad. Sci. USA* 81:6349–6353, Eglitis, M. A, et al. (1988) *Biotechniques* 6:608–614, Miller, A. D. et al. (1989) *Biotechniques* 7:981–990, Miller, A. D. (1992) *Nature,* supra, Mulligan, R. C. (1993), supra. and Gould, B. et al., and International Patent Application No. WO 92/07943 entitled "Retroviral Vectors Useful in Gene Therapy." The teachings of these patents and publications are incorporated herein by reference.

The retroviral vector particles are prepared by recombinantly inserting the nucleic acid encoding engineered GFP or BFP into a retrovirus vector and packaging the vector with retroviral capsid proteins by use of a packaging cell line. The resultant retroviral vector particle is incapable of replication in the host cell and is capable of integrating into the host cell genome as a proviral sequence containing the engineered GFP or BFP nucleic acid. As a result, the patient is capable of producing engineered GFP or BFP and metabolize glycogen to completion.

Packaging cell lines are used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are available in the prior art. Examples of these cell lines include Crip, GPE86, PA317 and PG13. See Miller et al. (1991), *J. Virol.* 65:2220–2224, which is incorporated herein by reference. Examples of other packaging cell lines are described in Cone, R. and Mulligan, R. C. (1984), *Proceedings of the National Academy of Sciences, U.S.A.,* 81:6349–6353 and in Danos, O. and R. C. Mulligan (1988), *Proceedings of the National Academy of Sciences, U.S.A.,* 85:6460–6464, Eglitis, M. A, et al. (1988) *Biotechniques* 6:608–614, also all incorporated herein by reference.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

Transforming cells with nucleic acids can involve, for example, incubating the cells with viral vectors (e.g., retroviral or adeno-associated viral vectors) containing with cells within the host range of the vector. See, e.g., *Methods in Enzymology*, Vol. 185, Academic Press, Inc., San Diego, Calif. (D. V. Goeddel, ed.) (1990) or M. Krieger (1990), *Gene Transfer and Expression—A Laboratory Manual*, Stockton Press, New York, N.Y., and the references cited therein.

5. Transformation with adeno-associated virus

Adeno associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993), *Current Opinion in Genetic and Development* 3:74–80 and the references cited therein provides an overview of the AAV life cycle.

AAV-based vectors are used to transduce cells with target nucleic acids, e.g., in the in vitro production of nucleic acids and peptides, and in in vivo and ex vivo gene therapy procedures. See, West et al. (1987), *Virology* 160:38–47; Carter et al. (1989) U.S. Pat. No. 4,797,368; Carter et al. (1993), WO 93/24641; Kotin (1994), *Human Gene Therapy* 5:793–801; Muzyczka (1994), *J. Clin. Invest.* 94:1351 and Samulski (supra) for an overview of AAV vectors.

Recombinant AAV vectors (rAAV vectors) deliver foreign nucleic acids to a wide range of mammalian cells (Hermonat & Muzycka (1984), *Proc. Natl. Acad. Sci. USA* 81:6466–6470; Tratschin et al. (1985), *Mol. Cell Biol.* 5:3251–3260), integrate into the host chromosome (Mclaughlin et al. (1988), *J. Virol.* 62:1963–1973), and show stable expression of the transgene in cell and animal models (Flotte et al. (1993), *Proc. Natl. Acad. Sci. USA* 90:10613–10617). Moreover, unlike some retroviral vectors, rAAV vectors are able to infect non-dividing cells (Podsakoff et al. (1994), *J. Virol.* 68:5656–66; Flotte et al. (1994), *Am. J. Respir. Cell Mol. Biol.* 11:517–521). Further advantages of rAAV vectors include the lack of an intrinsic strong promoter, thus avoiding possible activation of downstream cellular sequences, and their naked eicosahedral capsid structure, which renders them stable and easy to concentrate by common laboratory techniques. rAAV vectors are used to inhibit, e.g., viral infection, by including anti-viral transcription cassettes in the rAAV vector which comprise an inhibitor of the invention.

6. Expression in recombinant vaccinia virus-infected cells

The nucleic acid encoding engineered GFP or BFP is inserted into a plasmid designed for producing recombinant vaccinia, such as pGS62, Langford, C. L. et al. (1986), *Mol. Cell. Biol.* 6:3191–3199. This plasmid consists of a cloning site for insertion of foreign nucleic acids, the P7.5 promoter of vaccinia to direct synthesis of the inserted nucleic acid, and the vaccinia TK gene flanking both ends of the foreign nucleic acid.

When the plasmid containing the engineered GFP or BFP nucleic acid is constructed, the nucleic acid can be transferred to vaccinia virus by homologous recombination in the infected cell. To achieve this, suitable recipient cells are transfected with the recombinant plasmid by standard calcium phosphate precipitation techniques into cells already infected with the desirable strain of vaccinia virus, such as Wyeth, Lister, WR or Copenhagen. Homologous recombination occurs between the TK gene in the virus and the flanking TK gene sequences in the plasmid. This results in a recombinant virus with the foreign nucleic acid inserted into the viral TK gene, thus rendering the TK gene inactive. Cells containing recombinant viruses are selected by adding medium containing 5-bromodeoxyuridine, which is lethal for cells expressing a TK gene.

Confirmation of production of recombinant virus is achieved by DNA hybridization using cDNA encoding the engineered GFP or BFP and by immunodetection techniques using antibodies specific for the expressed protein. Virus stocks may be prepared by infection of cells such as HeLA S3 spinner cells and harvesting of virus progeny.

7. Expression in cell cultures

GFP- or BFP-encoding nucleic acids can be ligated to various expression vectors for use in transforming host cell cultures. The culture of cells used in conjunction with the present invention is well known in the art. Freshney (1994) (*Culture of Animal Cells, a Manual of Basic Technique, third edition* Wiley-Liss, New York), Kuchler et al. (1977) *Biochemical Methods in Cell Culture and Virology*, Kuchler, R. J., Dowden, Hutchinson and Ross, Inc., and the references cited therein provides a general guide to the culture of cells. Illustrative cell cultures useful for the production of recombinant proteins include cells of insect or mammalian origin. Mammalian cell systems often will be in the form of monolayers of cells, although mammalian cell suspensions are also used. Illustrative examples of mammalian cell lines include monocytes, lymphocytes, macrophage, VERO and HeLa cells, Chinese hamster ovary (CHO) cell lines, W138, BHK, Cos-7 or MDCK cell lines (see, e.g., Freshney, supra).

Cells of mammalian origin are illustrative of cell cultures useful for the production of the engineered GFP or BFP . Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines.

As indicated above, the vector, e.g., a plasmid, which is used to transform the host cell, preferably contains DNA sequences to initiate transcription and sequences to control the translation of the engineered GFP or BFP nucleic acid sequence. These sequences are referred to as expression control sequences. Illustrative expression control sequences are obtained from the SV-40 promoter (*Science* 222:524–527, (1983)), the CMV i.e. Promoter (*Proc. Natl. Acad. Sci.* 81:659–663, (1984)) or the metallothionein promoter (Nature 296:39–42, (1982)). The cloning vector containing the expression control sequences is cleaved using restriction enzymes and adjusted in size as necessary or desirable and ligated with sequences encoding the engineered GFP or BFP protein by means well known in the art.

The vectors for transforming cells in culture typically contain gene sequences to initiate transcription and translation of the engineered GFP or BFP gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

As mentioned above, when higher animal host cells are employed, polyadenlyation or transcription terminator sequences from known mammalian genes need to be incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, J. et al. (1983), *J. Virol.* 45: 773–781).

Additionally gene sequences to control replication in the host cell may be incorporated into the vector such as those found in bovine papilloma virus type-vectors. Saveria-Campo, M. (1985), *"Bovine Papilloma virus DNA a Eukaryotic Cloning Vector"* in DNA Cloning Vol. II a Practical Approach Ed. D. M. Glover, IRL Press, Arlington, Va. pp. 213–238.

The transformed cells are cultured by means well known in the art. For example, as published in Kuchler, R. J. et al., (1977), *Biochemical Methods in Cell Culture and Virology.*

In addition to the above general procedures which can be used for preparing recombinant DNA molecules and transformed unicellular organisms in accordance with the practices of this invention, other known techniques and modifications thereof can be used in carrying out the practice of the invention. Any known system for expression of isolated genes is suitable for use in the present invention. For example, viral expression systems such as the bacculovirus expression system are specifically contemplated within the scope of the invention. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,319,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering. Transferring the isolated GFP cDNA to other expression vectors will produce constructs which improve the expression of the GFP polypeptide in *E. coli* or express GFP in other hosts.

III. Detection of GFP and BFP Nucleic Acids and Proteins

A. General detection methods

The nucleic acids and proteins of the invention are detected, confirmed and quantified by any of a number of means well known to those of skill in the art. The unique quality of the inventive expressed proteins here is that they provide an enhanced fluorescence which can be readily and easily observed. Fluorescence assays for the expressed proteins are described in detail below. Other general methods for detecting both nucleic acids and corresponding proteins include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

A variety of methods of specific DNA and RNA measurement using nucleic acid hybridization techniques are known to those of skill in the art. For example, one method for evaluating the presence or absence of engineered GFP or BFP DNA in a sample involves a Southern transfer. Southern et al. (1975), *J. Mol. Biol.* 98:503. Briefly, the digested genomic DNA is run on agarose slab gels in buffer and transferred to membranes. Hybridization is carried out using the probes discussed above. Visualization of the hybridized portions allows the qualitative determination of the presence or absence of engineered GFP or BFP genes.

Similarly, a Northern transfer may be used for the detection of engineered GFP or BFP mRNA in samples of RNA from cells expressing the engineered GFP or BFP gene. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the engineered GFP or BFP transcript.

The selection of a nucleic acid hybridization format is not critical. A variety of nucleic acid hybridization formats are known to those skilled in the art. For example, common formats include sandwich assays and competition or displacement assays. Hybridization techniques are generally described in *"Nucleic Acid Hybridization, A Practical Approach,"* Ed. Hames, B. D. and Higgins, S. J., IRL Press, 1985; Gall and Pardue (1969), *Proc. Natl. Acad. Sci. USA* 63:378–383; and John, Burnsteil and Jones (1969), *Nature* 223:582–587.

For example, sandwich assays are commercially useful hybridization assays for detecting or isolating nucleic acid sequences. Such assays utilize a "capture" nucleic acid covalently immobilized to a solid support and labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The nucleic acid sequences used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may act as a negative probe in an assay sample where only the mutant engineered GFP or BFP is present.

Labelled signal nucleic acids, whether those described herein or others known in the art are used to detect hybridization. Complementary nucleic acids or signal nucleic acids may be labelled by any one of several methods typically used to detect the presence of hybridized polynucleotides. One common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P. (1985), "Practice and Theory of Enzyme Immunoassays," *Laboratory Techniques in Biochemistry and Molecular Biology*, Burdon, R. H., van Knippenberg, P. H., Eds., Elsevier, pp. 9–20.)

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al. (1987), U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990), *Chem. Eng. News* 36–47; *J. NIH Res.* (1991) 3:81–94; (Kwoh et al. (1989), *Proc. Natl. Acad. Sci. USA* 86:1173; Guatelli et al. (1990), *Proc. Natl. Acad. Sci. USA* 87:1874; Lomell et al. (1989), *J. Clin. Chem.* 35:1826; Landegren et al. (1988), *Science* 241:1077–1080; Van Brunt (1990), *Biotechnology* 8:291–294; Wu and Wallace (1989), *Gene* 4:560; Barringer et al. (1990), *Gene* 89:117, and Sooknanan and Malek (1995), *Biotechnology* 13:563–564. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components are typically synthesized chemically according to the solid phase phosphoramidite triester method described by Beaucage and Caruthers (1981), *Tetrahedron Letts.* 22(20):1859–1862, e.g., using an automated synthesizer, as described in Needham-VanDevanter et al. (1984), *Nucleic Acids Res.* 12:6159–6168. Purification of oligonucleotides, where necessary, is typically performed by either native acrylamide gel electrophoresis or by anion-exchange HPLC as described in Pearson and Regnier (1983), *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

An alternative means for determining the level of expression of the engineered GFP or BFP gene is in situ hybridization. In situ hybridization assays are well known and are generally described in Angerer et al. (1987), *Methods Enzymol.* 152:649–660. In an in situ hybridization assay cells are fixed to a solid support, typically a glass slide. If DNA is to be probed, the cells are denatured with heat or alkali. The cells are then contacted with a hybridization solution at a moderate temperature to permit annealing of engineered GFP or BFP specific probes that are labelled. The probes are preferably labelled with radioisotopes or fluorescent reporters.

B. Fluorescence Assay

When a fluorophore such as protein that is capable of fluorescing is exposed to a light of appropriate wavelength, it will absorb and store light and then release the stored light energy. The range of wavelengths that a fluorophore is capable of absorbing is the excitation spectrum and the range of wavelengths of light that a fluorophore is capable of emitting is the emission or fluorescence spectrum. The excitation and fluorescence spectra for a given fluorophore usually differ and may be readily measured using known instruments and methods. For example, scintillation counters and photometers (e.g. luminometers), photographic film, and solid state devices such as charge coupled devices, may be used to detect and measure the emission of light.

The nucleic acids, vectors, mutant proteins provided herein, in combination with well known techniques for over-expressing recombinant proteins, make it possible to obtain unlimited supplies of homogeneous mutant GFPs and BFPs. These modified GFPs or BFPs having increased fluorescent activity replace wtGTP or other currently employed tracers in existing diagnostic and assay systems. Such currently employed tracers include radioactive atoms or molecules and color-producing enzymes such as horseradish peroxidase.

The benefits of using the mutants of the present invention are at least four-fold: the modified GFPs and BFPs are safer than radioactive-based assays, modified GFPs and BFPs can be assayed quickly and easily, and large numbers of samples can be handled simultaneously, reducing overall handling and increasing efficiency. Of great significance, the expression and subcellular distribution of the fluorescent proteins within cells can be detected in living tissues without any other experimental manipulation than to placing the cells on a slide and viewing them through a fluorescence microscope. This represents a vast improvement over methods of immunodetection that require fixation and subsequent labelling.

The modified GFPs and BFPs of the present invention can be used in standard assays involving a fluorescent marker. For example, ligand-ligator binding pairs that can be modified with the mutants of the present invention without disrupting the ability of each to bind to the other can form the basis of an assay encompassed by the present invention. These and other assays are known in the art and their use with the GFPs and BFPs of the present invention will become obvious to one skilled in the art in light of the teachings disclosed herein. Examples of such assays include competitive assays wherein labeled and unlabeled ligands competitively bind to a ligator, noncompetitive assay where a ligand is captured by a ligator and either measured directly or "sandwiched" with a secondary ligator that is labeled. Still other types of assays include immunoassays, single-step homogeneous assays, multiple-step heterogeneous assays, and enzyme assays.

In a number of embodiments, the mutant GFPs and BFPs are combined with fluorescent microscopy using known techniques (see, e.g., Stauber et al., Virol. 213:439–454 (1995)) or preferably with fluorescence activated cell sorting (FACS) to detect and optionally purify or clone cells that express specific recombinant constructs. For a brief overview of the FACS and its uses, see: Herzenberg et al., 1976, "Fluorescence activated cell sorting", Sci. Amer. 234, 108; see also FLOW CYTOMETRY AND SORTING, eds. Melamad, Mullaney and Mendelsohn, John Wiley and Sons, Inc., New York, 1979). Briefly, fluorescence activated cell sorters take a suspension of cells and pass them single file into the light path of a laser placed near a detector. The laser usually has a set wavelength. The detector measures the fluorescent emission intensity of each cell as it passes through the instrument and generates a histogram plot of cell number versus fluorescent intensity. Gates or limits can be placed on the histogram thus identifying a particular population of cells. In one embodiment, the cell sorter is set up to select cells having the highest probe intensity, usually a small fraction of the cells in the culture, and to separate these selected cells away from all the other cells. The level of intensity at which the sorter is set and the fraction of cells which is selected, depend on the condition of the parent culture and the criteria of the isolation. In general, the operator should first sort an aliquot of the culture, and record the histogram of intensity versus number of cells. The operator can then set the selection level and isolate an appropriate number of the most active cells. Currently, fluorescence activated cell sorters are equipped with automated cell cloning devices. Such a device enables one to instruct the instrument to singly deposit a selected cell into an individual growth well, where it is allowed to grow into a monoclonal culture. Thus, genetic homogeneity is established within the newly cloned culture.

IV. General Applications for the GFP Mutants

It should be self-evident that the mutant GFP and BFP sequences described here have unlimited uses, particularly as signal or reporter sequences for the co-expression of other nucleic acid sequences of interest and/or to track the location and/or movement of other sequences within the cell, within tissue and the like. For example, these reporter type sequences could be used to track the spread (or lack thereof) of a disease causal agent in drug screening assays or could readily be used in diagnostics. Some of the more interesting applications are described below.

A. Protein Trafficking

Normally, expressed mutant GFPs and BFPs are distributed throughout the cell (particularly mammalian cells), except for the nucleolus. However, as described below, when a GFP mutant is fused to the HIV-1 Rev protein, a hybrid molecule results which retains the Rev function and is localized mainly in the nucleolus where Rev is found. Fusion to the N-terminal domain of the HIV-1 Nef protein produces a hybrid protein detectable in the plasma membrane. Thus, the GFP mutants can be used to monitor the subcellular targeting and transport of proteins to which they are fused.

B. Gene Therapy

The mutant GFPs described here have interesting and useful applications in gene therapy. Gene therapy in general is the correction of genetic defects by insertion of exogenous cellular genes that encode a desired function into cells that lack that function, such that the expression of the exogenous gene a) corrects a genetic defect or b) causes the destruction of cells that are genetically defective. Methods of gene therapy are well known in the art, see, for example, Lu, M., et al. (1994), Human Gene Therapy 5:203; Smith, C. (1992), J. Hematotherapy 1:155; Cassel, A., et al. (1993), Exp. Hematol. 21-:585 (1993); Larrick, J. W. and Burck, K. L., GENE THERAPY: APPLICATION OF MOLECULAR BIOLOGY, Elsevier Science Publishing Co., Inc., New York, N.Y. (1991) and Kreigler, M. GENE TRANSFER AND EXPRESSION: A LABORATORY MANUAL, W. H. Freeman and Company, New York (1990), each incorporated herein by reference. One modality of gene therapy involves (a) obtaining from a patient a viable sample of primary cells of a particular cell type; (b) inserting into these primary cells a nucleic acid segment encoding a desired gene product; (c) identifying and isolating cells and cell lines that express the gene product; (d) re-introducing cells that express the gene product; (e) removing from the patient an aliquot of tissue including cells resulting from step c and their progeny; and (f) determining the quantity of the cells resulting from step c and their progeny, in said aliquot. The introduction into cells in step c of a polycistronic vector that encodes GFP or BFP in addition to the desired gene allows for the quick identification of viable cells that contain and express the desired gene.

Another gene therapy modality involves inserting the desired nucleic acid into selected tissue cells in situ, for example into cancerous or diseased cells, by contacting the target cells in situ with retroviral vectors that encode the gene product in question. Here, it is important to quickly and reliably assess which and what proportion of cells have been transfected. Co-expression of GFP and BFP permits a quick assessment of proportion of cells that are transfected, and levels of expression.

C. Diagnostics

One potential application of the GFP/BFP variants is in diagnostic testing. The GFP/BFP gene, when placed under the control of promoters induced by various agents, can serve as an indicator for these agents. Established cell lines or cells and tissues from transgenic animals carrying GFP/BFP expressed under the desired promoter will become fluorescent in the presence of the inducing agent.

Viral promoters which are transactivated by the corresponding virus, promoters of heat shock genes which are induced by various cellular stresses as well as promoters which are sensitive to organismal responses, e.g. inflammation, can be used in combination with the described GFP/BFP mutants in diagnostics.

In addition, the effect of selected culture conditions and components (salt concentrations, pH, temperature, trans-acting regulatory substances, hormones, cell-cell contacts, ligands of cell surface and internal receptors) can be assessed by incubating cells in which sequences encoding the fluorescent proteins provided herein are operably linked to nucleic acids (especially regulatory elements such as promoters) derived from a selected gene, and detecting the expression and location of fluoresence.

D. Toxicology

Another application of the GFP/BFP-based methodologies is in the area of toxicology. Assessment of the mutagenic potential of any compound is a prerequisite for its use. Until recently, the Ames assay in Salmonella and tests based on chromosomal aberrations or sister chromatid exchanges in cultured mammalian cells were the main tools in toxicology. However, both assays are of limited sensitivity and specificity and do not allow studies on mutation induction in various organs or tissues of the intact organism.

The introduction of transgenic mice with a mutational target in a shuttle vector has made possible the detection of induced mutations in different tissues in vivo. The assay involves DNA isolation from tissues of exposed mice, packaging of the target DNA into bacteriophage lambda particles and subsequent infection of E. coli. The mutational target in this assay is either the lacZ or lacI genes and quantitation of blue vs white plaques on the bacterial lawn allows for mutagenic assessment.

GFP/BFP could significantly simplify both the tissue culture and transgenic mouse procedures. Expression of GFP/BFP under the control of a repressor, which in turn is driven by the promoter of a constitutively expressed gene, will establish a rapid method for evaluating the mutagenic potential of an agent. The presence of fluorescent cells, following exposure of a cell line, tissue or whole animal carrying the GFP/BFP-based detection construct, will reflect the mutagenicity of the compound in question. GFP/BFP expressed under the control of the target DNA, the repressor gene, will only be synthesized when the repressor is inactivated or turned off or the repressor recognition sequences are mutated. Direct visualization of the detector cell line or tissue biopsy can qualitatively assess the mutagenicity of the agent, while FACS of the dissociated cells can provide for quantitative analysis.

E. Drug Screening

The GFP/BFP detection system could also significantly expedite and reduce the cost of some current drug screening procedures. A dual color screening system (DCSS), in which GFP is placed under the promoter of a target gene and BFP is expressed from a constitutive promoter, could provide for rapid analysis of agents that specifically affect the target gene. Established cell lines with the DCSS could be screened with hundreds of compounds in few hours. The desired drug will only influence the expression of GFP. Non-specific or cytotoxic effects will be detected by the second marker, BFP. The advantages of this system are that no exogenous substances are required for GFP and BFP detection, the assay can be used with single cells, cell populations, or cell extracts, and that the same detection technology and instrumentation is used for very rapid and non-destructive detection.

The search for antiviral agents which specifically block viral transcription without affecting cellular transcription, could be significantly improved by the DCSS. In the case of HIV, appropriate cell lines expressing GFP under the HIV LTR and BFP under a cellular constitutive promoter, could identify compounds which selectively inhibit HIV transcription. Reduction of only the green but not the blue fluorescent signal will indicate drug specificity for the HIV promoter. Similar approaches could also be designed for other viruses.

Furthermore, the search for antiparasitic agents could also be helped by the DCSS. Established cell lines or transgenic nematodes or even parasitic extracts where expression of GFP depends on parasite-specific trans splicing sequences while BFP is under the control of host-specific cis splicing elements, could provide for rapid screen of selective antiparasitic drugs.

The invention will be more readily understood by reference to the following specific examples which are included for purposes of illustration only and are not intended to limit the invention unless so stated.

EXAMPLES

The following general protocol was used to generate mutant GFP- or BFP-encoding nucleic acids, transform host cells, and express the mutant GFP and BFP proteins:

Clone a nucleic acid that encodes either mwtGFP or BFP(Tyr$_{67}$→His), under the control of eukaryotic or prokaryotic promoters, into a standard ds-DNA plasmid Convert the plasmid vector to a ss-DNA by standard methods Anneal the ss-DNA to 40–50 nucleotide DNA oligomers having base mismatches at the site(s) intended to be engineered Convert the ss-DNA to a closed ds-DNA plasmid vector by use of DNA polymerase and standard protocols Identify plasmids containing the desired mutations by restriction analysis following plasmid DNA isolation from E. coli strains transformed with the mutagenized DNA verify the presence of mutations by DNA sequencing transfect human transformed embryonic kidney 293 cells with equal amounts of DNA from the appropriate plasmids compare the fluorescence intensity of the signals Nucleic acids and vectors The mwtGFP cDNA (SEQ ID NO:1) was obtained from Dr. Chalfie of Columbia University. All mutants described were obtained by modifying this mwtGFP sequence as detailed below.

The vectors used to clone and to express the GFPs and BFPs are derivatives of the commercially available plasmids pcDNA3 (Invitrogen, San Diego, Calif.), pBSSK+ (Stratagene, La Jolla, Calif.) and pET11a (Novagen, Madison, Wis.).

mwtGFP protein expression in mammalian cells

Several vectors for the expression of GFP in mammalian cells were constructed:

pFRED4 carries the mwtGFP sequences under the control of the cytomegalovirus (CMV) early promoter and the polyadenylation signal of the Human immunodeficiency Virus-1 (HIV) 3' Long Terminal Repeat (LTR). To derive pFRED4 we amplified the GFP coding sequence from plasmid #TU58 (Chalfie et al., 1994) by the polymerase chain reaction (PCR). For PCR amplification of the GFP coding region, oligonucleotides #16417 and #16418 were used as primers. Oligonucleotide #16417:

5'-GGAGGCGCGCAAGAAATGGCTAGCAAAGGA
GAAGA-3'                              (SEQ ID NO:3), containing the BssHII recognition sequence and the translation initiation sequence of the HIV-1 Tat protein, was the sense primer. The antisense primer, #16418:

5'-GCGGGATCCTTATTTGTATAGTTCATCCATG
CCATG-3'                              (SEQ ID NO:4)

contained the BamHI recognition sequence. The amplified fragment was digested with BssHII and BamHI and cloned into BssHII and BamHI digested pCMV37M1-10D, a plasmid containing the CMV early promoter and the HIV-1 p37gag region, followed by several cloning sites and the HIV-1 3' LTR. Thus the p37gag gene was replaced by GFP, resulting in pFRED4.

In a second step, the 1485 bp fragment from pFRED4, generated from StuI and BamHI double digestion, was subcloned into the 4747 bp vector derived from the NruI and BamHI double digestion of pcDNA3. The resulting plasmid, pFRED7 (SEQ ID NO:5), expresses GFP under the control of the early CMV promoter and the bovine growth hormone polyadenylation signal.

Bacterial expression

For bacterial expression, we constructed plasmid pBSGFP (SEQ ID NO:6), a pBSSK+ derivative carrying mwtGFP. pBSGFP was generated by inserting the GFP containing region of pFRED4, digested with BamHII and BamHI and subsequently treated with Klenow, into the EcoRV digested pBSSK+ vector. In pBSGFP the mwtGFP is fused downstream to the 43 amino acids of the alpha peptide of beta galactosidase, present in the pBSSK+ polylinker region. The added amino acids at the N-terminus of mwtGFP have no apparent effect on the GFP signal, as judged from subsequent plasmids containing precise deletions of the extra amino acids.

For GFP overexpression and purification we generated plasmid pFRED13 (SEQ ID NO:7) by ligating the 717 bp fragment from pFRED7 digested with NheI and BamHI, to the 5644 bp fragment resulting from the NheI and BamHI double digestion of pET11a. In pFRED13, GFP is synthesized under the control of the bacteriophage T7 phi10 promoter.

The oligonucleotides used for GFP mutagenesis were synthesized by the DNA Support Services of the ABL Basic Research Program of the National Cancer Institute. DNA sequencing was performed by the PCR-assisted fluorescent terminator method (ReadyReaction DyeDeoxy Terminator Cycle Sequencing Kit, ABI, Columbia, Md.) according to the manufacturer's instructions. Sequencing reactions were resolved on the ABI Model 373A DNA Sequencing System. Sequencing data were analyzed using the Sequencher program (Gene Codes, Ann Arbor, Mich.).

Enzymes were purchased from New England Biolabs (Beverly, Mass.) and used according to conditions described by the supplier. Chemicals used for the purification of wild type and mutant proteins were purchased from SIGMA (St. Louis, Mo.). Tissue culture media were obtained from Biofluids (Rockville, Md.) and GIBCO/BRL (Gaithersburg, Md.). Competent bacterial cells were purchased from GIBCO/BRL.

Preparation of mutants

Initially, plasmid pBSGFP was used to mutagenize the GFP coding sequence by single-stranded DNA site directed mutagenesis, as described by Schwartz et al. (1992) J. Virol. 66:7176. In addition to changing specific codons, our strategy was also to improve GFP expression by replacing potential inhibitory nucleotide sequences without altering the GFP amino acid sequence. This approach has been successfully employed in the past for other proteins (Schwartz et al. (1992) *J. Virol.* 66:7176)

For the pBSGFP mutagenesis the following oligonucleotides were used:

17422 (SEQ ID NO:8):

5'-CAATTTGTGTCCCAGAATGTTGCCATCT-
TCCTTGAAGTCAATACCTTT-3'

17423 (SEQ ID NO:9):

5'-GTCTTGTAGTTGCCGTCATCTTTGAA-
GAAGATGCTCCTTTCCTGTAC-3'

17424 (SEQ ID NO:10):

5'-CATGGAACAGGCAGTTTGCCAGTAGTG-
CAGATGAACTTCAGGGTAAGTTTTC-3'

17425 (SEQ ID NO:11):

5'-CTCCACTGACAGAGAACTTGTGGCCGT-
TAACATCACCATC-3'

17426 (SEQ ID NO:12):

5'-CCATCTTCAATGTTGTGGCGGGTCT-
TGAAGTTCACTTTGATTCCATT-3'

17465 (SEQ ID NO:13):

5'-CGATAAGCTTGAGGATCCTCAGTTGTA-
CAGTTCATCCATGC-3'

Oligonucleotide #17426 introduces a mutation in GFP, converting the Isoleucine (Ile) at position 168 into Threonine (Thr). The Ile168Thr change has been shown to alter the GFP spectrum and to also increase the intensity of GFP fluorescence by almost two-fold at the emission maxima (Heim et al. (1994), supra).

The mutagenesis mixture was used to transform DH5a competent *E. coli* cells. Ampicilin resistant colonies were obtained and examined for their fluorescent properties by excitation with UV light. One colony, significantly brighter than the rest, was apparent on the agar plate. This colony was further purified, the plasmid DNA was isolated and used to transform DH5a competent bacteria. This time all the colonies were bright green when excited with the UV light, indicating that the bright green fluorescence was associated with the presence of the plasmid. The sequence of the GFP segment (SEQ ID NO:14, representing only the segment and not the whole plasmid) of this plasmid, called pBSGFPsg11, was then determined. The sequence analysis revealed that in addition to the designed nucleotide changes, which do no alter the amino acid sequence of GFP, and the Ile168Thr mutation, a second spontaneous mutation had occurred. A thymidine at position 322 of SEQ ID NO:14, which is the GFP-coding region of the pPBSGFPsg11 DNA, was replaced by a cytosine. This nucleotide change converts the phenylalanine (Phe) at position 65 of the GFP amino acid sequence into a leucine (Leu). A series of experiments, which will be described below, demonstrated that indeed the Phe65Leu mutation was responsible for the increase in the intensity of the fluorescent GFP signal.

In subsequent experiments, involving generation of rationally designed GFP mutant combinations to be detailed below, we also used the single-stranded DNA site directed mutagenesis approach. This time, however, the template DNAs were pFRED7 derivatives instead of pBSGFP.

Transfection and expression

The 293 cell line, an adenovirus-transformed human embryonal kidney cell line (Graham et al. (1977), *J. Gen. Virol.* 5:59) was used for protein expression analysis. The cells were cultured in Dulbecco's modified culture medium (DMEM) supplemented with 10% heat-inactivated fetal bovine serum (FBS, Biofluids).

Transfection was performed by the calcium phosphate coprecipitation technique as previously described (Graham et al. (1973), *Virol.* 52:456; Felber et al. (1990), *J. Virol.*

64:3734. Plasmid DNA was purified by Qiagen columns according to the manufacturer's instructions (Qiagen). A mix of 5 to 10 μg of total DNA per ml of final precipitate was overlaid on the cells in 60 mm or 6- and 12-well tissue culture plates (Falcon), using 0.5, 0.25 and 0.125 ml of precipitate, respectively. After overnight incubation, the cells were washed, placed in medium without phenol red and measured in a plate spectrofluorometer, e.g., Cytofluor II (Perceptive Biosystems, Framingham, Mass.)

Purification of wild-type and mutant proteins

E. coli strains carrying pFRED13 or other pET11a derivatives with mutant GFP genes were used for the overproduction and purification of the wt and mutant GFPs or BFPS. The cells were grown in 1 liter LB broth containing 100 μg/ml ampicillin at 32° C. to a density of 0.6–0.8 optical density units at 600 nm. At this point, the cells were induced with 0.6 mM IPTG and incubated for four more hours. Following harvesting of the cell pellets, cellular extracts were prepared as described by Johnson, B. H and Hecht, M. H., 1994, *Biotechnol.* 12: 1357.

GFPs and BFPs were purified from the cellular extracts as follows: Ammonium sulfate (AS) was added first to the extracts (50 g AS per 100 g supernatant) to precipitate the proteins. The precipitants were collected by centrifugation at 7500×g for 15 min and the pellets were dissolved in 5ml of 1 M AS. The samples were then loaded on phenylsepharose column (HR10/10, Pharmacia, Piscataway, N.J.) and washed with 20 mM 2-[N-morpholino]ethanesulfonic Acid (MES) pH 5.6 and 1 M AS. Proteins were eluted with a 45 ml gradient to 20 mM MES, pH 5.6. Fractions containing the GFP or BFP protein were colored even under visible light.

Green or blue-colored fractions were further purified on Q-sepharose (Mono Q, HR5/5, Pharmacia) with a 20 ml gradient from 20 mM Tris pH 7.0 to 20 mM Tris pH 7.0, 0.25 M NaCl.

The AS precipitation step was performed at 4° C. while the chromatographic procedures were performed at room temperature.

Determination of protein concentration

Protein concentrations were determined using the commercially available Bradford protein assay (BioRad, Hercules, Calif.) with bovine IgG protein as a standard.

Analytical polyacrylamide gels

Analytical polyacrylamide gel electrophoresis was used to visualize the degree of purity of the purified GFP or BFP proteins. In all cases, 1 mm thick, 12' acrylamide gels (containing 0.1% SDS, in Tris buffer, pH 7.4) were used, and electrophoresis was performed for 2 hours at 120 V. Gels were stained with Coomassie Blue to visualize the proteins.

Fluorescence measurements

Excitation and emission spectra of solutions of the fluorescent proteins were obtained using a Perkin Elmer L550B spectrofluorimeter (Perkin Elmer, Advanced Biosystems, Foster City,, Calif.).

The relative fluorescence data for the GFP mutants in Table I below were obtained by comparing the cellular fluorescence of the GFP mutants expressed in the transformed human embryonic kidney cell line 293 with mwtGFP expressed in the same cell line. Likewise, the relative fluorescence data for the BFP mutants in Table I below were obtained by comparing the cellular fluorescence of the BFP mutants expressed in 293 cells with BFP(Tyr$_{67}$→His) expressed in the same cell line. Equal amounts of DNA encoding modified wild type or mutant proteins were introduced into 293 cells. Cellular fluorescence was quantified 24 h or 48 hr. post-transfection using Cytofluor II.

A list of GFP mutant proteins indicating the introduced amino acid mutations is shown in Table I.

TABLE I

GFP and BFP mutants

| PROTEIN | Amino Acid Position | | | | | |
|---------|----|----|----|-----|-----|-----|
|         | 65 | 66 | 67 | 164 | 168 | 239 |
| mwt GFP | F  | S  | Y  | V   | I   | K   |
| SG12    | L  |    |    |     |     |     |
| SG11    | L  |    |    |     | T   | N   |
| SG25    | L  | C  |    |     | T   | N   |
| BFP     |    |    | H  |     |     |     |
| SB42    | L  |    | H  |     |     |     |
| SB49    |    |    | H  | A   |     |     |
| SB50    | L  |    | H  | A   |     |     |

EXAMPLE 1

SG12

A number of the unique mutants described herein derive from the discovery of an unplanned and unexpected mutation called "SG12", obtained in the course of site-directed mutagenesis experiments, wherein a phenylalanine at position 65 of mwtGFP was converted to leucine. SG12 was prepared as follows: Two plasmids carrying SG12 (SEQ ID NO:15) were generated, pFRED12 for expression in mammalian cells, and pFRED16 for expression in *E. coli* and protein purification. pFRED12 was constructed by ligating the 1557 bp fragment from the double digestion of pFRED7 with Avr II and Pml I into the 4681 bp fragment generated from the Avr II and Pml I digestion of pFRED11 (see below). pFRED16 was derived by subcloning the 717 bp segment resulting from the digestion of pFRED12 with NheI and BamHI to the 5644 bp fragment of the pET11a vector digested with the same restriction enzymes.

The specific activity of SG12 was about 9–12 times that of mwtGFP. See Table II.

EXAMPLE 2

SG11

A mutant referred to as "SG11," which combined the phenylalanine 65 to leucine alteration with an isoleucine 168 to threonine substitution and a lysine 239 to asparagine susbstitution, gave a further enhanced fluorescence intensity. SG11 was prepared as follows: Two plasmids carrying SG11 (SEQ ID NO:16) were generated: pFRED11 for expression in mammalian cells and pFRED15 for expression in *E. coli* and protein purification. pFRED11 was constructed by ligating the 717 bp region from pBSGFPsg11 DNA digested with NheI and BamHI to the 5221 bp fragment derived from the digestion of pFRED7 with the same enzymes. pFRED15 was generated by subcloning the 717 bp segment resulting from the digestion of pFRED11 with NheI and BamHI to the 5644 bp fragment of the pET11a vector, digested with the same restriction enzymes.

The mutant SG11 encodes an engineered GFP wherein the alteration comprises the conversion of phenylalanine 65 to leucine and the conversion of isoleucine 168 to threonine. The additional alteration of the C-terminal lys 239 to asn is without effect; the C-terminal lys or asn may be deleted without affecting fluorescence. The specific activity of SG11 is about 19–38 times that of mwtGFP. See Table II.

EXAMPLE 3

SG25

A third and further improved GFP mutant was obtained by further mutating "SG11." This mutant is referred to as "SG25" and comprises, in addtion to the SG11 substitutions, and additional substitution of a cysteine for the serine normally found at position 66 in the sequence. SG11 was prepared as follows: Two plasmids carrying SG25 (SEQ ID NO:17) were generated: pFRED25 for expression in mammalian cells and pFRED63 for expression in *E. coli* and protein purification. pFRED25 was constructed by site directed mutagenesis of pFRED11, using oligonucleotide #18217 (SEQ ID NO:18): 5'-CATTGAACACCATAGCAC AGAGTAGTGACTAGTGTTGGCC-3'. This oligonucleotide incorporates the Ser66Cys mutation into SG11. Ser66Cys had been shown to both alter the GFP excitation maxima without significant change in the emission spectrum and to also increase the intensity of the fluorescent signal of GFP (Heim et al., 1995).

pFRED63 was generated by subcloning the 717 bp segment resulting from the digestion of pFRED25 with NheI and BamHI to the 5644 bp fragment of the pET11a vector, digested with the same restriction enzymes.

The mutant SG25 encodes an engineered GFP wherein the alteration comprises the conversion of phenylalanine 65 to leu, the conversion of isoleucine 168 to threonine and the conversion of serine 66 to cysteine. As with SG11, the additional alteration of the C-terminal lysine 239 to asparagine is without effect; the C-terminal lysine or aspragine may be deleted without affecting fluorescence. The specific activity of SG25 is about 56 times that of mwtGFP. See Table II.

EXAMPLE 4
Additional green fluorescent mutants

Additional alterations at different amino acids of the mwtGFP, when combined with SG11 and SG25, yielded proteins having at least 5× greater cellular fluorescence compared to the mwtGFP. A non-limiting list of these mutations is provided below:

GFP variants with enhanced cellular fluorescence

| Protein | Altered Amino Acids |
| --- | --- |
| SG20 | F65L, S66T, I168T, K239N |
| SG21 | F65L, S66A, I168T, K239N |
| SG27 | Y40L, F65L, I168T, K239N |
| SG30 | F47L, F65L, I168T, K239N |
| SG32 | F72L, F65L, I168T, K239N |
| SG43 | F65L, I168T, Y201L, K239N |
| SG46 | F65L, V164A, I168T, K239N |
| SG72 | F65L, S66C, V164A, I168T, K239N |
| SG91 | F65L, S66C, F100L, I168T, K239N |
| SG94 | F65L, S66C, Y107L, I168T, K239N |
| SG95 | F65L, S66C, F115L, I168T, K239N |
| SG96 | F65L, S66C, F131L, I168T, K239N |
| SG98 | F65L, S66C, Y146L, I168T, K239N |
| SG100 | F65L, S66C, Y152L, I168T, K239N |
| SG101 | F65L, S66C, I168T, Y183L, K239N |
| SG102 | F65L, S66C, I168T, F224L, K239N |
| SG103 | F65L, S66C, I168T, Y238L, K239N |
| SG106 | F65L, S66T, V164A, I168T, K239N |

EXAMPLE 5
SB42

The blue fluorescent proteins described here and below were derived from the known GFP mutant (Heim et al., *PNAS*, 1994) wherein histidine is substituted for tyrosine at position 67. We have designated this known mutant BFP (Tyr$_{67}$→His). BFP(Tyr$_{67}$→His) has a shifted emission spectrum. It emits blue light, i.e., it is a blue fluorescent protein (BFP).

By introducing the same mutation in BFP(Tyr$_{67}$→His) that was used to generate SG12, i.e., leucine for phenylalanine at position 65, we created a new mutant that has unexpectedly high fluorescence that we refer to as "SuperBlue-42" (SB42). SB42 was prepared as follows: Two plasmids carrying SB42 (SEQ ID NO:19) were generated: pFRED42 for expression in mammalian cells and pFRED65 for expression in *E. coli* and protein purification. pFRED42 was constructed by site directed mutagenesis of pFRED12, using oligonucleotide #bio25 (5-CATTGAACACCATGAGAGAGAGTAGTGACTAGT GTTGGCC-3') (SEQ ID NO:20). This oligonucleotide incorporates the Tyr$_{67}$→His mutation into SG12, thus generating the Phe65Leu, Tyr$_{67}$→His double mutant.

pFRED65 was created by subcloning the 717 bp segment resulting from the digestion of pFRED42 with NheI and BamHI to the 5644 bp fragment of the pET11a vector, digested with the same restriction enzymes.

The mutant SB42 encodes an engineered BFP wherein the alterations comprise the conversion of tyrosine 67 to histidine and the conversion of phenylalanine 65 to leucine. The specific activity of SB42 is about 27 times that of BFP (Tyr$_{67}$→His). See Table II.

EXAMPLE 6
SB49

An independent mutation of BFP(Tyr$_{67}$→His) which substitutes the valine at position 164 with an alanine is referred to as "SB49." SB49 was prepared as follows: Plasmid pFRED49 expresses SB49 (SEQ ID NO:21) in mammalian cells. pFRED49 was generated by site directed mutagenesis of pFRED12, using oligonucleotides #19059 and #bio24. Oligonucleotide #19059 (5'-CTTCAATGTTGTGGC GGATCTTGAAGTTCGCTTTGATTCCATTC-3') (SEQ ID NO:22) introduces the Val164Ala mutation in SG12 while oligonucleotide #bio24 (5'-CATTGAACACCATGA GAGAAAGTAGTGACTAGTGTTGGCC-3') (SEQ ID NO:23) reverts the Phe65Leu alteration to the wt sequence and, at the same time, incorporates the Tyr$_{67}$→His mutation.

The mutant SB49 encodes an engineered BFP wherein the alterations comprise the conversion of tyrosine 67 to histidine, and the conversion of valine 164 to alanine. The specific activity of SB49 was about 37 times that of BFP (Tyr$_{67}$→His). See Table II.

EXAMPLE 7
SB50

A combination of the above two BFP mutations resulted in "SB50," which gave an even greater fluorescence enhancement than either of the previous mutations. SB50 was prepared as follows: Two plasmids carrying SB50 (SEQ ID NO: 24) were generated: pFRED50 for expression in mammalian cells and pFRED67 for expression in *E. coli* and protein purification. pFRED50 was constructed by site directed mutagenesis of pFRED12, using oligonucleotides #19059 and #bio25.

pFRED67 was created by subcloning the 717 bp segment resulting from the digestion of pFRED50 with NheI and BamHI to the 5644 bp fragment of the pET11a vector digested with the same restriction enzymes.

The mutant SB50 encodes an engineered BFP wherein the alterations comprise the conversion of tyrosine 7 to histidine, the conversion of phenylalanine 65 to leucine and the conversion of alanine 164 to valine. The specific activity of SB50 was about 63 times that of BFP(Tyr$_{67}$→His) See Table II.

TABLE II

| Mutant | Excitation Maximum (nm) | Emission Maximum (nm) | Factor of increased green fluorescence (at maximum emission) as compared to mwt.GFP | Factor of increased blue fluorescence (at maximum emission) as compared to BFP (Tyr$_{67}$→His) |
|---|---|---|---|---|
| SG12 | 398 | 509 | 9–12X | |
| SG11 | 471 | 508 | 19–38X | |
| SG25 | 473 | 509 | 50–100X | |
| SB42 | 387 | 450 | | 27X |
| SB49 | 387 | 450 | | 37X |
| SB50 | 387 | 450 | | 63X |

The dramatic increase in fluorescent activity resulting from the amino acid substitutions of the present invention was wholly unexpected. The cellular fluorescence of the mutants was at least five times greater, and usually over twenty times greater, than that of the parent mwtGFP or BFP(Tyr$_{67}$→His). Note that the maximum emission wavelengths vary among the mutants, and that the above-reported fold increases refer only to minimal increases in relative cellular fluorescence at the maximum emission wavelength of the mutant. Given a particular wavelength, the values may be substantially larger, i.e., the mutants may have a 200-fold greater cellular fluorescence than the reference mwtGFP or BFP(Tyr$_{67}$→His). This is important because devices for measuring fluorescence often have set wavelengths, or the limitations of a given experiment often require the use of a set wavelength. Thus, for example, the emission and detection parameters of a fluorescence microscope or a fluorescence-activated cell sorter may be set for a wavelength wherein the cellular fluorescence of a given mutant is 200-fold greater than that of the known GFPs and BFPS.

The GFP and BFP mutants of this invention, in contrast to the wild type protein or other reported mutants, allow detection of green fluorescence in living mammalian cells when present in few copies stably integrated into the genome. This high cellular fluorescence of the mutant GFPs and BFPs is useful for rapid and simple detection of gene expression in living cells and tissues and for repeated analysis of gene expression over time under a variety of conditions. They are also useful for the construction of stable marked cell lines that can be quickly identified by fluorescence microscopy or fluorescence activated cell sorting.

EXAMPLE 8

We have established fluoroplate-based assays for the quantitation of gene expression after transfections. In a number of embodiments, a nucleic acid encoding a mutant GFP or BFP of this invention is inserted into a vector and introduced into and expressed in a cell. Typically, expression of GFP mutants can be detected as quickly as 5 hours post-infection or less. Expression is followed over time in living cells by a simple measurement in multi-well plates. In this way, many transfections can be processed in parallel.

EXAMPLE 9

The vectors and nucleic acids provided herein are used to generate chimeric proteins wherein a nucleic acid sequence that encodes a selected gene product is fused to the C- or N-terminus of the mutant GFPs and/or BFPs of this invention. A number of unique viral, plasmid and hybrid gene constructs have been generated that incorporate the new mutant GFP and/or mutant BFP sequences indicated above. These include:

HIV viral sequences (in the nef gene) containing SG11 or SG25

Neomycin & hygromycin plasmids containing SG11 or SG25

Moloney Leukemia Virus vector (retrovirus) also expressing SG25

Hybrid gene constructs expressing HIV viral proteins (rev, td-rev, tat, nef, gag, env, and vpr) and either SG11 or SG25 or SB50.

Hybrid gene construct containing vectors that incorporate the cytoplasmic proteins ran, B23, nucleolin, poly-A binding protein and either SG11 or SG25 or SB50.

These hybrids of the mutant nucleic acids provided herein are used to study protein trafficking in living mammalian cells. Like the wild type GFP, the mutant GFP proteins are normally distributed throughout the cell except for the nucleolus. Fusions to other proteins redistribute the fluorescence, depending on the partner in the hybrid. For example, fusion with the entire HIV-1 Rev protein results in a hybrid molecule which retains the Rev function and is localized in the nucleolus where Rev is preferentially found. Fusion to the N-terminal domain of the HIV-1 Nef protein created a chimeric protein detected in the plasma membrane, the site of Nef localization.

EXAMPLE 10 pCMVgfo11 pCMVgfo11 is a pFRED11 derivative containing the bacterial neomycin phosphotransferase gene (neo) (Southern and Berg (1982) *J. Mol. Appl. Genetics* 1:327) fused at the C-terminus of SG11. A four amino acid (Gly-Ala-Gly-Ala) (SEQ ID NO:26) linker region connects the last amino acid of SG11 to the second amino acid of neo, thus generating the hybrid SG11-neo protein (gfo11, SEQ ID NO:25). Gfo11 is expressed from the CMV promoter and contains the intact SG11 polypeptide and all of neo except for the first Met. pCMVgfo11 was constructed in several steps. First, pFRED11DNae was constructed by NaeI digestion of pFRED11 and self-ligation of the 4613 bp fragment. The NaeI deletion removes the SV40 promoter and neo gene from pFRED11, thus creating pFRED11DNae. Next, in order to fuse the neo coding region downstream to SG11, the neo gene was PCR amplified from pcDNA3 using primers Bio51 (5'-CGCGGATCCTTCGAACAAGATGGATTGCACGC-3') (SEQ ID NO:27) and Bio52 (5-CCGGAATTCTCAGAAGAACTCGTCAAGAAGGCGA-3') (SEQ ID NO:28). Primer Bio51 introduces a BamHI site followed by a BstBI recognition sequence at the 5' end of neo, while primer Bio52 introduces an EcoRI site 3' to the neo gene. The PCR product was digested with BamHI and EcoRI and cloned into the 4582 bp vector resulting from the BamHI-EcoRI digestion of pFRED11DNae, thus generating pFRED11DNaeBstNeo. Subsequently, SG11 was PCR amplified from pFRED11DNae using primers Bio49 (5'-GGCGCGCAAGAAATGGCTAGCAAAGGAGAAGAACTCTTCACTGGAG-3') (SEQ ID NO:29) and Bio50 (5'-CCCATCGATAGCACCAGCACCGTTGTACAGTTCATCCATGCCATGT-3') (SEQ ID NO:30) to remove the sgII stop codon in pFRED11DNaeBstNeo and to introduce the four amino acid (Gly-Ala-Gly-Ala) linker followed by a ClaI site. The PCR product was digested with NheI and ClaI and cloned into the 4763 bp NhelBstBi fragment from pFRED11DNaeBstNeo, thus generating pCMVgfo11.

Following transfection of 293 cells (Graham et al. (1977), *J. Gen. Virol.* 5:59) as well as other human and mouse cell lines with pCMVgfo11, bright fluorescent transfectants were apparent under the flourescent microscope and colonies resistant to G418 could be obtained two weeks later.

It should be noted that pCMVgfo11 was the best protein fusion in terms of fluorescent emission intensity and number of G418 resistant colonies compared to several SG11-neo or neo-SG11 fusions generated and examined.

EXAMPLE 11
pPGKgfo25 pPGKgfo25 is a pCMVgfoII derivative containing SG25 instead of SG11 within gfo (SEQ ID NO: 31). Expression of gfo25 in pPGKgfo25 is under the control of the mouse phosphoglycerate kinase-1 (PGK) promoter.

pPGKgfo25 was constructed in several steps. First, a SacII site was introduced downstream of the PGK promoter in pPGKneobpA (Soriano et al. (1991) Cell: 64–393) by:

i) annealing oligonucleotides #18990 (SEQ ID NO:32) (5'-GACCGGGACACGTATCCAGCCTCCGC-3') and 18991 (SEQ ID NO:33) (5'-GGAGGCTGGATACGTGTCCCGGTCTGCA-3') to create a double stranded adapter for PstI at the 5' end and SacII at the 3' end.

ii) ligating this adapter to the 3423 bp fragment from the PstI-SacII double digestion of pPGKneobpA, thus generating pPGKPtAfSc.

Next, the CMV promoter of pFRED25 was replaced with the PGK promoter by cloning the 565 bp SalI (filled with Klenow)-SacII region from pPGKPtAfSc to the 5288 bp BglII (filled with Klenow)-SacII fragment from pFRED25, resulting in pFRED25PGK. In the final step, pPGKgfo25 was constructed by ligating the 813 bp BglII-NdeI fragment from pFRED25PGK containing the PGK promoter and SG25, to the 4185 bp BglII-NdeI fragment of pCMVgfo11.

EXAMPLE 12
pGen-PGKgfo25RO (SEQ ID NO: 34)

pGen-PGKgfo25RO is a pGen- (Soriano et al. (1991), *J. Virol.* 65:2314) derivative containing the gfo25 hybrid under the control of PGK promoter. It was constructed by subcloning the 2810 bp SalI fragment of pPGKgfo25 into the XhoI site of pGen. In viruses generated from pGen-PGKgfo25RO (see below) transcription originated from the PGK promoter is in reverse orientation (RO) to that initiated from the viral long terminal repeats (LTR).

To generate ecotropic or pseudotyped viruses, pGen-PGKgfo25RO was co-transfected into 293 cells together with pHIT60 and pHIT123 DNAs (production of ecotropic virus) or with pHIT60 and pHCMV-G DNAs (production of pseudotyped virus). pHIT60 and pHIT123 contain the gag-pol and env coding regions from the Moloney murine leukemia virus (Mo-MLV) respectively, under the control of the CMV promoter (Soneoka et al. (1995), *Nuc. Acid Res.* 23:628. pHCMV-G contains the coding region of the G protein from the vesicular stomatitis virus (VSV) expressed from the CMV promoter (Yee et al. (1994), *Proc. Nat'l Acad. Sci. USA* 91:9564. Virus-containing supernatants were harvested 48 hours post transfection, filtered and stored at −80° C.

EXAMPLE 13
pNLnSG11 (SEQ ID NO:35)

The SG11 sequence from plasmid pFRED11 was PCR-amplified with primers #17982 (SEQ ID NO:36) (5'-GGGGCGTACGGAGCGCTCCGAATTCGG-TACCGTTTAAACGGGCCCTCTCGAGTCC GTTGTACAGTTCATCCATG-3') and #17983 (SEQ ID NO:37) (5'-GGGGGAATTCGCGCGCGTACG-TAAGCGCTAGCTGAGCAAGAAATGGCTAGCAAA GGAGAAGAACTC-3'). The PCR product was digested with BlpI and XhoI and cloned into the large BlpI-XhoI fragment from pNL4-3 (Adachi et al. (1986), *J. Virol.* 59: 284. In pNLnSG11 the full SG11 polypeptide containing an additional four linker-encoded amino acids at the C-terminus, is expressed as a hybrid protein with the 24 N-terminal amino acids of the HIV-1 protein Nef.

We constructed transmissible HIV-1 stocks with our mutants, which generate green fluorescence upon transfection of human cells. These transmissible HIV-1 stocks are used to detect the kinetics of infection under a variety of conditions. In particular, they are used to study the effects of drugs on the kinetics of infection. The level of fluorescence, and the subcellular compartmentalization of that fluorescence, is easily visualized and quantified using well known methods. This system is easy to visualize, and dramatically cuts the costs of many experiments that are presently tedious and expensive.

To produce infectious virus, pNLnSG11 was transfected in 293 cells. 24 hours later, Jurkat cells were added to the transfectants. At various times post-infection, the medium was removed, filtered, and used to infect fresh Jurkat or other HIV-1-permissive cells. Two days later the infected cells were green under fluorescent microscope. Visible syncytia were also green. Viral stocks were generated and kept at −80° C.

When the nucleic acids, vectors, mutant proteins provided herein are combined with the knowledge of those skilled in the art of genetic engineering and the guidance provided herein, it will be apparent to one of ordinary skill in the art that many changes and modifications can be made thereto without departing from the spirit or scope of the invention as set forth herein. These changes and modifications are encompassed by the present invention.

What is claimed is:

1. An isolated nucleic acid that encodes an engineered *Aequorea victoria* fluorescent protein, wherein the protein encoded by the isolated nucleic acid is selected from the group that consists of proteins wherein one or more amino acid residues of a protein having an amino acid sequence set forth in SEQ ID NO:2 are substituted to produce:
   a. a singly-substituted protein that has leucine at amino acid position 65, and wherein said protein has a cellular fluorescence that is at least about ten times greater than the cellular fluorescence of a protein having the amino acid sequence set forth in SEQ ID NO:2;
   b. a protein that has leucine at amino acid position 65 and threonine at position 168, and wherein said protein has a cellular fluorescence that is at least about ten times greater than a protein having the amino acid sequence set forth in SEQ ID NO:2;
   c. a protein that has leucine at amino acid position 65, threonine at position 168, and cysteine at position 66, wherein said protein has a cellular fluorescence that is at least about ten times greater than the cellular fluorescence of a protein having the amino acid sequence set forth in SEQ ID NO:2;
   d. a blue fluorescent protein (BFP) that has histidine at amino acid position 67, leucine at position 65 and has a cellular fluorescence that is at least five times greater than that of BFP(Tyr$_{67}$→His);
   e. a blue fluorescent protein that has histidine at amino acid position 67, alanine at amino acid position 164 and has a cellular fluorescence that is at least five times greater than that of BFP(Tyr$_{67}$→His);
   f. a blue fluorescent protein that has histidine at amino acid position 67, leucine at amino acid position 65, alanine at amino acid position 164 and has a cellular fluorescence that is at least five times greater than that of BFP(Tyr$_{67}$→His).

2. An isolated nucleic acid of claim 1, which encodes an engineered *Aequorea victoria* green fluorescent protein (GFP) having a cellular fluorescence that is at least about ten times greater than that of the protein having the amino acid sequence set forth in SEQ ID NO:2, wherein the engineered GFP has a leucine at amino acid position 65.

3. An isolated nucleic acid according to claim 1 which encodes an engineered *Aequorea victoria* green fluorescent protein (GFP) having a cellular fluorescence that is at least about ten times greater than that of the protein having the amino acid sequence set forth in SEQ ID NO:2, wherein the engineered GFP has a leucine at amino acid position 65 and a threonine at amino acid position 168.

4. An isolated nucleic acid according to claim 3, wherein the nucleic acid further encodes a cysteine at amino acid position 66.

5. An isolated nucleic acid of claim 1 that encodes an engineered blue fluorescent protein BFP that has histidine at amino acid position 67 and leucine at position 65, and has a cellular fluorescence that is at least five times greater than that of BFP(Tyr$_{67}$→His).

6. An isolated nucleic acid of claim 1 that encodes an engineered blue fluorescent protein (BFP) that has histidine at amino acid position 67 and alanine at amino acid position 164, and has a cellular fluorescence that is at least five times greater than that of BFP(Tyr$_{67}$→His).

7. An isolated nucleic acid according to claim 6, wherein the nucleic acid further encodes leucine at amino acid position 65.

8. A transformed cell that expresses a protein encoded by a nucleic acid of claim 1.

9. A vector comprising a nucleic acid of claim 1.

10. A transformed cell comprising a vector of claim 9.

11. A transformed cell that expresses a protein encoded by the nucleic acid of claim 1 fused to a protein encoded by a second nucleic acid of interest.

12. A method of detecting and optionally isolating an engineered cell that contains a first selected nucleic acid and a second selected nucleic acid, comprising:
   a) stably introducing into a host cell in a population of host cells a vector that contains a first nucleic acid selected from the group consisting of nucleic acids that encode SG11, SG12, SG25, SB42, SB49, and SB50, and a second nucleic acid which encodes a selected protein or a nucleic acid regulatory sequence, and
   b) detecting cells in the population of host cells that express SG11, SG12, SG25, SB42, SB49, or SB50, and
   c) optionally sorting cells that express SG11, SG12, SG25, SB42, SB49, or SB50 with a fluorescence-activated cell sorter to isolate individual cells that express said fluorescent protein.

13. A nucleic acid construct wherein a coding sequence selected from the group consisting of nucleic acids that encode SG11, SG12, SG25, SB42, SB49, and SB50 is operably linked to a regulatory sequence of a selected gene.

14. A nucleic acid construct wherein a first coding sequence that encodes a selected polypeptide is fused using genetic engineering to a second coding sequence selected from the group consisting of nucleic acids that encode SG11, SG12, SG25, SB42, SB49, and SB50, such that expression of the fused sequence yields a fluorescent hybrid protein in which the polypeptide encoded by the first coding sequence is fused to the polypeptide encoded by the second coding sequence.

15. A method of detecting and characterizing regulatory and coding sequence elements that regulate subcellular expression and targeting of proteins, comprising:
   a) expressing in an engineered cell, in the presence and absence of selected culture conditions and components, a nucleic acid wherein a first nucleic acid selected from the group consisting nucleic acids that encode SG11, SG12, SG25, SB42, SB49, and SB50 is operably linked to a second nucleic acid derived from a selected gene;
   b) detecting the presence and subcellular localization of fluorescent signal.

16. A method according to claim 12, wherein said nucleic acid that encodes SG11 has the nucleic acid sequence set forth in SEQ ID NO:15, said nucleic acid that encodes SG12 has the nucleic acid sequence set forth in SEQ ID NO:16, said nucleic acid that encodes SG25 has the nucleic acid sequence set forth in SEQ ID NO: 17, said nucleic acid that encodes SB42 has the nucleic acid sequence set forth in SEQ ID NO: 19, said nucleic acid that encodes SB49 has the nucleic acid sequence set forth in SEQ ID NO:21, and said nucleic acid that encodes SB50 has the nucleic acid sequence set forth in SEQ ID NO:24.

17. A nucleic acid construct according to claim 13, wherein said nucleic acid that encodes SG11 has the nucleic acid sequence set forth in SEQ ID NO:15, said nucleic acid that encodes SG12 has the nucleic acid sequence set forth in SEQ ID NO: 16, said nucleic acid that encodes SG25 has the nucleic acid sequence set forth in SEQ ID NO:17, said nucleic acid that encodes SB42 has the nucleic acid sequence set forth in SEQ ID NO: 19, said nucleic acid that encodes SB49 has the nucleic acid sequence set forth in SEQ ID NO:21, and said nucleic acid that encodes SB50 has the nucleic acid sequence set forth in SEQ ID NO:24.

18. A nucleic acid construct according to claim 14, wherein said nucleic acid that encodes SG11 has the nucleic acid sequence set forth in SEQ ID NO:15, said nucleic acid that encodes SG12 has the nucleic acid sequence set forth in SEQ ID NO: 16, said nucleic acid that encodes SG25 has the nucleic acid sequence set forth in SEQ ID NO: 17, said nucleic acid that encodes SB42 has the nucleic acid sequence set forth in SEQ ID NO: 19, said nucleic acid that encodes SB49 has the nucleic acid sequence set forth in SEQ ID NO:21, and said nucleic acid that encodes SB50 has the nucleic acid sequence set forth in SEQ ID NO:24.

19. A method according to claim 15, wherein said nucleic acid that encodes SG11 has the nucleic acid sequence set forth in SEQ ID NO:15, said nucleic acid that encodes SG12 has the nucleic acid sequence set forth in SEQ ID NO:16, said nucleic acid that encodes SG25 has the nucleic acid sequence set forth in SEQ ID NO:17, said nucleic acid that encodes SB42 has the nucleic acid sequence set forth in SEQ ID NO:19, said nucleic acid that encodes SB49 has the nucleic acid sequence set forth in SEQ ID NO:21, and said nucleic acid that encodes SB50 has the nucleic acid sequence set forth in SEQ ID NO:24.

20. An isolated nucleic acid of claim 1, which encodes an engineered *Aequorea victoria* green fluorescent protein (GFP) having a cellular fluorescence that is at least about twenty times greater than that of the protein having the amino acid sequence set forth in SEQ ID NO:2.

21. An isolated nucleic acid of claim 1 which encodes an engineered GFP having a cellular fluorescence that is at least about ten times greater than that of the protein having the amino acid sequence set forth in SEQ ID NO:2 wherein said protein is selected from the group consisting of: SG12 (F65L), SG11 (F65L, I168T, K239N), SG25 (F65L, S66C, I168T, K239N), SG30 (F47L, F65L, I168T, K239N), SG32 (F65L, F72L, I168T, K239N), SG43 (F65L, I168T, Y201L, K239N), SG46 (F65L, V164A, I168T, K239N), SG72 (F65L, S66C, V164A, I168T, K239N), SG91 (F65L, S66C, F100L, I168T, K239N), SG94 (F65L, S66C, Y107L, I168T, K239N), SG95 (F65L, S66C, F115L, I168T, K239N), SG96 (F65L, S66C, F131L, I168T, K239N), SG98 (F65L, S66C, Y146L, I168T, K239N), SG100 (F65L, S66C, Y152L, I168T, K239N), SG101 (F65L, S66C, I168T Y183L, K239N), SG102 (65L, S66C, I168T, F224L, K239N), SG103 (F65L, S66C, I168T, Y238L, K239N), and SG106 (F65L, S66T, V164A, I168T, K239N).

\* \* \* \* \*

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:

(A) LENGTH: 720 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..720
        (D) OTHER INFORMATION: /product= "wild type Aequorea victoria
            Green Fluorescent Protein (wtGF)"

(xi) SEQUENCE DESCRIPTION: SEQ ID NO:1:

```
ATG GCT AGC AAA GGA GAA GAA CTC TTC ACT GGA GTT GTC CCA ATT CTT        48
Met Ala Ser Lys Gly Glu Glu Leu Phe Thr Gly Val Val Pro Ile Leu
 1               5                  10                  15

GTT GAA TTA GAT GGT GAT GTT AAT GGG CAC AAA TTT TCT GTC AGT GGA        96
Val Glu Leu Asp Gly Asp Val Asn Gly His Lys Phe Ser Val Ser Gly
                20                  25                  30

GAG GGT GAA GGT GAT GCA ACA TAC GGA AAA CTT ACC CTT AAA TTT ATT       144
Glu Gly Glu Gly Asp Ala Thr Tyr Gly Lys Leu Thr Leu Lys Phe Ile
        35                  40                  45

TGC ACT ACT GGA AAA CTA CCT GTT CCA TGG CCA ACA CTT GTC ACT ACT       192
Cys Thr Thr Gly Lys Leu Pro Val Pro Trp Pro Thr Leu Val Thr Thr
50                  55                  60

TTC TCT TAT GGT GTT CAA TGC TTT TCA AGA TAC CCG GAT CAT ATG AAA       240
Phe Ser Tyr Gly Val Gln Cys Phe Ser Arg Tyr Pro Asp His Met Lys
65                  70                  75                  80

CGG CAT GAC TTT TTC AAG AGT GCC ATG CCC GAA GGT TAT GTA CAG GAA       288
Arg His Asp Phe Phe Lys Ser Ala Met Pro Glu Gly Tyr Val Gln Glu
                85                  90                  95

AGA ACT ATA TTT TTC AAA GAT GAC GGG AAC TAC AAG ACA CGT GCT GAA       336
Arg Thr Ile Phe Phe Lys Asp Asp Gly Asn Tyr Lys Thr Arg Ala Glu
            100                 105                 110

GTC AAG TTT GAA GGT GAT ACC CTT GTT AAT AGA ATC GAG TTA AAA GGT       384
Val Lys Phe Glu Gly Asp Thr Leu Val Asn Arg Ile Glu Leu Lys Gly
        115                 120                 125

ATT GAT TTT AAA GAA GAT GGA AAC ATT CTT GGA CAC AAA TTG GAA TAC       432
Ile Asp Phe Lys Glu Asp Gly Asn Ile Leu Gly His Lys Leu Glu Tyr
    130                 135                 140

AAC TAT AAC TCA CAC AAT GTA TAC ATC ATG GCA GAC AAA CAA AAG AAT       480
Asn Tyr Asn Ser His Asn Val Tyr Ile Met Ala Asp Lys Gln Lys Asn
145                 150                 155                 160

GGA ATC AAA GTT AAC TTC AAA ATT AGA CAC AAC ATT GAA GAT GGA AGC       528
Gly Ile Lys Val Asn Phe Lys Ile Arg His Asn Ile Glu Asp Gly Ser
                165                 170                 175

GTT CAA CTA GCA GAC CAT TAT CAA CAA AAT ACT CCA ATT GGC GAT GGC       576
Val Gln Leu Ala Asp His Tyr Gln Gln Asn Thr Pro Ile Gly Asp Gly
            180                 185                 190

CCT GTC CTT TTA CCA GAC AAC CAT TAC CTG TCC ACA CAA TCT GCC CTT       624
Pro Val Leu Leu Pro Asp Asn His Tyr Leu Ser Thr Gln Ser Ala Leu
        195                 200                 205

TCG AAA GAT CCC AAC GAA AAG AGA GAC CAC ATG GTC CTT CTT GAG TTT       672
Ser Lys Asp Pro Asn Glu Lys Arg Asp His Met Val Leu Leu Glu Phe
    210                 215                 220

GTA ACA GCT GCT GGG ATT ACA CAT GGC ATG GAT GAA CTA TAC AAA TAA       720
Val Thr Ala Ala Gly Ile Thr His Gly Met Asp Glu Leu Tyr Lys *
225                 230                 235                 240
```

(2) INFORMATION FOR SEQ ID NO:2:

(i) SEQUENCE CHARACTERISTICS:

(A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..35
        (D) OTHER INFORMATION: /note= "oligonucleotide sense primer
            #16417"

(xi) SEQUENCE DESCRIPTION: SEQ ID NO:3:

GGAGGCGCGC AAGAAATGGC TAGCAAAGGA GAAGA                                    35

(2) INFORMATION FOR SEQ ID NO:4:

(i) SEQUENCE CHARACTERISTICS:
        (A) LENGTH: 36 base pairs (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..36
            (D) OTHER INFORMATION: /note= "oligonucleotide antisense
                primer #16418"

(xi) SEQUENCE DESCRIPTION: SEQ ID NO:4:

GCGGGATCCT TATTTGTATA GTTCATCCAT GCCATG                                    36

(2) INFORMATION FOR SEQ ID NO:5:

(i) SEQUENCE CHARACTERISTICS:
            (A) LENGTH: 6238 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..6238
            (D) OTHER INFORMATION: /note= "pFRED7"

(xi) SEQUENCE DESCRIPTION: SEQ ID NO:5:

GACGGATCGG GAGATCTCCC GATCCCCTAT GGTCGACTCT CAGTACAATC TGCTCTGATG          60

CCGCATAGTT AAGCCAGTAT CTGCTCCCTG CTTGTGTGTT GGAGGTCGCT GAGTAGTGCG         120

CGAGCAAAAT TTAAGCTACA ACAAGGCAAG GCTTGACCGA CAATTGCATG AAGAATCTGC         180

TTAGGGTTAG GCGTTTTGCG CTGCTTCGCC TCGAGGCCTG GCCATTGCAT ACGTTGTATC         240

CATATCATAA TATGTACATT TATATTGGCT CATGTCCAAC ATTACCGCCA TGTTGACATT         300

GATTATTGAC TAGTTATTAA TAGTAATCAA TTACGGGGTC ATTAGTTCAT AGCCCATATA         360

TGGAGTTCCG CGTTACATAA CTTACGGTAA ATGGCCCGCC TGGCTGACCG CCCAACGACC         420

CCCGCCCATT GACGTCAATA ATGACGTATG TTCCCATAGT AACGCCAATA GGGACTTTCC         480

ATTGACGTCA ATGGGTGGAG TATTTACGGT AAACTGCCCA CTTGGCAGTA CATCAAGTGT         540

ATCATATGCC AAGTACGCCC CCTATTGACG TCAATGACGG TAAATGGCCC GCCTGGCATT         600

ATGCCCAGTA CATGACCTTA TGGGACTTTC CTACTTGGCA GTACATCTAC GTATTAGTCA         660

TCGCTATTAC CATGGTGATG CGGTTTTGGC AGTACATCAA TGGGCGTGGA TAGCGGTTTG         720

ACTCACGGGG ATTTCCAAGT CTCCACCCCA TTGACGTCAA TGGGAGTTTG TTTTGGCACC         780

AAAATCAACG GGACTTTCCA AAATGTCGTA ACAACTCCGC CCCATTGACG CAAATGGGCG         840

GTAGGCGTGT ACGGTGGGAG GTCTATATAA GCAGAGCTCG TTTAGTGAAC CGTCAGATCG         900

CCTGGAGACG CCATCCACGC TGTTTTGACC TCCATAGAAG ACACCGGGAC CGATCCAGCC         960

TCCGCGGGCG CGCAAGAAAT GGCTAGCAAA GGAGAAGAAC TCTTCACTGG AGTTGTCCCA        1020

ATTCTTGTTG AATTAGATGG TGATGTTAAT GGGCACAAAT TTTCTGTCAG TGGAGAGGGT        1080

GAAGGTGATG CAACATACGG AAAACTTACC CTTAAATTTA TTTGCACTAC TGGAAAACTA        1140

CCTGTTCCAT GGCCAACACT TGTCACTACT TTCTCTTATG GTGTTCAATG CTTTTCAAGA        1200

TACCCGGATC ATATGAAACG GCATGACTTT TTCAAGAGTG CCATGCCCGA AGGTTATGTA        1260

CAGGAAAGAA CTATATTTTT CAAAGATGAC GGGAACTACA AGACACGTGC TGAAGTCAAG        1320

TTTGAAGGTG ATACCCTTGT TAATAGAATC GAGTTAAAAG GTATTGATTT TAAAGAAGAT        1380

```
GGAAACATTC TTGGACACAA ATTGGAATAC AACTATAACT CACACAATGT ATACATCATG    1440

GCAGACAAAC AAAAGAATGG AATCAAAGTT AACTTCAAAA TTAGACACAA CATTGAAGAT    1500

GGAAGCGTTC AACTAGCAGA CCATTATCAA CAAAATACTC CAATTGGCGA TGGCCCTGTC    1560

CTTTTACCAG ACAACCATTA CCTGTCCACA CAATCTGCCC TTTCGAAAGA TCCCAACGAA    1620

AAGAGAGACC ACATGGTCCT TCTTGAGTTT GTAACAGCTG CTGGGATTAC ACATGGCATG    1680

GATGAACTAT ACAAATAAGG ATCCACTAGT AACGGCCGCC AGTGTGCTGG AATTCTGCAG    1740

ATATCCATCA CACTGGCGGC CGCTCGAGCA TGCATCTAGA GGGCCCTATT CTATAGTGTC    1800

ACCTAAATGC TAGAGCTCGC TGATCAGCCT CGACTGTGCC TTCTAGTTGC CAGCCATCTG    1860

TTGTTTGCCC CTCCCCCGTG CCTTCCTTGA CCCTGGAAGG TGCCACTCCC ACTGTCCTTT    1920

CCTAATAAAA TGAGGAAATT GCATCGCATT GTCTGAGTAG GTGTCATTCT ATTCTGGGGG    1980

GTGGGGTGGG GCAGGACAGC AAGGGGGAGG ATTGGGAAGA CAATAGCAGG CATGCTGGGG    2040

ATGCGGTGGG CTCTATGGCT TCTGAGGCGG AAAGAACCAG CTGGGGCTCT AGGGGGTATC    2100

CCCACGCGCC CTGTAGCGGC GCATTAAGCG CGGCGGGTGT GGTGGTTACG CGCAGCGTGA    2160

CCGCTACACT TGCCAGCGCC CTAGCGCCCG CTCCTTTCGC TTTCTTCCCT TCCTTTCTCG    2220

CCACGTTCGC CGGCTTTCCC CGTCAAGCTC TAAATCGGGG CATCCCTTTA GGGTTCCGAT    2280

TTAGTGCTTT ACGGCACCTC GACCCCAAAA AACTTGATTA GGGTGATGGT TCACGTAGTG    2340

GGCCATCGCC CTGATAGACG GTTTTTCGCC CTTTGACGTT GGAGTCCACG TTCTTTAATA    2400

GTGGACTCTT GTTCCAAACT GGAACAACAC TCAACCCTAT CTCGGTCTAT TCTTTTGATT    2460

TATAAGGGAT TTTGGGGATT TCGGCCTATT GGTTAAAAAA TGAGCTGATT TAACAAAAAT    2520

TTAACGCGAA TTAATTCTGT GGAATGTGTG TCAGTTAGGG TGTGGAAAGT CCCCAGGCTC    2580

CCCAGGCAGG CAGAAGTATG CAAAGCATGC ATCTCAATTA GTCAGCAACC AGGTGTGGAA    2640

AGTCCCCAGG CTCCCCAGCA GGCAGAAGTA TGCAAAGCAT GCATCTCAAT TAGTCAGCAA    2700

CCATAGTCCC GCCCCTAACT CCGCCCATCC CGCCCCTAAC TCCGCCCAGT TCCGCCCATT    2760

CTCCGCCCCA TGGCTGACTA ATTTTTTTTA TTTATGCAGA GGCCGAGGCC GCCTCTGCCT    2820

CTGAGCTATT CCAGAAGTAG TGAGGAGGCT TTTTTGGAGG CCTAGGCTTT TGCAAAAAGC    2880

TCCCGGGAGC TTGTATATCC ATTTTCGGAT CTGATCAAGA GACAGGATGA GGATCGTTTC    2940

GCATGATTGA ACAAGATGGA TTGCACGCAG GTTCTCCGGC CGCTTGGGTG GAGAGGCTAT    3000

TCGGCTATGA CTGGGCACAA CAGACAATCG GCTGCTCTGA TGCCGCCGTG TTCCGGCTGT    3060

CAGCGCAGGG GCGCCCGGTT CTTTTTGTCA AGACCGACCT GTCCGGTGCC CTGAATGAAC    3120

TGCAGGACGA GGCAGCGCGG CTATCGTGGC TGGCCACGAC GGGCGTTCCT TGCGCAGCTG    3180

TGCTCGACGT TGTCACTGAA GCGGGAAGGG ACTGGCTGCT ATTGGGCGAA GTGCCGGGGC    3240

AGGATCTCCT GTCATCTCAC CTTGCTCCTG CCGAGAAAGT ATCCATCATG GCTGATGCAA    3300

TGCGGCGGCT GCATACGCTT GATCCGGCTA CCTGCCCATT CGACCACCAA GCGAAACATC    3360

GCATCGAGCG AGCACGTACT CGGATGGAAG CCGGTCTTGT CGATCAGGAT GATCTGGACG    3420

AAGAGCATCA GGGGCTCGCG CCAGCCGAAC TGTTCGCCAG GCTCAAGGCG CGCATGCCCG    3480

ACGGCGAGGA TCTCGTCGTG ACCCATGGCG ATGCCTGCTT GCCGAATATC ATGGTGGAAA    3540

ATGGCCGCTT TTCTGGATTC ATCGACTGTG GCCGGCTGGG TGTGGCGGAC CGCTATCAGG    3600

ACATAGCGTT GGCTACCCGT GATATTGCTG AAGAGCTTGG CGGCGAATGG GCTGACCGCT    3660

TCCTCGTGCT TTACGGTATC GCCGCTCCCG ATTCGCAGCG CATCGCCTTC TATCGCCTTC    3720
```

-continued

```
TTGACGAGTT CTTCTGAGCG GGACTCTGGG GTTCGAAATG ACCGACCAAG CGACGCCCAA    3780

CCTGCCATCA CGAGATTTCG ATTCCACCGC CGCCTTCTAT GAAAGGTTGG GCTTCGGAAT    3840

CGTTTTCCGG GACGCCGGCT GGATGATCCT CCAGCGCGGG GATCTCATGC TGGAGTTCTT    3900

CGCCCACCCC AACTTGTTTA TTGCAGCTTA TAATGGTTAC AAATAAAGCA ATAGCATCAC    3960

AAATTTCACA ATAAAGCAT TTTTTTCACT GCATTCTAGT TGTGGTTTGT CCAAACTCAT     4020

CAATGTATCT TATCATGTCT GTATACCGTC GACCTCTAGC TAGAGCTTGG CGTAATCATG    4080

GTCATAGCTG TTTCCTGTGT GAAATTGTTA TCCGCTCACA ATTCCACACA ACATACGAGC    4140

CGGAAGCATA AAGTGTAAAG CCTGGGGTGC CTAATGAGTG AGCTAACTCA CATTAATTGC    4200

GTTGCGCTCA CTGCCCGCTT TCCAGTCGGG AAACCTGTCG TGCCAGCTGC ATTAATGAAT    4260

CGGCCAACGC GCGGGGAGAG GCGGTTTGCG TATTGGGCGC TCTTCCGCTT CCTCGCTCAC    4320

TGACTCGCTG CGCTCGGTCG TTCGGCTGCG GCGAGCGGTA TCAGCTCACT CAAAGGCGGT    4380

AATACGGTTA TCCACAGAAT CAGGGGATAA CGCAGGAAAG AACATGTGAG CAAAAGGCCA    4440

GCAAAAGGCC AGGAACCGTA AAAAGGCCGC GTTGCTGGCG TTTTTCCATA GGCTCCGCCC    4500

CCCTGACGAG CATCACAAAA ATCGACGCTC AAGTCAGAGG TGGCGAAACC CGACAGGACT    4560

ATAAAGATAC CAGGCGTTTC CCCCTGGAAG CTCCCTCGTG CGCTCTCCTG TTCCGACCCT    4620

GCCGCTTACC GGATACCTGT CCGCCTTTCT CCCTTCGGGA AGCGTGGCGC TTTCTCAATG    4680

CTCACGCTGT AGGTATCTCA GTTCGGTGTA GGTCGTTCGC TCCAAGCTGG GCTGTGTGCA    4740

CGAACCCCCC GTTCAGCCCG ACCGCTGCGC CTTATCCGGT AACTATCGTC TTGAGTCCAA    4800

CCCGGTAAGA CACGACTTAT CGCCACTGGC AGCAGCCACT GGTAACAGGA TTAGCAGAGC    4860

GAGGTATGTA GGCGGTGCTA CAGAGTTCTT GAAGTGGTGG CCTAACTACG GCTACACTAG    4920

AAGGACAGTA TTTGGTATCT GCGCTCTGCT GAAGCCAGTT ACCTTCGGAA AAAGAGTTGG    4980

TAGCTCTTGA TCCGGCAAAC AAACCACCGC TGGTAGCGGT GGTTTTTTTG TTTGCAAGCA    5040

GCAGATTACG CGCAGAAAAA AAGGATCTCA AGAAGATCCT TTGATCTTTT CTACGGGGTC    5100

TGACGCTCAG TGGAACGAAA ACTCACGTTA AGGGATTTTG GTCATGAGAT TATCAAAAAG    5160

GATCTTCACC TAGATCCTTT TAAATTAAAA ATGAAGTTTT AAATCAATCT AAAGTATATA    5220

TGAGTAAACT TGGTCTGACA GTTACCAATG CTTAATCAGT GAGGCACCTA TCTCAGCGAT    5280

CTGTCTATTT CGTTCATCCA TAGTTGCCTG ACTCCCCGTC GTGTAGATAA CTACGATACG    5340

GGAGGGCTTA CCATCTGGCC CCAGTGCTGC AATGATACCG CGAGACCCAC GCTCACCGGC    5400

TCCAGATTTA TCAGCAATAA ACCAGCCAGC CGGAAGGGCC GAGCGCAGAA GTGGTCCTGC    5460

AACTTTATCC GCCTCCATCC AGTCTATTAA TTGTTGCCGG GAAGCTAGAG TAAGTAGTTC    5520

GCCAGTTAAT AGTTTGCGCA ACGTTGTTGC CATTGCTACA GGCATCGTGG TGTCACGCTC    5580

GTCGTTTGGT ATGGCTTCAT TCAGCTCCGG TTCCCAACGA TCAAGGCGAG TTACATGATC    5640

CCCCATGTTG TGCAAAAAAG CGGTTAGCTC CTTCGGTCCT CCGATCGTTG TCAGAAGTAA    5700

GTTGGCCGCA GTGTTATCAC TCATGGTTAT GGCAGCACTG CATAATTCTC TTACTGTCAT    5760

GCCATCCGTA AGATGCTTTT CTGTGACTGG TGAGTACTCA ACCAAGTCAT TCTGAGAATA    5820

GTGTATGCGG CGACCGAGTT GCTCTTGCCC GGCGTCAATA CGGGATAATA CCGCGCCACA    5880

TAGCAGAACT TTAAAAGTGC TCATCATTGG AAAACGTTCT TCGGGGCGAA AACTCTCAAG    5940

GATCTTACCG CTGTTGAGAT CCAGTTCGAT GTAACCCACT CGTGCACCCA ACTGATCTTC    6000

AGCATCTTTT ACTTTCACCA GCGTTTCTGG GTGAGCAAAA ACAGGAAGGC AAAATGCCGC    6060

AAAAAAGGGA ATAAGGGCGA CACGGAAATG TTGAATACTC ATACTCTTCC TTTTTCAATA    6120
```

-continued

```
TTATTGAAGC ATTTATCAGG GTTATTGTCT CATGAGCGGA TACATATTTG AATGTATTTA      6180

GAAAAATAAA CAAATAGGGG TTCCGCGCAC ATTTCCCCGA AAAGTGCCAC CTGACGTC        6238
```

(2) INFORMATION FOR SEQ ID NO:6:

(i) SEQUENCE CHARACTERISTICS:
        (A) LENGTH: 3699 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..3699
        (D) OTHER INFORMATION: /note= "pBSGFP"

(xi) SEQUENCE DESCRIPTION: SEQ ID NO:6:

```
GGAAATTGTA AACGTTAATA TTTTGTTAAA ATTCGCGTTA AATTTTTGTT AAATCAGCTC        60

ATTTTTTAAC CAATAGGCCG AAATCGGCAA ATCCCTTAT AAATCAAAAG AATAGACCGA        120

GATAGGGTTG AGTGTTGTTC CAGTTTGGAA CAAGAGTCCA CTATTAAAGA ACGTGGACTC       180

CAACGTCAAA GGGCGAAAAA CCGTCTATCA GGGCGATGGC CCACTACGTG AACCATCACC       240

CTAATCAAGT TTTTTGGGGT CGAGGTGCCG TAAAGCACTA AATCGGAACC CTAAAGGGAG       300

CCCCCGATTT AGAGCTTGAC GGGGAAAGCC GGCGAACGTG GCGAGAAAGG AAGGGAAGAA       360

AGCGAAAGGA GCGGGCGCTA GGGCGCTGGC AAGTGTAGCG GTCACGCTGC GCGTAACCAC       420

CACACCCGCC GCGCTTAATG CGCCGCTACA GGGCGCGTCG CGCCATTCGC CATTCAGGCT       480

GCGCAACTGT TGGGAAGGGC GATCGGTGCG GGCCTCTTCG CTATTACGCC AGCTGGCGAA       540

AGGGGGATGT GCTGCAAGGC GATTAAGTTG GGTAACGCCA GGGTTTTCCC AGTCACGACG       600

TTGTAAAACG ACGGCCAGTG AATTGTAATA CGACTCACTA TAGGGCGAAT TGGGTACCGG       660

GCCCCCCCTC GAGGTCGACG GTATCGATAA GCTTGATGAT CCTTATTTGT ATAGTTCATC       720

CATGCCATGT GTAATCCCAG CAGCTGTTAC AAACTCAAGA AGGACCATGT GGTCTCTCTT       780

TTCGTTGGGA TCTTTCGAAA GGGCAGATTG TGTGGACAGG TAATGGTTGT CTGGTAAAAG       840

GACAGGGCCA TCGCCAATTG GAGTATTTTG TTGATAATGG TCTGCTAGTT GAACGCTTCC       900

ATCTTCAATG TTGTGTCTAA TTTTGAAGTT AACTTTGATT CCATTCTTTT GTTTGTCTGC       960

CATGATGTAT ACATTGTGTG AGTTATAGTT GTATTCCAAT TTGTGTCCAA GAATGTTTCC      1020

ATCTTCTTTA AAATCAATAC CTTTTAACTC GATTCTATTA ACAAGGGTAT CACCTTCAAA      1080

CTTGACTTCA GCACGTGTCT TGTAGTTCCC GTCATCTTTG AAAAATATAG TTCTTTCCTG      1140

TACATAACCT TCGGGCATGG CACTCTTGAA AAAGTCATGC CGTTTCATAT GATCCGGGTA      1200

TCTTGAAAAG CATTGAACAC CATAAGAGAA AGTAGTGACA AGTGTTGGCC ATGGAACAGG      1260

TAGTTTTCCA GTAGTGCAAA TAAATTTAAG GGTAAGTTTT CCGTATGTTG CATCACCTTC      1320

ACCCTCTCCA CTGACAGAAA ATTTGTGCCC ATTAACATCA CCATCTAATT CAACAAGAAT      1380

TGGGACAACT CCAGTGAAGA GTTCTTCTCC TTTGCTAGCC ATTTCTTGCG CGATCGAATT      1440

CCTGCAGCCC GGGGGATCCA CTAGTTCTAG AGCGGCCGCC ACCGCGGTGG AGCTCCAGCT      1500

TTTGTTCCCT TTAGTGAGGG TTAATTCCGA GCTTGGCGTA ATCATGGTCA TAGCTGTTTC      1560

CTGTGTGAAA TTGTTATCCG CTCACAATTC CACACAACAT ACGAGCCGGA AGCATAAAGT      1620

GTAAAGCCTG GGGTGCCTAA TGAGTGAGCT AACTCACATT AATTGCGTTG CGCTCACTGC      1680
```

-continued

```
CCGCTTTCCA GTCGGGAAAC CTGTCGTGCC AGCTGCATTA ATGAATCGGC CAACGCGCGG      1740

GGAGAGGCGG TTTGCGTATT GGGCGCTCTT CCGCTTCCTC GCTCACTGAC TCGCTGCGCT      1800

CGGTCGTTCG GCTGCGGCGA GCGGTATCAG CTCACTCAAA GGCGGTAATA CGGTTATCCA      1860

CAGAATCAGG GGATAACGCA GGAAAGAACA TGTGAGCAAA AGGCCAGCAA AAGGCCAGGA      1920

ACCGTAAAAA GGCCGCGTTG CTGGCGTTTT TCCATAGGCT CCGCCCCCCT GACGAGCATC      1980

ACAAAAATCG ACGCTCAAGT CAGAGGTGGC GAAACCCGAC AGGACTATAA AGATACCAGG      2040

CGTTTCCCCC TGGAAGCTCC CTCGTGCGCT CTCCTGTTCC GACCCTGCCG CTTACCGGAT      2100

ACCTGTCCGC CTTTCTCCCT TCGGGAAGCG TGGCGCTTTC TCATAGCTCA CGCTGTAGGT      2160

ATCTCAGTTC GGTGTAGGTC GTTCGCTCCA AGCTGGGCTG TGTGCACGAA CCCCCCGTTC      2220

AGCCCGACCG CTGCGCCTTA TCCGGTAACT ATCGTCTTGA GTCCAACCCG GTAAGACACG      2280

ACTTATCGCC ACTGGCAGCA GCCACTGGTA ACAGGATTAG CAGAGCGAGG TATGTAGGCG      2340

GTGCTACAGA GTTCTTGAAG TGGTGGCCTA ACTACGGCTA CACTAGAAGG ACAGTATTTG      2400

GTATCTGCGC TCTGCTGAAG CCAGTTACCT TCGGAAAAAG AGTTGGTAGC TCTTGATCCG      2460

GCAAACAAAC CACCGCTGGT AGCGGTGGTT TTTTTGTTTG CAAGCAGCAG ATTACGCGCA      2520

GAAAAAAAGG ATCTCAAGAA GATCCTTTGA TCTTTTCTAC GGGGTCTGAC GCTCAGTGGA      2580

ACGAAAACTC ACGTTAAGGG ATTTTGGTCA TGAGATTATC AAAAAGGATC TTCACCTAGA      2640

TCCTTTTAAA TTAAAAATGA AGTTTTAAAT CAATCTAAAG TATATATGAG TAAACTTGGT      2700

CTGACAGTTA CCAATGCTTA ATCAGTGAGG CACCTATCTC AGCGATCTGT CTATTTCGTT      2760

CATCCATAGT TGCCTGACTC CCCGTCGTGT AGATAACTAC GATACGGGAG GGCTTACCAT      2820

CTGGCCCCAG TGCTGCAATG ATACCGCGAG ACCCACGCTC ACCGGCTCCA GATTTATCAG      2880

CAATAAACCA GCCAGCCGGA AGGGCCGAGC GCAGAAGTGG TCCTGCAACT TTATCCGCCT      2940

CCATCCAGTC TATTAATTGT TGCCGGGAAG CTAGAGTAAG TAGTTCGCCA GTTAATAGTT      3000

TGCGCAACGT TGTTGCCATT GCTACAGGCA TCGTGGTGTC ACGCTCGTCG TTTGGTATGG      3060

CTTCATTCAG CTCCGGTTCC CAACGATCAA GGCGAGTTAC ATGATCCCCC ATGTTGTGCA      3120

AAAAAGCGGT TAGCTCCTTC GGTCCTCCGA TCGTTGTCAG AAGTAAGTTG GCCGCAGTGT      3180

TATCACTCAT GGTTATGGCA GCACTGCATA ATTCTCTTAC TGTCATGCCA TCCGTAAGAT      3240

GCTTTTCTGT GACTGGTGAG TACTCAACCA AGTCATTCTG AGAATAGTGT ATGCGGCGAC      3300

CGAGTTGCTC TTGCCCGGCG TCAATACGGG ATAATACCGC GCCACATAGC AGAACTTTAA      3360

AAGTGCTCAT CATTGGAAAA CGTTCTTCGG GGCGAAAACT CTCAAGGATC TTACCGCTGT      3420

TGAGATCCAG TTCGATGTAA CCCACTCGTG CACCCAACTG ATCTTCAGCA TCTTTTACTT      3480

TCACCAGCGT TTCTGGGTGA GCAAAAACAG GAAGGCAAAA TGCCGCAAAA AAGGGAATAA      3540

GGGCGACACG GAAATGTTGA ATACTCATAC TCTTCCTTTT TCAATATTAT TGAAGCATTT      3600

ATCAGGGTTA TTGTCTCATG AGCGGATACA TATTTGAATG TATTTAGAAA AATAAACAAA      3660

TAGGGGTTCC GCGCACATTT CCCCGAAAAG TGCCACCTG                            3699
```

(2) INFORMATION FOR SEQ ID NO:7:

(i) SEQUENCE CHARACTERISTICS:
        (A) LENGTH: 6361 base pairs
        (B) TYPE: nucleic acid
        (C) STRANDEDNESS: single
        (D) TOPOLOGY: linear (ii) MOLECULE TYPE: DNA (ix) FEATURE:
   (A) NAME/KEY: -
   (B) LOCATION: 1..6361
   (D) OTHER INFORMATION: /note= "pFRED13"

(xi) SEQUENCE DESCRIPTION: SEQ ID NO:7:

| | | | | | |
|---|---|---|---|---|---|
| TTCTCATGTT | TGACAGCTTA | TCATCGATAA | GCTTTAATGC | GGTAGTTTAT | CACAGTTAAA | 60
| TTGCTAACGC | AGTCAGGCAC | CGTGTATGAA | ATCTAACAAT | GCGCTCATCG | TCATCCTCGG | 120
| CACCGTCACC | CTGGATGCTG | TAGGCATAGG | CTTGGTTATG | CCGGTACTGC | CGGGCCTCTT | 180
| GCGGGATATC | CGGATATAGT | TCCTCCTTTC | AGCAAAAAAC | CCCTCAAGAC | CCGTTTAGAG | 240
| GCCCCAAGGG | GTTATGCTAG | TTATTGCTCA | GCGGTGGCAG | CAGCCAACTC | AGCTTCCTTT | 300
| CGGGCTTTGT | TAGCAGCCGG | ATCCTTATTT | GTATAGTTCA | TCCATGCCAT | GTGTAATCCC | 360
| AGCAGCTGTT | ACAAACTCAA | GAAGGACCAT | GTGGTCTCTC | TTTTCGTTGG | GATCTTTCGA | 420
| AAGGGCAGAT | TGTGTGGACA | GGTAATGGTT | GTCTGGTAAA | AGGACAGGGC | CATCGCCAAT | 480
| TGGAGTATTT | TGTTGATAAT | GGTCTGCTAG | TTGAACGCTT | CCATCTTCAA | TGTTGTGTCT | 540
| AATTTTGAAG | TTAACTTTGA | TTCCATTCTT | TTGTTTGTCT | GCCATGATGT | ATACATTGTG | 600
| TGAGTTATAG | TTGTATTCCA | ATTTGTGTCC | AAGAATGTTT | CCATCTTCTT | TAAAATCAAT | 660
| ACCTTTTAAC | TCGATTCTAT | TAACAAGGGT | ATCACCTTCA | AACTTGACTT | CAGCACGTGT | 720
| CTTGTAGTTC | CCGTCATCTT | TGAAAAATAT | AGTTCTTTCC | TGTACATAAC | CTTCGGGCAT | 780
| GGCACTCTTG | AAAAAGTCAT | GCCGTTTCAT | ATGATCCGGG | TATCTTGAAA | AGCATTGAAC | 840
| ACCATAAGAG | AAAGTAGTGA | CAAGTGTTGG | CCATGGAACA | GGTAGTTTTC | CAGTAGTGCA | 900
| AATAAATTTA | AGGGTAAGTT | TTCCGTATGT | TGCATCACCT | TCACCCTCTC | CACTGACAGA | 960
| AAATTTGTGC | CCATTAACAT | CACCATCTAA | TTCAACAAGA | ATTGGGACAA | CTCCAGTGAA | 1020
| GAGTTCTTCT | CCTTTGCTAG | CCATATGTAT | ATCTCCTTCT | TAAAGTTAAA | CAAAATTATT | 1080
| TCTAGAGGGG | AATTGTTATC | CGCTCACAAT | TCCCCTATAG | TGAGTCGTAT | TAATTTCGCG | 1140
| GGATCGAGAT | CTCGATCCTC | TACGCCGGAC | GCATCGTGGC | CGGCATCACC | GGCGCCACAG | 1200
| GTGCGGTTGC | TGGCGCCTAT | ATCGCCGACA | TCACCGATGG | GGAAGATCGG | GCTCGCCACT | 1260
| TCGGGCTCAT | GAGCGCTTGT | TTCGGCGTGG | GTATGGTGGC | AGGCCCCGTG | GCCGGGGGAC | 1320
| TGTTGGGCGC | CATCTCCTTG | CATGCACCAT | TCCTTGCGGC | GGCGGTGCTC | AACGGCCTCA | 1380
| ACCTACTACT | GGGCTGCTTC | CTAATGCAGG | AGTCGCATAA | GGGAGAGCGT | CGAGATCCCG | 1440
| GACACCATCG | AATGGCGCAA | AACCTTTCGC | GGTATGGCAT | GATAGCGCCC | GGAAGAGAGT | 1500
| CAATTCAGGG | TGGTGAATGT | GAAACCAGTA | ACGTTATACG | ATGTCGCAGA | GTATGCCGGT | 1560
| GTCTCTTATC | AGACCGTTTC | CCGCGTGGTG | AACCAGGCCA | GCCACGTTTC | TGCGAAAACG | 1620
| CGGGAAAAAG | TGGAAGCGGC | GATGGCGGAG | CTGAATTACA | TTCCCAACCG | CGTGGCACAA | 1680
| CAACTGGCGG | GCAAACAGTC | GTTGCTGATT | GGCGTTGCCA | CCTCCAGTCT | GGCCCTGCAC | 1740
| GCGCCGTCGC | AAATTGTCGC | GGCGATTAAA | TCTCGCGCCG | ATCAACTGGG | TGCCAGCGTG | 1800
| GTGGTGTCGA | TGGTAGAACG | AAGCGGCGTC | GAAGCCTGTA | AAGCGGCGGT | GCACAATCTT | 1860
| CTCGCGCAAC | GCGTCAGTGG | GCTGATCATT | AACTATCCGC | TGGATGACCA | GGATGCCATT | 1920
| GCTGTGGAAG | CTGCCTGCAC | TAATGTTCCG | GCGTTATTTC | TTGATGTCTC | TGACCAGACA | 1980
| CCCATCAACA | GTATTATTTT | CTCCCATGAA | GACGGTACGC | GACTGGGCGT | GGAGCATCTG | 2040
| GTCGCATTGG | GTCACCAGCA | AATCGCGCTG | TTAGCGGGCC | CATTAAGTTC | TGTCTCGGCG | 2100
| CGTCTGCGTC | TGGCTGGCTG | GCATAAATAT | CTCACTCGCA | ATCAAATTCA | GCCGATAGCG | 2160

```
GAACGGGAAG GCGACTGGAG TGCCATGTCC GGTTTTCAAC AAACCATGCA AATGCTGAAT    2220

GAGGGCATCG TTCCCACTGC GATGCTGGTT GCCAACGATC AGATGGCGCT GGGCGCAATG    2280

CGCGCCATTA CCGAGTCCGG GCTGCGCGTT GGTGCGGATA TCTCGGTAGT GGGATACGAC    2340

GATACCGAAG ACAGCTCATG TTATATCCCG CCGTTAACCA CCATCAAACA GGATTTTCGC    2400

CTGCTGGGGC AAACCAGCGT GGACCGCTTG CTGCAACTCT CTCAGGGCCA GGCGGTGAAG    2460

GGCAATCAGC TGTTGCCCGT CTCACTGGTG AAAAGAAAAA CCACCCTGGC GCCCAATACG    2520

CAAACCGCCT CTCCCCGCGC GTTGGCCGAT TCATTAATGC AGCTGGCACG ACAGGTTTCC    2580

CGACTGGAAA GCGGGCAGTG AGCGCAACGC AATTAATGTA AGTTAGCTCA CTCATTAGGC    2640

ACCGGGATCT CGACCGATGC CCTTGAGAGC CTTCAACCCA GTCAGCTCCT TCCGGTGGGC    2700

GCGGGCATG ACTATCGTCG CCGCACTTAT GACTGTCTTC TTTATCATGC AACTCGTAGG     2760

ACAGGTGCCG GCAGCGCTCT GGGTCATTTT CGGCGAGGAC CGCTTTCGCT GGAGCGCGAC    2820

GATGATCGGC CTGTCGCTTG CGGTATTCGG AATCTTGCAC GCCCTCGCTC AAGCCTTCGT    2880

CACTGGTCCC GCCACCAAAC GTTTCGGCGA GAAGCAGGCC ATTATCGCCG GCATGGCGGC    2940

CGACGCGCTG GGCTACGTCT TGCTGGCGTT CGCGACGCGA GGCTGGATGG CCTTCCCCAT    3000

TATGATTCTT CTCGCTTCCG GCGGCATCGG GATGCCCGCG TTGCAGGCCA TGCTGTCCAG    3060

GCAGGTAGAT GACGACCATC AGGGACAGCT TCAAGGATCG CTCGCGGCTC TTACCAGCCT    3120

AACTTCGATC ACTGGACCGC TGATCGTCAC GGCGATTTAT GCCGCCTCGG CGAGCACATG    3180

GAACGGGTTG GCATGGATTG TAGGCGCCGC CCTATACCTT GTCTGCCTCC CCGCGTTGCG    3240

TCGCGGTGCA TGGAGCCGGG CCACCTCGAC CTGAATGGAA GCCGGCGGCA CCTCGCTAAC    3300

GGATTCACCA CTCCAAGAAT TGGAGCCAAT CAATTCTTGC GGAGAACTGT GAATGCGCAA    3360

ACCAACCCTT GGCAGAACAT ATCCATCGCG TCCGCCATCT CCAGCAGCCG CACGCGGCGC    3420

ATCTCGGGCA GCGTTGGGTC CTGGCCACGG GTGCGCATGA TCGTGCTCCT GTCGTTGAGG    3480

ACCCGGCTAG GCTGGCGGGG TTGCCTTACT GGTTAGCAGA ATGAATCACC GATACGCGAG    3540

CGAACGTGAA GCGACTGCTG CTGCAAAACG TCTGCGACCT GAGCAACAAC ATGAATGGTC    3600

TTCGGTTTCC GTGTTTCGTA AAGTCTGGAA ACGCGGAAGT CAGCGCCCTG CACCATTATG    3660

TTCCGGATCT GCATCGCAGG ATGCTGCTGG CTACCCTGTG GAACACCTAC ATCTGTATTA    3720

ACGAAGCGCT GGCATTGACC CTGAGTGATT TTTCTCTGGT CCCGCCGCAT CCATACCGCC    3780

AGTTGTTTAC CCTCACAACG TTCCAGTAAC CGGGCATGTT CATCATCAGT AACCCGTATC    3840

GTGAGCATCC TCTCTCGTTT CATCGGTATC ATTACCCCCA TGAACAGAAA TCCCCCTTAC    3900

ACGGAGGCAT CAGTGACCAA ACAGGAAAAA ACCGCCCTTA ACATGGCCCG CTTTATCAGA    3960

AGCCAGACAT TAACGCTTCT GGAGAAACTC AACGAGCTGG ACGCGGATGA ACAGGCAGAC    4020

ATCTGTGAAT CGCTTCACGA CCACGCTGAT GAGCTTTACC GCAGCTGCCT CGCGCGTTTC    4080

GGTGATGACG GTGAAAACCT CTGACACATG CAGCTCCCGG AGACGGTCAC AGCTTGTCTG    4140

TAAGCGGATG CCGGGAGCAG ACAAGCCCGT CAGGGCGCGT CAGCGGGTGT TGGCGGGTGT    4200

CGGGGCGCAG CCATGACCCA GTCACGTAGC GATAGCGGAG TGTATACTGG CTTAACTATG    4260

CGGCATCAGA GCAGATTGTA CTGAGAGTGC ACCATATATG CGGTGTGAAA TACCGCACAG    4320

ATGCGTAAGG AGAAAATACC GCATCAGGCG CTCTTCCGCT TCCTCGCTCA CTGACTCGCT    4380

GCGCTCGGTC GTTCGGCTGC GGCGAGCGGT ATCAGCTCAC TCAAAGGCGG TAATACGGTT    4440

ATCCACAGAA TCAGGGGATA ACGCAGGAAA GAACATGTGA GCAAAAGGCC AGCAAAAGGC    4500

CAGGAACCGT AAAAAGGCCG CGTTGCTGGC GTTTTTCCAT AGGCTCCGCC CCCCTGACGA    4560
```

```
GCATCACAAA AATCGACGCT CAAGTCAGAG GTGGCGAAAC CCGACAGGAC TATAAAGATA        4620

CCAGGCGTTT CCCCCTGGAA GCTCCCTCGT GCGCTCTCCT GTTCCGACCC TGCCGCTTAC        4680

CGGATACCTG TCCGCCTTTC TCCCTTCGGG AAGCGTGGCG CTTTCTCATA GCTCACGCTG        4740

TAGGTATCTC AGTTCGGTGT AGGTCGTTCG CTCCAAGCTG GGCTGTGTGC ACGAACCCCC        4800

CGTTCAGCCC GACCGCTGCG CCTTATCCGG TAACTATCGT CTTGAGTCCA ACCCGGTAAG        4860

ACACGACTTA TCGCCACTGG CAGCAGCCAC TGGTAACAGG ATTAGCAGAG CGAGGTATGT        4920

AGGCGGTGCT ACAGAGTTCT TGAAGTGGTG GCCTAACTAC GGCTACACTA GAAGGACAGT        4980

ATTTGGTATC TGCGCTCTGC TGAAGCCAGT TACCTTCGGA AAAAGAGTTG GTAGCTCTTG        5040

ATCCGGCAAA CAAACCACCG CTGGTAGCGG TGGTTTTTTT GTTTGCAAGC AGCAGATTAC        5100

GCGCAGAAAA AAAGGATCTC AAGAAGATCC TTTGATCTTT TCTACGGGGT CTGACGCTCA        5160

GTGGAACGAA AACTCACGTT AAGGGATTTT GGTCATGAGA TTATCAAAAA GGATCTTCAC        5220

CTAGATCCTT TTAAATTAAA AATGAAGTTT TAAATCAATC TAAAGTATAT ATGAGTAAAC        5280

TTGGTCTGAC AGTTACCAAT GCTTAATCAG TGAGGCACCT ATCTCAGCGA TCTGTCTATT        5340

TCGTTCATCC ATAGTTGCCT GACTCCCCGT CGTGTAGATA ACTACGATAC GGGAGGGCTT        5400

ACCATCTGGC CCCAGTGCTG CAATGATACC GCGAGACCCA CGCTCACCGG CTCCAGATTT        5460

ATCAGCAATA AACCAGCCAG CCGGAAGGGC CGAGCGCAGA AGTGGTCCTG CAACTTTATC        5520

CGCCTCCATC CAGTCTATTA ATTGTTGCCG GGAAGCTAGA GTAAGTAGTT CGCCAGTTAA        5580

TAGTTTGCGC AACGTTGTTG CCATTGCTGC AGGCATCGTG GTGTCACGCT CGTCGTTTGG        5640

TATGGCTTCA TTCAGCTCCG GTTCCCAACG ATCAAGGCGA GTTACATGAT CCCCCATGTT        5700

GTGCAAAAAA GCGGTTAGCT CCTTCGGTCC TCCGATCGTT GTCAGAAGTA AGTTGGCCGC        5760

AGTGTTATCA CTCATGGTTA TGGCAGCACT GCATAATTCT CTTACTGTCA TGCCATCCGT        5820

AAGATGCTTT TCTGTGACTG GTGAGTACTC AACCAAGTCA TTCTGAGAAT AGTGTATGCG        5880

GCGACCGAGT TGCTCTTGCC CGGCGTCAAC ACGGGATAAT ACCGCGCCAC ATAGCAGAAC        5940

TTTAAAAGTG CTCATCATTG GAAAACGTTC TTCGGGGCGA AAACTCTCAA GGATCTTACC        6000

GCTGTTGAGA TCCAGTTCGA TGTAACCCAC TCGTGCACCC AACTGATCTT CAGCATCTTT        6060

TACTTTCACC AGCGTTTCTG GGTGAGCAAA AACAGGAAGG CAAAATGCCG CAAAAAAGGG        6120

AATAAGGGCG ACACGGAAAT GTTGAATACT CATACTCTTC CTTTTTCAAT ATTATTGAAG        6180

CATTTATCAG GGTTATTGTC TCATGAGCGG ATACATATTT GAATGTATTT AGAAAAATAA        6240

ACAAATAGGG GTTCCGCGCA CATTTCCCCG AAAAGTGCCA CCTGACGTCT AAGAAACCAT        6300

TATTATCATG ACATTAACCT ATAAAAATAG GCGTATCACG AGGCCCTTTC GTCTTCAAGA        6360

A                                                                      6361
```

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..48
        (D) OTHER INFORMATION: /note= "oligonucleotide #17422"

(xi) SEQUENCE DESCRIPTION: SEQ ID NO:8:

CAATTTGTGT CCCAGAATGT TGCCATCTTC CTTGAAGTCA ATACCTTT                48

(2) INFORMATION FOR SEQ ID NO:9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..47
        (D) OTHER INFORMATION: /note= "oligonucleotide #17423"

(xi) SEQUENCE DESCRIPTION: SEQ ID NO:9:

GTCTTGTAGT TGCCGTCATC TTTGAAGAAG ATGCTCCTTT CCTGTAC                47

(2) INFORMATION FOR SEQ ID NO:10:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..52
        (D) OTHER INFORMATION: /note= "oligonucleotide #17424"

(xi) SEQUENCE DESCRIPTION: SEQ ID NO:10:

CATGGAACAG GCAGTTTGCC AGTAGTGCAG ATGAACTTCA GGGTAAGTTT TC          52

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..40
        (D) OTHER INFORMATION: /note= "oligonucleotide #17425"

(xi) SEQUENCE DESCRIPTION: SEQ ID NO:11:

CTCCACTGAC AGAGAACTTG TGGCCGTTAA CATCACCATC                        40

(2) INFORMATION FOR SEQ ID NO:12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..47
        (D) OTHER INFORMATION: /note= "oligonucleotide #17426"

(xi) SEQUENCE DESCRIPTION: SEQ ID NO:12:

CCATCTTCAA TGTTGTGGCG GGTCTTGAAG TTCACTTTGA TTCCATT                47

(2) INFORMATION FOR SEQ ID NO:13:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..41
        (D) OTHER INFORMATION: /note= "oligonucleotide #17465"

(xi) SEQUENCE DESCRIPTION: SEQ ID NO:13:

CGATAAGCTT GAGGATCCTC AGTTGTACAG TTCATCCATG C                     41

(2) INFORMATION FOR SEQ ID NO:14:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..849
        (D) OTHER INFORMATION: /note= "pBSGFPsg11"

(xi) SEQUENCE DESCRIPTION: SEQ ID NO:14:

ATGACCATGA TTACGCCAAG CTCGGAATTA ACCCTCACTA AAGGGAACAA AAGCTGGAGC     60

TCCACCGCGG TGGCGGCCGC TCTAGAACTA GTGGATCCCC CGGGCTGCAG GAATTCGATC    120

GCGCAAGAAA TGGCTAGCAA AGGAGAAGAA CTCTTCACTG GAGTTGTCCC AATTCTTGTT    180

GAATTAGATG GTGATGTTAA CGGCCACAAG TTCTCTGTCA GTGGAGAGGG TGAAGGTGAT    240

GCAACATACG GAAAACTTAC CCTGAAGTTC ATCTGCACTA CTGGCAAACT GCCTGTTCCA    300

TGGCCAACAC TTGTCACTAC TCTCTCTTAT GGTGTTCAAT GCTTTTCAAG ATACCCGGAT    360

CATATGAAAC GGCATGACTT TTTCAAGAGT GCCATGCCCG AAGGTTATGT ACAGGAAAGG    420

ACCATCTTCT TCAAAGATGA CGGCAACTAC AAGACACGTG CTGAAGTCAA GTTTGAAGGT    480

GATACCCTTG TTAATAGAAT CGAGTTAAAA GGTATTGACT TCAAGGAAGA TGGCAACATT    540

CTGGGACACA AATTGGAATA CAACTATAAC TCACACAATG TATACATCAT GGCAGACAAA    600

CAAAAGAATG GAATCAAAGT GAACTTCAAG ACCCGCCACA ACATTGAAGA TGGAAGCGTT    660

CAACTAGCAG ACCATTATCA ACAAAATACT CCAATTGGCG ATGGCCCTGT CCTTTTACCA    720

GACAACCATT ACCTGTCCAC ACAATCTGCC CTTTCGAAAG ATCCCAACGA AAAGAGAGAC    780

CACATGGTCC TTCTTGAGTT TGTAACAGCT GCTGGGATTA CACATGGCAT GGATGAACTG    840

TACAACTGA                                                          849

(2) INFORMATION FOR SEQ ID NO:15:

(i) SEQUENCE CHARACTERISTICS:
        (A) LENGTH: 720 base pairs
        (B) TYPE: nucleic acid (C) STRANDEDNESS: single
        (D) TOPOLOGY: linear (ii) MOLECULE TYPE: DNA (ix) FEATURE:
        (A) NAME/KEY: -
        (B) LOCATION: 1..720
        (D) OTHER INFORMATION: /note= "SG12"

(xi) SEQUENCE DESCRIPTION: SEQ ID NO:15:

| | | | | | |
|---|---|---|---|---|---|
| ATGGCTAGCA | AAGGAGAAGA | ACTCTTCACT | GGAGTTGTCC | CAATTCTTGT | TGAATTAGAT | 60 |
| GGTGATGTTA | ACGGCCACAA | GTTCTCTGTC | AGTGGAGAGG | GTGAAGGTGA | TGCAACATAC | 120 |
| GGAAAACTTA | CCCTGAAGTT | CATCTGCACT | ACTGGCAAAC | TGCCTGTTCC | ATGGCCAACA | 180 |
| CTTGTCACTA | CTCTCTCTTA | TGGTGTTCAA | TGCTTTTCAA | GATACCCGGA | TCATATGAAA | 240 |
| CGGCATGACT | TTTTCAAGAG | TGCCATGCCC | GAAGGTTATG | TACAGGAAAG | GACCATCTTC | 300 |
| TTCAAAGATG | ACGGCAACTA | CAAGACACGT | GCTGAAGTCA | AGTTTGAAGG | TGATACCCTT | 360 |
| GTTAATAGAA | TCGAGTTAAA | AGGTATTGAT | TTTAAAGAAG | ATGGAAACAT | TCTTGGACAC | 420 |
| AAATTGGAAT | ACAACTATAA | CTCACACAAT | GTATACATCA | TGGCAGACAA | ACAAAAGAAT | 480 |
| GGAATCAAAG | TTAACTTCAA | AATTAGACAC | AACATTGAAG | ATGGAAGCGT | TCAACTAGCA | 540 |
| GACCATTATC | AACAAAATAC | TCCAATTGGC | GATGGCCCTG | TCCTTTTACC | AGACAACCAT | 600 |
| TACCTGTCCA | CACAATCTGC | CCTTTCGAAA | GATCCCAACG | AAAAGAGAGA | CCACATGGTC | 660 |
| CTTCTTGAGT | TTGTAACAGC | TGCTGGGATT | ACACATGGCA | TGGATGAACT | ATACAAATAA | 720 |

(2) INFORMATION FOR SEQ ID NO:16:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..720
        (D) OTHER INFORMATION: /note= "SG11"

(xi) SEQUENCE DESCRIPTION: SEQ ID NO:16:

| | | | | | |
|---|---|---|---|---|---|
| ATGGCTAGCA | AAGGAGAAGA | ACTCTTCACT | GGAGTTGTCC | CAATTCTTGT | TGAATTAGAT | 60 |
| GGTGATGTTA | ACGGCCACAA | GTTCTCTGTC | AGTGGAGAGG | GTGAAGGTGA | TGCAACATAC | 120 |
| GGAAAACTTA | CCCTGAAGTT | CATCTGCACT | ACTGGCAAAC | TGCCTGTTCC | ATGGCCAACA | 180 |
| CTTGTCACTA | CTCTCTCTTA | TGGTGTTCAA | TGCTTTTCAA | GATACCCGGA | TCATATGAAA | 240 |
| CGGCATGACT | TTTTCAAGAG | TGCCATGCCC | GAAGGTTATG | TACAGGAAAG | GACCATCTTC | 300 |
| TTCAAAGATG | ACGGCAACTA | CAAGACACGT | GCTGAAGTCA | AGTTTGAAGG | TGATACCCTT | 360 |
| GTTAATAGAA | TCGAGTTAAA | AGGTATTGAC | TTCAAGGAAG | ATGGCAACAT | TCTGGGACAC | 420 |
| AAATTGGAAT | ACAACTATAA | CTCACACAAT | GTATACATCA | TGGCAGACAA | ACAAAAGAAT | 480 |
| GGAATCAAAG | TGAACTTCAA | GACCCGCCAC | AACATTGAAG | ATGGAAGCGT | TCAACTAGCA | 540 |
| GACCATTATC | AACAAAATAC | TCCAATTGGC | GATGGCCCTG | TCCTTTTACC | AGACAACCAT | 600 |
| TACCTGTCCA | CACAATCTGC | CCTTTCGAAA | GATCCCAACG | AAAAGAGAGA | CCACATGGTC | 660 |
| CTTCTTGAGT | TTGTAACAGC | TGCTGGGATT | ACACATGGCA | TGGATGAACT | GTACAACTGA | 720 |

(2) INFORMATION FOR SEQ ID NO:17:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..720
        (D) OTHER INFORMATION: /note= "SG25"

(xi) SEQUENCE DESCRIPTION: SEQ ID NO:17:

```
ATGGCTAGCA AAGGAGAAGA ACTCTTCACT GGAGTTGTCC CAATTCTTGT TGAATTAGAT      60

GGTGATGTTA ACGGCCACAA GTTCTCTGTC AGTGGAGAGG GTGAAGGTGA TGCAACATAC     120

GGAAAACTTA CCCTGAAGTT CATCTGCACT ACTGGCAAAC TGCCTGTTCC ATGGCCAACA     180

CTAGTCACTA CTCTGTGCTA TGGTGTTCAA TGCTTTTCAA GATACCCGGA TCATATGAAA     240

CGGCATGACT TTTTCAAGAG TGCCATGCCC GAAGGTTATG TACAGGAAAG GACCATCTTC     300

TTCAAAGATG ACGGCAACTA CAAGACACGT GCTGAAGTCA AGTTTGAAGG TGATACCCTT     360

GTTAATAGAA TCGAGTTAAA AGGTATTGAC TTCAAGGAAG ATGGCAACAT TCTGGGACAC     420

AAATTGGAAT ACAACTATAA CTCACACAAT GTATACATCA TGGCAGACAA ACAAAAGAAT     480

GGAATCAAAG TGAACTTCAA GACCCGCCAC AACATTGAAG ATGGAAGCGT TCAACTAGCA     540

GACCATTATC AACAAAATAC TCCAATTGGC GATGGCCCTG TCCTTTTACC AGACAACCAT     600

TACCTGTCCA CACAATCTGC CCTTTCGAAA GATCCCAACG AAAAGAGAGA CCACATGGTC     660

CTTCTTGAGT TTGTAACAGC TGCTGGGATT ACACATGGCA TGGATGAACT GTACAACTGA     720
```

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..40
        (D) OTHER INFORMATION: /note= "oligonucleotide #18217"

(xi) SEQUENCE DESCRIPTION: SEQ ID NO:18:

```
CATTGAACAC CATAGCACAG AGTAGTGACT AGTGTTGGCC                            40
```

(2) INFORMATION FOR SEQ ID NO:19:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..720
        (D) OTHER INFORMATION: /note= "SB42"

(xi) SEQUENCE DESCRIPTION: SEQ ID NO:19:

```
ATGGCTAGCA AAGGAGAAGA ACTCTTCACT GGAGTTGTCC CAATTCTTGT TGAATTAGAT      60

GGTGATGTTA ACGGCCACAA GTTCTCTGTC AGTGGAGAGG GTGAAGGTGA TGCAACATAC     120

GGAAAACTTA CCCTGAAGTT CATCTGCACT ACTGGCAAAC TGCCTGTTCC ATGGCCAACA     180

CTAGTCACTA CTCTCTCTCA TGGTGTTCAA TGCTTTTCAA GATACCCGGA TCATATGAAA     240

CGGCATGACT TTTTCAAGAG TGCCATGCCC GAAGGTTATG TACAGGAAAG GACCATCTTC     300

TTCAAAGATG ACGGCAACTA CAAGACACGT GCTGAAGTCA AGTTTGAAGG TGATACCCTT     360

GTTAATAGAA TCGAGTTAAA AGGTATTGAT TTTAAAGAAG ATGGAAACAT TCTTGGACAC     420

AAATTGGAAT ACAACTATAA CTCACACAAT GTATACATCA TGGCAGACAA ACAAAAGAAT     480

GGAATCAAAG TTAACTTCAA AATTAGACAC AACATTGAAG ATGGAAGCGT TCAACTAGCA     540

GACCATTATC AACAAAATAC TCCAATTGGC GATGGCCCTG TCCTTTTACC AGACAACCAT     600

TACCTGTCCA CACAATCTGC CCTTTCGAAA GATCCCAACG AAAAGAGAGA CCACATGGTC     660

CTTCTTGAGT TTGTAACAGC TGCTGGGATT ACACATGGCA TGGATGAACT ATACAAATAA     720
```

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..40
        (D) OTHER INFORMATION: /note= "oligonucleotide #bio25"

(xi) SEQUENCE DESCRIPTION: SEQ ID NO:20:

```
CATTGAACAC CATGAGAGAG AGTAGTGACT AGTGTTGGCC                            40
```

(2) INFORMATION FOR SEQ ID NO:21:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..720
        (D) OTHER INFORMATION: /note= "SB49"

(xi) SEQUENCE DESCRIPTION: SEQ ID NO:21:

```
ATGGCTAGCA AAGGAGAAGA ACTCTTCACT GGAGTTGTCC CAATTCTTGT TGAATTAGAT      60

GGTGATGTTA ACGGCCACAA GTTCTCTGTC AGTGGAGAGG GTGAAGGTGA TGCAACATAC     120

GGAAAACTTA CCCTGAAGTT CATCTGCACT ACTGGCAAAC TGCCTGTTCC ATGGCCAACA     180

CTAGTCACTA CTTTCTCTCA TGGTGTTCAA TGCTTTTCAA GATACCCGGA TCATATGAAA     240

CGGCATGACT TTTTCAAGAG TGCCATGCCC GAAGGTTATG TACAGGAAAG GACCATCTTC     300

TTCAAAGATG ACGGCAACTA CAAGACACGT GCTGAAGTCA AGTTTGAAGG TGATACCCTT     360

GTTAATAGAA TCGAGTTAAA AGGTATTGAT TTTAAAGAAG ATGGAAACAT TCTTGGACAC     420

AAATTGGAAT ACAACTATAA CTCACACAAT GTATACATCA TGGCAGACAA ACAAAAGAAT     480

GGAATCAAAG CGAACTTCAA GATCCGCCAC AACATTGAAG ATGGAAGCGT TCAACTAGCA     540
```

```
GACCATTATC AACAAAATAC TCCAATTGGC GATGGCCCTG TCCTTTTACC AGACAACCAT      600

TACCTGTCCA CACAATCTGC CCTTTCGAAA GATCCCAACG AAAAGAGAGA CCACATGGTC      660

CTTCTTGAGT TTGTAACAGC TGCTGGGATT ACACATGGCA TGGATGAACT ATACAAATAA      720
```

(2) INFORMATION FOR SEQ ID NO:22:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..44
        (D) OTHER INFORMATION: /note= "oligonucleotide #19059"

(xi) SEQUENCE DESCRIPTION: SEQ ID NO:22:

```
CTTCAATGTT GTGGCGGATC TTGAAGTTCG CTTTGATTCC ATTC                        44
```

(2) INFORMATION FOR SEQ ID NO:23:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..40
        (D) OTHER INFORMATION: /note= "oligonucleotide #bio24"

(xi) SEQUENCE DESCRIPTION: SEQ ID NO:23:

```
CATTGAACAC CATGAGAGAA AGTAGTGACT AGTGTTGGCC                             40
```

(2) INFORMATION FOR SEQ ID NO:24:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..720
        (D) OTHER INFORMATION: /note= "SB50"

(xi) SEQUENCE DESCRIPTION: SEQ ID NO:24:

```
ATGGCTAGCA AAGGAGAAGA ACTCTTCACT GGAGTTGTCC CAATTCTTGT TGAATTAGAT       60

GGTGATGTTA ACGGCCACAA GTTCTCTGTC AGTGGAGAGG GTGAAGGTGA TGCAACATAC      120

GGAAAACTTA CCCTGAAGTT CATCTGCACT ACTGGCAAAC TGCCTGTTCC ATGGCCAACA      180

CTAGTCACTA CTCTCTCTCA TGGTGTTCAA TGCTTTTCAA GATACCCGGA TCATATGAAA      240

CGGCATGACT TTTTCAAGAG TGCCATGCCC GAAGGTTATG TACAGGAAAG GACCATCTTC      300

TTCAAAGATG ACGGCAACTA CAAGACACGT GCTGAAGTCA AGTTTGAAGG TGATACCCTT      360

GTTAATAGAA TCGAGTTAAA AGGTATTGAT TTTAAAGAAG ATGGAAACAT TCTTGGACAC      420
```

```
AAATTGGAAT ACAACTATAA CTCACACAAT GTATACATCA TGGCAGACAA ACAAAAGAAT      480

GGAATCAAAG CGAACTTCAA GATCCGCCAC AACATTGAAG ATGGAAGCGT TCAACTAGCA      540

GACCATTATC AACAAAATAC TCCAATTGGC GATGGCCCTG TCCTTTTACC AGACAACCAT      600

TACCTGTCCA CACAATCTGC CCTTTCGAAA GATCCCAACG AAAAGAGAGA CCACATGGTC      660

CTTCTTGAGT TTGTAACAGC TGCTGGGATT ACACATGGCA TGGATGAACT ATACAAATAA      720

(2) INFORMATION FOR SEQ ID NO:25:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1521
        (D) OTHER INFORMATION: /note= "pCMVgfo11"

(xi) SEQUENCE DESCRIPTION: SEQ ID NO:25:

ATGGCTAGCA AAGGAGAAGA ACTCTTCACT GGAGTTGTCC CAATTCTTGT TGAATTAGAT       60

GGTGATGTTA ACGGCCACAA GTTCTCTGTC AGTGGAGAGG GTGAAGGTGA TGCAACATAC      120

GGAAAACTTA CCCTGAAGTT CATCTGCACT ACTGGCAAAC TGCCTGTTCC ATGGCCAACA      180

CTTGTCACTA CTCTCTCTTA TGGTGTTCAA TGCTTTTCAA GATACCCGGA TCATATGAAA      240

CGGCATGACT TTTTCAAGAG TGCCATGCCC GAAGGTTATG TACAGGAAAG GACCATCTTC      300

TTCAAAGATG ACGGCAACTA CAAGACACGT GCTGAAGTCA AGTTTGAAGG TGATACCCTT      360

GTTAATAGAA TCGAGTTAAA AGGTATTGAC TTCAAGGAAG ATGGCAACAT TCTGGGACAC      420

AAATTGGAAT ACAACTATAA CTCACACAAT GTATACATCA TGGCAGACAA ACAAAAGAAT      480

GGAATCAAAG TGAACTTCAA GACCCGCCAC AACATTGAAG ATGGAAGCGT TCAACTAGCA      540

GACCATTATC AACAAAATAC TCCAATTGGC GATGGCCCTG TCCTTTTACC AGACAACCAT      600

TACCTGTCCA CACAATCTGC CCTTTCGAAA GATCCCAACG AAAAGAGAGA CCACATGGTC      660

CTTCTTGAGT TTGTAACAGC TGCTGGGATT ACACATGGCA TGGATGAACT GTACAACGGT      720

GCTGGTGCTA TCGAACAAGA TGGATTGCAC GCAGGTTCTC CGGCCGCTTG GGTGGAGAGG      780

CTATTCGGCT ATGACTGGGC ACAACAGACA ATCGGCTGCT CTGATGCCGC CGTGTTCCGG      840

CTGTCAGCGC AGGGGCGCCC GGTTCTTTTT GTCAAGACCG ACCTGTCCGG TGCCCTGAAT      900

GAACTGCAGG ACGAGGCAGC GCGGCTATCG TGGCTGGCCA CGACGGGCGT TCCTTGCGCA      960

GCTGTGCTCG ACGTTGTCAC TGAAGCGGGA AGGGACTGGC TGCTATTGGG CGAAGTGCCG     1020

GGGCAGGATC TCCTGTCATC TCACCTTGCT CCTGCCGAGA AAGTATCCAT CATGGCTGAT     1080

GCAATGCGGC GGCTGCATAC GCTTGATCCG GCTACCTGCC CATTCGACCA CCAAGCGAAA     1140

CATCGCATCG AGCGAGCACG TACTCGGATG GAAGCCGGTC TTGTCGATCA GGATGATCTG     1200

GACGAAGAGC ATCAGGGGCT CGCGCCAGCC GAACTGTTCG CCAGGCTCAA GGCGCGCATG     1260

CCCGACGGCG AGGATCTCGT CGTGACCCAT GGCGATGCCT GCTTGCCGAA TATCATGGTG     1320

GAAAATGGCC GCTTTTCTGG ATTCATCGAC TGTGGCCGGC TGGGTGTGGC GGACCGCTAT     1380

CAGGACATAG CGTTGGCTAC CCGTGATATT GCTGAAGAGC TTGGCGGCGA ATGGGCTGAC     1440

CGCTTCCTCG TGCTTTACGG TATCGCCGCT CCCGATTCGC AGCGCATCGC CTTCTATCGC     1500

CTTCTTGACG AGTTCTTCTG A                                              1521
```

(2) INFORMATION FOR SEQ ID NO:26:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

```
Gly Ala Gly Ala
 1
```

(2) INFORMATION FOR SEQ ID NO:27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..32
        (D) OTHER INFORMATION: /note= "primer Bio51"

(xi) SEQUENCE DESCRIPTION: SEQ ID NO:27:

```
CGCGGATCCT TCGAACAAGA TGGATTGCAC GC                                32
```

(2) INFORMATION FOR SEQ ID NO:28:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..34
        (D) OTHER INFORMATION: /note= "primer Bio52"

(xi) SEQUENCE DESCRIPTION: SEQ ID NO:28:

```
CCGGAATTCT CAGAAGAACT CGTCAAGAAG GCGA                              34
```

(2) INFORMATION FOR SEQ ID NO:29:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..46
        (D) OTHER INFORMATION: /note= "primer Bio49"

(xi) SEQUENCE DESCRIPTION: SEQ ID NO:29:

```
GGCGCGCAAG AAATGGCTAG CAAAGGAGAA GAACTCTTCA CTGGAG                 46
```

(2) INFORMATION FOR SEQ ID NO:30:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: -
    (B) LOCATION: 1..46
    (D) OTHER INFORMATION: /note= "primer Bio50"

(xi) SEQUENCE DESCRIPTION: SEQ ID NO:30:

```
CCCATCGATA GCACCAGCAC CGTTGTACAG TTCATCCATG CCATGT                 46
```

(2) INFORMATION FOR SEQ ID NO:31:

(i) SEQUENCE CHARACTERISTICS:
       (A) LENGTH: 1521 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: -
       (B) LOCATION: 1..1521
       (D) OTHER INFORMATION: /note= "pPGKgfo25"

(xi) SEQUENCE DESCRIPTION: SEQ ID NO:31:

```
ATGGCTAGCA AAGGAGAAGA ACTCTTCACT GGAGTTGTCC CAATTCTTGT TGAATTAGAT    60

GGTGATGTTA ACGGCCACAA GTTCTCTGTC AGTGGAGAGG GTGAAGGTGA TGCAACATAC   120

GGAAAACTTA CCCTGAAGTT CATCTGCACT ACTGGCAAAC TGCCTGTTCC ATGGCCAACA   180

CTAGTCACTA CTCTGTGCTA TGGTGTTCAA TGCTTTTCAA GATACCCGGA TCATATGAAA   240

CGGCATGACT TTTTCAAGAG TGCCATGCCC GAAGGTTATG TACAGGAAAG GACCATCTTC   300

TTCAAAGATG ACGGCAACTA CAAGACACGT GCTGAAGTCA AGTTTGAAGG TGATACCCTT   360

GTTAATAGAA TCGAGTTAAA AGGTATTGAC TTCAAGGAAG ATGGCAACAT TCTGGGACAC   420

AAATTGGAAT ACAACTATAA CTCACACAAT GTATACATCA TGGCAGACAA ACAAAAGAAT   480

GGAATCAAAG TGAACTTCAA GACCCGCCAC AACATTGAAG ATGGAAGCGT TCAACTAGCA   540

GACCATTATC AACAAAATAC TCCAATTGGC GATGGCCCTG TCCTTTTACC AGACAACCAT   600

TACCTGTCCA CACAATCTGC CCTTTCGAAA GATCCCAACG AAAAGAGAGA CCACATGGTC   660

CTTCTTGAGT TTGTAACAGC TGCTGGGATT ACACATGGCA TGGATGAACT GTACAACGGT   720

GCTGGTGCTA TCGAACAAGA TGGATTGCAC GCAGGTTCTC CGGCCGCTTG GGTGGAGAGG   780

CTATTCGGCT ATGACTGGGC ACAACAGACA ATCGGCTGCT CTGATGCCGC CGTGTTCCGG   840

CTGTCAGCGC AGGGGCGCCC GGTTCTTTTT GTCAAGACCG ACCTGTCCGG TGCCCTGAAT   900

GAACTGCAGG ACGAGGCAGC GCGGCTATCG TGGCTGGCCA CGACGGGCGT TCCTTGCGCA   960

GCTGTGCTCG ACGTTGTCAC TGAAGCGGGA AGGGACTGGC TGCTATTGGG CGAAGTGCCG  1020

GGGCAGGATC TCCTGTCATC TCACCTTGCT CCTGCCGAGA AAGTATCCAT CATGGCTGAT  1080

GCAATGCGGC GGCTGCATAC GCTTGATCCG GCTACCTGCC CATTCGACCA CCAAGCGAAA  1140

CATCGCATCG AGCGAGCACG TACTCGGATG GAAGCCGGTC TTGTCGATCA GGATGATCTG  1200

GACGAAGAGC ATCAGGGGCT CGCGCCAGCC GAACTGTTCG CCAGGCTCAA GGCGCGCATG  1260

CCCGACGGCG AGGATCTCGT CGTGACCCAT GGCGATGCCT GCTTGCCGAA TATCATGGTG  1320
```

```
GAAAATGGCC GCTTTTCTGG ATTCATCGAC TGTGGCCGGC TGGGTGTGGC GGACCGCTAT      1380

CAGGACATAG CGTTGGCTAC CCGTGATATT GCTGAAGAGC TTGGCGGCGA ATGGGCTGAC      1440

CGCTTCCTCG TGCTTTACGG TATCGCCGCT CCCGATTCGC AGCGCATCGC CTTCTATCGC      1500

CTTCTTGACG AGTTCTTCTG A                                                1521

(2) INFORMATION FOR SEQ ID NO:32:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..26
         (D) OTHER INFORMATION: /note= "oligonucleotide #18990"

(xi) SEQUENCE DESCRIPTION: SEQ ID NO:32:

GACCGGGACA CGTATCCAGC CTCCGC                                           26

(2) INFORMATION FOR SEQ ID NO:33:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..28
         (D) OTHER INFORMATION: /note= "oligonucleotide #18991"

(xi) SEQUENCE DESCRIPTION: SEQ ID NO:33:

GGAGGCTGGA TACGTGTCCC GGTCTGCA                                         28

(2) INFORMATION FOR SEQ ID NO:34:

(i) SEQUENCE CHARACTERISTICS:
         (A) LENGTH: 7617 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..7617
         (D) OTHER INFORMATION: /note= "pGen-PGKgfo25RO"

(xi) SEQUENCE DESCRIPTION: SEQ ID NO:34:

TCGAGGTCGA CGGTATCGAT TAGTCCAATT TGTTAAAGAC AGGATATCAG TGGTCCAGGC       60

TCTAGTTTTG ACTCAACAAT ATCACCAGCT GAAGCCTATA GAGTACGAGC CATAGATAAA      120

ATAAAAGATT TTATTTAGTC TCCAGAAAAA GGGGGGAATG AAAGACCCCA CCTGTAGGTT      180

TGGCAAGCTA GCTTAAGTAA CGCCATTTTG CAAGGCATGG AAAATACAT AACTGAGAAT       240

AGAGAAGTTC AGATCAAGGT CAGGAACAGA TGGAACAGCT GAATATGGGC CAAACAGGAT      300

ATCTGTGGTA AGCAGTTCCT GCCCCGGCTC AGGGCCAAGA ACAGATGGAA CAGCTGAATA      360
```

-continued

```
TGGGCCAAAC AGGATATCTG TGGTAAGCAG TTCCTGCCCC GGCTCAGGGC CAAGAACAGA     420

TGGTCCCCAG ATGCGGTCCA GCCCTCAGCA GTTTCTAGAG AACCATCAGA TGTTTCCAGG     480

GTGCCCCAAG GACCTGAAAT GACCCTGTGC CTTATTTGAA CTAACCAATC AGTTCGCTTC     540

TCGCTTCTGT TCGCGCGCTT CTGCTCCCCG AGCTCAATAA AAGAGCCCAC AACCCCTCAC     600

TCGGGGCGCC AGTCCTCCGA TTGACTGAGT CGCCCGGGTA CCCGTGTATC CAATAAACCC     660

TCTTGCAGTT GCATCCGACT TGTGGTCTCG CTGTTCCTTG GGAGGGTCTC CTCTGAGTGA     720

TTGACTACCC GTCAGCGGGG GTCTTTCATT TGGGGGCTCG TCCGGGATCG GGAGACCCCT     780

GCCCAGGGAC CACCGACCCA CCACCGGGAG GTAAGCTGGC CAGCAACTTA TCTGTGTCTG     840

TCCGATTGTC TAGTGTCTAT GACTGATTTT ATGCGCCTGC GTCGGTACTA GTTAGCTAAC     900

TAGCTCTGTA TCTGGCGGAC CCGTGGTGGA ACTGACGAGT TCGGAACACC CGGCCGCAAC     960

CCTGGGAGAC GTCCCAGGGA CTTCGGGGGC CGTTTTTGTG GCCCGACCTG AGTCCAAAAA    1020

TCCCGATCGT TTTGGACTCT TTGGTGCACC CCCCTTAGAG GAGGGATATG TGGTTCTGGT    1080

AGGAGACGAG AACCTAAAAC AGTTCCCGCC TCCGTCTGAA TTTTTGCTTT CGGTTTGGGA    1140

CCGAAGCCGC GCCGCGCGTC TTGTCTGCTG CAGCATCGTT CTGTGTTGTC TCTGTCTGAC    1200

TGTGTTTCTG TATTTGTCTG AGAATATGGG CCAGACTGTT ACCACTCCCT TAAGTTTGAC    1260

CTTAGGTCAC TGGAAAGATG TCGAGCGGAT CGCTCACAAC CAGTCGGTAG ATGTCAAGAA    1320

GAGACGTTGG GTTACCTTCT GCTCTGCAGA ATGGCCAACC TTTAACGTCG GATGGCCGCG    1380

AGACGGCACC TTTAACCGAG ACCTCATCAC CCAGGTTAAG ATCAAGGTCT TTTCACCTGG    1440

CCCGCATGGA CACCCAGACC AGGTCCCCTA CATCGTGACC TGGGAAGCCT TGGCTTTTGA    1500

CCCCCCTCCC TGGGTCAAGC CCTTTGTACA CCCTAAGCCT CCGCCTCCTC TTCCTCCATC    1560

CGCCCCGTCT CTCCCCCTTG AACCTCCTCG TTCGACCCCG CCTCGATCCT CCCTTTATCC    1620

AGCCCTCACT CCTTCTCGAC GGTATACAGA CATGATAAGA TACATTGATG AGTTTGGACA    1680

AACCACAACT AGAATGCAGT GAAAAAAATG CTTTATTTGT GAAATTTGTG ATGCTATTGC    1740

TTTATTTGTA ACCATTATAA GCTGCAATAA ACAAGTTGGG GTGGGCGAAG AACTCCAGCA    1800

TGAGATCCCC GCGCTGGAGG ATCATCCAGC CGGCGAACGT GGCGAGAAAG GAAGGGAAGA    1860

AAGCGAAAGG AGCGGGCGCT AGGGCGCTGG CAAGTGTAGC GGTCACGCTG CGCGTAACCA    1920

CCACACCCGC CGCGCTTAAT GCGCCGCTAC AGGGCGCGTG GGGATACCCC CTAGAGCCCC    1980

AGCTGGTTCT TTCCGCCTCA GAAGCCATAG AGCCCACCGC ATCCCCAGCA TGCCTGCTAT    2040

TGTCTTCCCA ATCCTCCCCC TTGCTGTCCT GCCCCACCCC ACCCCCCAGA ATAGAATGAC    2100

ACCTACTCAG ACAATGCGAT GCAATTTCCT CATTTTATTA GGAAAGGACA GTGGGAGTGG    2160

CACCTTCCAG GGTCAAGGAA GGCACGGGGG AGGGCAAAC AACAGATGGC TGGCAACTAG    2220

AAGGCACAGT CGAGGCTGAT CAGCGAGCTC TAGCATTTAG GTGACACTAT AGAATAGGGC    2280

CCTCTAGATG CATGCTCGAG CGGCCGCCAG TGTGATGGAT ATCTGCAGAA TTCTCAGAAG    2340

AACTCGTCAA GAAGGCGATA GAAGGCGATG CGCTGCGAAT CGGGAGCGGC GATACCGTAA    2400

AGCACGAGGA AGCGGTCAGC CCATTCGCCG CCAAGCTCTT CAGCAATATC ACGGGTAGCC    2460

AACGCTATGT CCTGATAGCG GTCCGCCACA CCCAGCCGGC CACAGTCGAT GAATCCAGAA    2520

AAGCGGCCAT TTTCCACCAT GATATTCGGC AAGCAGGCAT CGCCATGGGT CACGACGAGA    2580

TCCTCGCCGT CGGGCATGCG CGCCTTGAGC CTGGCGAACA GTTCGGCTGG CGCGAGCCCC    2640

TGATGCTCTT CGTCCAGATC ATCCTGATCG ACAAGACCGG CTTCCATCCG AGTACGTGCT    2700

CGCTCGATGC GATGTTTCGC TTGGTGGTCG AATGGGCAGG TAGCCGGATC AAGCGTATGC    2760
```

-continued

```
AGCCGCCGCA TTGCATCAGC CATGATGGAT ACTTTCTCGG CAGGAGCAAG GTGAGATGAC    2820

AGGAGATCCT GCCCCGGCAC TTCGCCCAAT AGCAGCCAGT CCCTTCCCGC TTCAGTGACA    2880

ACGTCGAGCA CAGCTGCGCA AGGAACGCCC GTCGTGGCCA GCCACGATAG CCGCGCTGCC    2940

TCGTCCTGCA GTTCATTCAG GGCACCGGAC AGGTCGGTCT TGACAAAAAG AACCGGGCGC    3000

CCCTGCGCTG ACAGCCGGAA CACGGCGGCA TCAGAGCAGC CGATTGTCTG TTGTGCCCAG    3060

TCATAGCCGA ATAGCCTCTC CACCCAAGCG GCCGGAGAAC CTGCGTGCAA TCCATCTTGT    3120

TCGATAGCAC CAGCACCGTT GTACAGTTCA TCCATGCCAT GTGTAATCCC AGCAGCTGTT    3180

ACAAACTCAA GAAGGACCAT GTGGTCTCTC TTTTCGTTGG GATCTTTCGA AAGGGCAGAT    3240

TGTGTGGACA GGTAATGGTT GTCTGGTAAA AGGACAGGGC CATCGCCAAT TGGAGTATTT    3300

TGTTGATAAT GGTCTGCTAG TTGAACGCTT CCATCTTCAA TGTTGTGGCG GTCTTGAAG     3360

TTCACTTTGA TTCCATTCTT TTGTTTGTCT GCCATGATGT ATACATTGTG TGAGTTATAG    3420

TTGTATTCCA ATTTGTGTCC CAGAATGTTG CCATCTTCCT TGAAGTCAAT ACCTTTTAAC    3480

TCGATTCTAT TAACAAGGGT ATCACCTTCA AACTTGACTT CAGCACGTGT CTTGTAGTTG    3540

CCGTCATCTT TGAAGAAGAT GGTCCTTTCC TGTACATAAC CTTCGGGCAT GGCACTCTTG    3600

AAAAAGTCAT GCCGTTTCAT ATGATCCGGG TATCTTGAAA AGCATTGAAC ACCATAGCAC    3660

AGAGTAGTGA CTAGTGTTGG CCATGGAACA GGCAGTTTGC CAGTAGTGCA GATGAACTTC    3720

AGGGTAAGTT TTCCGTATGT TGCATCACCT TCACCCTCTC CACTGACAGA GAACTTGTGG    3780

CCGTTAACAT CACCATCTAA TTCAACAAGA ATTGGGACAA CTCCAGTGAA GAGTTCTTCT    3840

CCTTTGCTAG CCATTTCTTG CGCGCCCGCG GAGGCTGGAT ACGTGTCCCG GTCTGCAGGT    3900

CGAAAGGCCC GGAGATGAGG AAGAGGAGAA CAGCGCGGCA GACGTGCGCT TTTGAAGCGT    3960

GCAGAATGCC GGGCTCCGGA GGACCTTCGC GCCCGCCCCG CCCCTGAGCC CGCCCCTGAG    4020

CCCGCCCCCG GACCCACCCC TTCCCAGCCT CTGAGCCCAG AAAGCGAAGG AGCCAAGCTG    4080

CTATTGGCCG CTGCCCCAAA GGCCTACCCG CTTCCATTGC TCAGCGGTGC TGTCCATCTG    4140

CACGAGACTA GTGAGACGTG CTACTTCCAT TTGTCACGTC CTGCACGACG CGAGCTGCGG    4200

GGCGGGGGGG AACTTCCTGA CTAGGGGAGG AGTAGAAGGT GGCGCGAAGG GGCCACCAAA    4260

GAAGGGAGCC GGTTGGCGCT ACCGGTGGAT GTGGAATGTG TGCGAGGCCA GAGGCCACTT    4320

GTGTAGCGCC AAGTGCCAGC GGGGCTGCTA AAGCGCATGC TCCAGACTGC CTTGGGAAAA    4380

GCGCCTCCCC TACCCGGTAG AATTCGATAT CAAGCTTATC GATACCGTCG AGATCTCCCG    4440

ATCCGTCGAG GTCGACGGTA TCGATTAGTC CAATTTGTTA AAGACAGGAT ATCAGTGGTC    4500

CAGGCTCTAG TTTTGACTCA ACAATATCAC CAGCTGAAGC CTATAGAGTA CGAGCCATAG    4560

ATAAAATAAA AGATTTTATT TAGTCTCCAG AAAAAGGGGG GAATGAAAGA CCCCACCTGT    4620

AGGTTTGGCA AGCTAGCTTA AGTAACGCCA TTTTGCAAGG CATGGAAAAA TACATAACTG    4680

AGAATAGAGA AGTTCAGATC GGGATCCCAA TTCTTTCGGA CTTTTGAAAG TGATGGTGGT    4740

GGGGGAAGGA TTCGAACCTT CGAAGTCGAT GACGGCAGAT TTAGAGTCTG CTCCCTTTGG    4800

CCGCTCGGGA ACCCCACCAC GGGTAATGCT TTTACTGGCC TGCTCCCTTA TCGGGAAGCG    4860

GGGCGCATCA TATCAAATGA CGCGCCGCTG TAAAGTGTTA CGTTGAGAAA GAATTGGGAT    4920

CCCGATCAAG GTCAGGAACA GATGGAACAG CTAGAGAACC ATCAGATGTT TCCAGGGTGC    4980

CCCAAGGACC TGAAATGACC CTGTGCCTTA TTTGAACTAA CCAATCAGTT CGCTTCTCGC    5040

TTCTGTTCGC GCGCTTCTGC TCCCCGAGCT CAATAAAAGA GCCCACAACC CCTCACTCGG    5100
```

```
GGCGCCAGTC CTCCGATTGA CTGAGTCGCC CGGGTACCCG TGTATCCAAT AAACCCTCTT     5160

GCAGTTGCAT CCGACTTGTG GTCTCGCTGT TCCTTGGGAG GGTCTCCTCT GAGTGATTGA     5220

CTACCCGTCA GCGGGGTCT  TTCACCCAGA GTTTGGAACT TACTGTCTTC TTGGGACCTG     5280

CAGCCCGGGG GATCCACTAG TTCTAGAGCG GCCGCCACCG CGGTGGATTC TGCCTCGCGC     5340

GTTTCGGTGA TGACGGTGAA AACCTCTGAC ACATGCAGCT CCCGGAGACG GTCACAGCTT     5400

GTCTGTAAGC GGATGCCGGG AGCAGACAAG CCCGTCAGGG CGCGTCAGCG GGTGTTGGCG     5460

GGTGTCGGGG CGCAGCCATG ACCCAGTCAC GTAGCGATAG CGGAGTGTAT ACTGGCTTAA     5520

CTATGCGGCA TCAGAGCAGA TTGTACTGAG AGTGCACCAT ATGCGGTGTG AAATACCGCA     5580

CAGATGCGTA AGGAGAAAAT ACCGCATCAG GCGCTCTTCC GCTTCCTCGC TCACTGACTC     5640

GCTGCGCTCG GTCGTTCGGC TGCGGCGAGC GGTATCAGCT CACTCAAAGG CGGTAATACG     5700

GTTATCCACA GAATCAGGGG ATAACGCAGG AAAGAACATG TGAGCAAAAG GCCAGCAAAA     5760

GGCCAGGAAC CGTAAAAAGG CCGCGTTGCT GGCGTTTTTC CATAGGCTCC GCCCCCCTGA     5820

CGAGCATCAC AAAAATCGAC GCTCAAGTCA GAGGTGGCGA AACCCGACAG GACTATAAAG     5880

ATACCAGGCG TTTCCCCCTG GAAGCTCCCT CGTGCGCTCT CCTGTTCCGA CCCTGCCGCT     5940

TACCGGATAC CTGTCCGCCT TTCTCCCTTC GGGAAGCGTG GCGCTTTCTC AATGCTCACG     6000

CTGTAGGTAT CTCAGTTCGG TGTAGGTCGT TCGCTCCAAG CTGGGCTGTG TGCACGAACC     6060

CCCCGTTCAG CCCGACCGCT GCGCCTTATC CGGTAACTAT CGTCTTGAGT CCAACCCGGT     6120

AAGACACGAC TTATCGCCAC TGGCAGCAGC CACTGGTAAC AGGATTAGCA GAGCGAGGTA     6180

TGTAGGCGGT GCTACAGAGT TCTTGAAGTG GTGGCCTAAC TACGGCTACA CTAGAAGGAC     6240

AGTATTTGGT ATCTGCGCTC TGCTGAAGCC AGTTACCTTC GGAAAAAGAG TTGGTAGCTC     6300

TTGATCCGGC AAACAAACCA CCGCTGGTAG CGGTGGTTTT TTTGTTTGCA AGCAGCAGAT     6360

TACGCGCAGA AAAAAAGGAT CTCAAGAAGA TCCTTTGATC TTTTCTACGG GGTCTGACGC     6420

TCAGTGGAAC GAAAACTCAC GTTAAGGGAT TTTGGTCATG AGATTATCAA AAAGGATCTT     6480

CACCTAGATC CTTTTAAATT AAAAATGAAG TTTTAAATCA ATCTAAAGTA TATATGAGTA     6540

AACTTGGTCT GACAGTTACC AATGCTTAAT CAGTGAGGCA CCTATCTCAG CGATCTGTCT     6600

ATTTCGTTCA TCCATAGTTG CCTGACTCCC CGTCGTGTAG ATAACTACGA TACGGGAGGG     6660

CTTACCATCT GGCCCCAGTG CTGCAATGAT ACCGCGAGAC CCACGCTCAC CGGCTCCAGA     6720

TTTATCAGCA ATAAACCAGC CAGCCGGAAG GGCCGAGCGC AGAAGTGGTC CTGCAACTTT     6780

ATCCGCCTCC ATCCAGTCTA TTAATTGTTG CCGGGAAGCT AGAGTAAGTA GTTCGCCAGT     6840

TAATAGTTTG CGCAACGTTG TTGCCATTGC TGCAGGCATC GTGGTGTCAC GCTCGTCGTT     6900

TGGTATGGCT TCATTCAGCT CCGGTTCCCA ACGATCAAGG CGAGTTACAT GATCCCCCAT     6960

GTTGTGCAAA AAAGCGGTTA GCTCCTTCGG TCCTCCGATC GTTGTCAGAA GTAAGTTGGC     7020

CGCAGTGTTA TCACTCATGG TTATGGCAGC ACTGCATAAT TCTCTTACTG TCATGCCATC     7080

CGTAAGATGC TTTTCTGTGA CTGGTGAGTA CTCAACCAAG TCATTCTGAG AATAGTGTAT     7140

GCGGCGACCG AGTTGCTCTT GCCCGGCGTC AACACGGGAT AATACCGCGC CACATAGCAG     7200

AACTTTAAAA GTGCTCATCA TTGGAAAACG TTCTTCGGGG CGAAAACTCT CAAGGATCTT     7260

ACCGCTGTTG AGATCCAGTT CGATGTAACC CACTCGTGCA CCCAACTGAT CTTCAGCATC     7320

TTTTACTTTC ACCAGCGTTT CTGGGTGAGC AAAAACAGGA AGGCAAAATG CCGCAAAAAA     7380

GGGAATAAGG GCGACACGGA AATGTTGAAT ACTCATACTC TTCCTTTTTC AATATTATTG     7440

AAGCATTTAT CAGGGTTATT GTCTCATGAG CGGATACATA TTTGAATGTA TTTAGAAAAA     7500
```

-continued

```
TAAACAAATA GGGGTTCCGC GCACATTTCC CCGAAAAGTG CCACCTGACG TCTAAGAAAC      7560

CATTATTATC ATGACATTAA CCTATAAAAA TAGGCGTATC ACGAGGCCCT TTCGTCT         7617
```

(2) INFORMATION FOR SEQ ID NO:35:

(i) SEQUENCE CHARACTERISTICS:
        (A) LENGTH: 15581 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..15581
        (D) OTHER INFORMATION: /note= "pNLnSG11"

(xi) SEQUENCE DESCRIPTION: SEQ ID NO:35:

```
TGGAAGGGCT AATTTGGTCC CAAAAAGAC AAGAGATCCT TGATCTGTGG ATCTACCACA        60

CACAAGGCTA CTTCCCTGAT TGGCAGAACT ACACACCAGG GCCAGGGATC AGATATCCAC      120

TGACCTTTGG ATGGTGCTTC AAGTTAGTAC CAGTTGAACC AGAGCAAGTA GAAGAGGCCA      180

AATAAGGAGA GAAGAACAGC TTGTTACACC CTATGAGCCA GCATGGGATG GAGGACCCGG      240

AGGGAGAAGT ATTAGTGTGG AAGTTTGACA GCCTCCTAGC ATTTCGTCAC ATGGCCCGAG      300

AGCTGCATCC GGAGTACTAC AAAGACTGCT GACATCGAGC TTTCTACAAG GGACTTTCCG      360

CTGGGGACTT TCCAGGGAGG TGTGGCCTGG GCGGGACTGG GGAGTGGCGA GCCCTCAGAT      420

GCTACATATA AGCAGCTGCT TTTTGCCTGT ACTGGGTCTC TCTGGTTAGA CCAGATCTGA      480

GCCTGGGAGC TCTCTGGCTA ACTAGGGAAC CCACTGCTTA AGCCTCAATA AAGCTTGCCT      540

TGAGTGCTCA AGTAGTGTG TGCCCGTCTG TTGTGTGACT CTGGTAACTA GAGATCCCTC      600

AGACCCTTTT AGTCAGTGTG GAAAATCTCT AGCAGTGGCG CCCGAACAGG GACTTGAAAG      660

CGAAAGTAAA GCCAGAGGAG ATCTCTCGAC GCAGGACTCG GCTTGCTGAA GCGCGCACGG      720

CAAGAGGCGA GGGGCGGCGA CTGGTGAGTA CGCCAAAAAT TTTGACTAGC GGAGGCTAGA      780

AGGAGAGAGA TGGGTGCGAG AGCGTCGGTA TTAAGCGGGG GAGAATTAGA TAAATGGGAA      840

AAAATTCGGT TAAGGCCAGG GGGAAAGAAA CAATATAAAC TAAAACATAT AGTATGGGCA      900

AGCAGGGAGC TAGAACGATT CGCAGTTAAT CCTGGCCTTT TAGAGACATC AGAAGGCTGT      960

AGACAAATAC TGGGACAGCT ACAACCATCC CTTCAGACAG GATCAGAAGA ACTTAGATCA     1020

TTATATAATA CAATAGCAGT CCTCTATTGT GTGCATCAAA GGATAGATGT AAAAGACACC     1080

AAGGAAGCCT TAGATAAGAT AGAGGAAGAG CAAAACAAAA GTAAGAAAAA GGCACAGCAA     1140

GCAGCAGCTG ACACAGGAAA CAACAGCCAG GTCAGCCAAA ATTACCCTAT AGTGCAGAAC     1200

CTCCAGGGGC AAATGGTACA TCAGGCCATA TCACCTAGAA CTTTAAATGC ATGGGTAAAA     1260

GTAGTAGAAG AGAAGGCTTT CAGCCCAGAA GTAATACCCA TGTTTTCAGC ATTATCAGAA     1320

GGAGCCACCC CACAAGATTT AAATACCATG CTAAACACAG TGGGGGGACA TCAAGCAGCC     1380

ATGCAAATGT TAAAAGAGAC CATCAATGAG GAAGCTGCAG AATGGGATAG ATTGCATCCA     1440

GTGCATGCAG GGCCTATTGC ACCAGGCCAG ATGAGAGAAC CAAGGGGAAG TGACATAGCA     1500

GGAACTACTA GTACCCTTCA GGAACAAATA GGATGGATGA CACATAATCC ACCTATCCCA     1560

GTAGGAGAAA TCTATAAAAG ATGGATAATC CTGGGATTAA ATAAAATAGT AAGAATGTAT     1620

AGCCCTACCA GCATTCTGGA CATAAGACAA GGACCAAAGG AACCCTTTAG AGACTATGTA     1680
```

```
GACCGATTCT ATAAAACTCT AAGAGCCGAG CAAGCTTCAC AAGAGGTAAA AAATTGGATG    1740

ACAGAAACCT TGTTGGTCCA AAATGCGAAC CCAGATTGTA AGACTATTTT AAAAGCATTG    1800

GGACCAGGAG CGACACTAGA AGAAATGATG ACAGCATGTC AGGGAGTGGG GGACCCGGC    1860

CATAAAGCAA GAGTTTTGGC TGAAGCAATG AGCCAAGTAA CAAATCCAGC TACCATAATG    1920

ATACAGAAAG GCAATTTTAG GAACCAAAGA AAGACTGTTA AGTGTTTCAA TTGTGGCAAA    1980

GAAGGGCACA TAGCCAAAAA TTGCAGGGCC CCTAGGAAAA AGGGCTGTTG GAAATGTGGA    2040

AAGGAAGGAC ACCAAATGAA AGATTGTACT GAGAGACAGG CTAATTTTTT AGGGAAGATC    2100

TGGCCTTCCC ACAAGGGAAG GCCAGGGAAT TTTCTTCAGA GCAGACCAGA GCCAACAGCC    2160

CCACCAGAAG AGAGCTTCAG GTTTGGGGAA GAGACAACAA CTCCCTCTCA GAAGCAGGAG    2220

CCGATAGACA AGGAACTGTA TCCTTTAGCT TCCCTCAGAT CACTCTTTGG CAGCGACCCC    2280

TCGTCACAAT AAAGATAGGG GGGCAATTAA AGGAAGCTCT ATTAGATACA GGAGCAGATG    2340

ATACAGTATT AGAAGAAATG AATTTGCCAG GAAGATGGAA ACCAAAAATG ATAGGGGGAA    2400

TTGGAGGTTT TATCAAAGTA GGACAGTATG ATCAGATACT CATAGAAATC TGCGGACATA    2460

AAGCTATAGG TACAGTATTA GTAGGACCTA CACCTGTCAA CATAATTGGA AGAAATCTGT    2520

TGACTCAGAT TGGCTGCACT TTAAATTTTC CCATTAGTCC TATTGAGACT GTACCAGTAA    2580

AATTAAAGCC AGGAATGGAT GGCCCAAAAG TTAAACAATG GCCATTGACA GAAGAAAAAA    2640

TAAAAGCATT AGTAGAAATT TGTACAGAAA TGGAAAAGGA AGGAAAAATT TCAAAAATTG    2700

GGCCTGAAAA TCCATACAAT ACTCCAGTAT TTGCCATAAA GAAAAAGAC AGTACTAAAT    2760

GGAGAAAATT AGTAGATTTC AGAGAACTTA ATAAGAGAAC TCAAGATTTC TGGGAAGTTC    2820

AATTAGGAAT ACCACATCCT GCAGGGTTAA AACAGAAAAA ATCAGTAACA GTACTGGATG    2880

TGGGCGATGC ATATTTTTCA GTTCCCTTAG ATAAAGACTT CAGGAAGTAT ACTGCATTTA    2940

CCATACCTAG TATAAACAAT GAGACACCAG GGATTAGATA TCAGTACAAT GTGCTTCCAC    3000

AGGGATGGAA AGGATCACCA GCAATATTCC AGTGTAGCAT GACAAAAATC TTAGAGCCTT    3060

TTAGAAAACA AAATCCAGAC ATAGTCATCT ATCAATACAT GGATGATTTG TATGTAGGAT    3120

CTGACTTAGA AATAGGGCAG CATAGAACAA AAATAGAGGA ACTGAGACAA CATCTGTTGA    3180

GGTGGGGATT TACCACACCA GACAAAAAAC ATCAGAAAGA ACCTCCATTC CTTTGGATGG    3240

GTTATGAACT CCATCCTGAT AAATGGACAG TACAGCCTAT AGTGCTGCCA GAAAAGGACA    3300

GCTGGACTGT CAATGACATA CAGAAATTAG TGGGAAAATT GAATTGGGCA AGTCAGATTT    3360

ATGCAGGGAT TAAAGTAAGG CAATTATGTA AACTTCTTAG GGGAACCAAA GCACTAACAG    3420

AAGTAGTACC ACTAACAGAA GAAGCAGAGC TAGAACTGGC AGAAAACAGG GAGATTCTAA    3480

AAGAACCGGT ACATGGAGTG TATTATGACC CATCAAAAGA CTTAATAGCA GAAATACAGA    3540

AGCAGGGGCA AGGCCAATGG ACATATCAAA TTTATCAAGA GCCATTTAAA AATCTGAAAA    3600

CAGGAAAATA TGCAAGAATG AAGGGTGCCC ACACTAATGA TGTGAAACAA TTAACAGAGG    3660

CAGTACAAAA AATAGCCACA GAAAGCATAG TAATATGGGG AAAGACTCCT AAATTTAAAT    3720

TACCCATACA AAAGGAAACA TGGGAAGCAT GGTGGACAGA GTATTGGCAA GCCACCTGGA    3780

TTCCTGAGTG GGAGTTTGTC AATACCCCTC CCTTAGTGAA GTTATGGTAC CAGTTAGAGA    3840

AAGAACCCAT AATAGGAGCA GAAACTTTCT ATGTAGATGG GGCAGCCAAT AGGGAAACTA    3900

AATTAGGAAA AGCAGGATAT GTAACTGACA GAGGAAGACA AAAAGTTGTC CCCTAACGG    3960

ACACAACAAA TCAGAAGACT GAGTTACAAG CAATTCATCT AGCTTTGCAG GATTCGGGAT    4020

TAGAAGTAAA CATAGTGACA GACTCACAAT ATGCATTGGG AATCATTCAA GCACAACCAG    4080
```

```
ATAAGAGTGA ATCAGAGTTA GTCAGTCAAA TAATAGAGCA GTTAATAAAA AAGGAAAAAG     4140

TCTACCTGGC ATGGGTACCA GCACACAAAG GAATTGGAGG AAATGAACAA GTAGATGGGT    4200

TGGTCAGTGC TGGAATCAGG AAAGTACTAT TTTTAGATGG AATAGATAAG GCCCAAGAAG    4260

AACATGAGAA ATATCACAGT AATTGGAGAG CAATGGCTAG TGATTTTAAC CTACCACCTG    4320

TAGTAGCAAA AGAAATAGTA GCCAGCTGTG ATAAATGTCA GCTAAAAGGG GAAGCCATGC    4380

ATGGACAAGT AGACTGTAGC CCAGGAATAT GGCAGCTAGA TTGTACACAT TTAGAAGGAA    4440

AAGTTATCTT GGTAGCAGTT CATGTAGCCA GTGGATATAT AGAAGCAGAA GTAATTCCAG    4500

CAGAGACAGG GCAAGAAACA GCATACTTCC TCTTAAAATT AGCAGGAAGA TGGCCAGTAA    4560

AAACAGTACA TACAGACAAT GGCAGCAATT TCACCAGTAC TACAGTTAAG GCCGCCTGTT    4620

GGTGGGCGGG GATCAAGCAG GAATTTGGCA TTCCCTACAA TCCCCAAAGT CAAGGAGTAA    4680

TAGAATCTAT GAATAAAGAA TTAAAGAAAA TTATAGGACA GGTAAGAGAT CAGGCTGAAC    4740

ATCTTAAGAC AGCAGTACAA ATGGCAGTAT TCATCCACAA TTTTAAAAGA AAAGGGGGGA    4800

TTGGGGGGTA CAGTGCAGGG GAAAGAATAG TAGACATAAT AGCAACAGAC ATACAAACTA    4860

AAGAATTACA AAAACAAATT ACAAAAATTC AAAATTTTCG GGTTTATTAC AGGGACAGCA    4920

GAGATCCAGT TTGGAAAGGA CCAGCAAAGC TCCTCTGGAA AGGTGAAGGG GCAGTAGTAA    4980

TACAAGATAA TAGTGACATA AAAGTAGTGC CAAGAAGAAA AGCAAAGATC ATCAGGGATT    5040

ATGGAAAACA GATGGCAGGT GATGATTGTG TGGCAAGTAG ACAGGATGAG GATTAACACA    5100

TGGAAAAGAT TAGTAAAACA CCATATGTAT ATTTCAAGGA AAGCTAAGGA CTGGTTTTAT    5160

AGACATCACT ATGAAAGTAC TAATCCAAAA ATAAGTTCAG AAGTACACAT CCCACTAGGG    5220

GATGCTAAAT TAGTAATAAC AACATATTGG GGTCTGCATA CAGGAGAAAG AGACTGGCAT    5280

TTGGGTCAGG GAGTCTCCAT AGAATGGAGG AAAAAGAGAT ATAGCACACA AGTAGACCCT    5340

GACCTAGCAG ACCAACTAAT TCATCTGCAC TATTTTGATT GTTTTTCAGA ATCTGCTATA    5400

AGAAATACCA TATTAGGACG TATAGTTAGT CCTAGGTGTG AATATCAAGC AGGACATAAC    5460

AAGGTAGGAT CTCTACAGTA CTTGGCACTA GCAGCATTAA TAAAACCAAA ACAGATAAAG    5520

CCACCTTTGC CTAGTGTTAG GAAACTGACA GAGGACAGAT GGAACAAGCC CCAGAAGACC    5580

AAGGGCCACA GAGGGAGCCA TACAATGAAT GGACACTAGA GCTTTTAGAG GAACTTAAGA    5640

GTGAAGCTGT TAGACATTTT CCTAGGATAT GGCTCCATAA CTTAGGACAA CATATCTATG    5700

AAACTTACGG GGATACTTGG GCAGGAGTGG AAGCCATAAT AAGAATTCTG CAACAACTGC    5760

TGTTTATCCA TTTCAGAATT GGGTGTCGAC ATAGCAGAAT AGGCGTTACT CGACAGAGGA    5820

GAGCAAGAAA TGGAGCCAGT AGATCCTAGA CTAGAGCCCT GGAAGCATCC AGGAAGTCAG    5880

CCTAAAACTG CTTGTACCAA TTGCTATTGT AAAAAGTGTT GCTTTCATTG CCAAGTTTGT    5940

TTCATGACAA AAGCCTTAGG CATCTCCTAT GGCAGGAAGA AGCGGAGACA GCGACGAAGA    6000

GCTCATCAGA ACAGTCAGAC TCATCAAGCT TCTCTATCAA AGCAGTAAGT AGTACATGTA    6060

ATGCAACCTA TAATAGTAGC AATAGTAGCA TTAGTAGTAG CAATAATAAT AGCAATAGTT    6120

GTGTGGTCCA TAGTAATCAT AGAATATAGG AAAATATTAA GACAAAGAAA AATAGACAGG    6180

TTAATTGATA GACTAATAGA AAGAGCAGAA GACAGTGGCA ATGAGAGTGA AGGAGAAGTA    6240

TCAGCACTTG TGGAGATGGG GGTGGAAATG GGGCACCATG CTCCTTGGGA TATTGATGAT    6300

CTGTAGTGCT ACAGAAAAAT TGTGGGTCAC AGTCTATTAT GGGGTACCTG TGTGGAAGGA    6360

AGCAACCACC ACTCTATTTT GTGCATCAGA TGCTAAAGCA TATGATACAG AGGTACATAA    6420
```

-continued

```
TGTTTGGGCC ACACATGCCT GTGTACCCAC AGACCCCAAC CCACAAGAAG TAGTATTGGT      6480

AAATGTGACA GAAAATTTTA ACATGTGGAA AAATGACATG GTAGAACAGA TGCATGAGGA      6540

TATAATCAGT TTATGGGATC AAAGCCTAAA GCCATGTGTA AAATTAACCC CACTCTGTGT      6600

TAGTTTAAAG TGCACTGATT TGAAGAATGA TACTAATACC AATAGTAGTA GCGGGAGAAT      6660

GATAATGGAG AAAGGAGAGA TAAAAAACTG CTCTTTCAAT ATCAGCACAA GCATAAGAGA      6720

TAAGGTGCAG AAAGAATATG CATTCTTTTA TAAACTTGAT ATAGTACCAA TAGATAATAC      6780

CAGCTATAGG TTGATAAGTT GTAACACCTC AGTCATTACA CAGGCCTGTC CAAAGGTATC      6840

CTTTGAGCCA ATTCCCATAC ATTATTGTGC CCCGGCTGGT TTTGCGATTC TAAAATGTAA      6900

TAATAAGACG TTCAATGGAA CAGGACCATG TACAAATGTC AGCACAGTAC AATGTACACA      6960

TGGAATCAGG CCAGTAGTAT CAACTCAACT GCTGTTAAAT GGCAGTCTAG CAGAAGAAGA      7020

TGTAGTAATT AGATCTGCCA ATTTCACAGA CAATGCTAAA ACCATAATAG TACAGCTGAA      7080

CACATCTGTA GAAATTAATT GTACAAGACC CAACAACAAT ACAAGAAAAA GTATCCGTAT      7140

CCAGAGGGGA CCAGGGAGAG CATTTGTTAC AATAGGAAAA ATAGGAAATA TGAGACAAGC      7200

ACATTGTAAC ATTAGTAGAG CAAAATGGAA TGCCACTTTA AAACAGATAG CTAGCAAATT      7260

AAGAGAACAA TTTGGAAATA ATAAAACAAT AATCTTTAAG CAATCCTCAG GAGGGGACCC      7320

AGAAATTGTA ACGCACAGTT TTAATTGTGG AGGGGAATTT TTCTACTGTA ATTCAACACA      7380

ACTGTTTAAT AGTACTTGGT TTAATAGTAC TTGGAGTACT GAAGGGTCAA ATAACACTGA      7440

AGGAAGTGAC ACAATCACAC TCCCATGCAG AATAAAACAA TTTATAAACA TGTGGCAGGA      7500

AGTAGGAAAA GCAATGTATG CCCCTCCCAT CAGTGGACAA ATTAGATGTT CATCAAATAT      7560

TACTGGGCTG CTATTAACAA GAGATGGTGG TAATAACAAC AATGGGTCCG AGATCTTCAG      7620

ACCTGGAGGA GGCGATATGA GGGACAATTG GAGAAGTGAA TTATATAAAT ATAAAGTAGT      7680

AAAAATTGAA CCATTAGGAG TAGCACCCAC CAAGGCAAAG AGAAGAGTGG TGCAGAGAGA      7740

AAAAAGAGCA GTGGGAATAG GAGCTTTGTT CCTTGGGTTC TTGGGAGCAG CAGGAAGCAC      7800

TATGGGCGCA GCGTCAATGA CGCTGACGGT ACAGGCCAGA CAATTATTGT CTGATATAGT      7860

GCAGCAGCAG AACAATTTGC TGAGGGCTAT TGAGGCGCAA CAGCATCTGT TGCAACTCAC      7920

AGTCTGGGGC ATCAAACAGC TCCAGGCAAG AATCCTGGCT GTGGAAAGAT ACCTAAAGGA      7980

TCAACAGCTC CTGGGGATTT GGGGTTGCTC TGGAAAACTC ATTTGCACCA CTGCTGTGCC      8040

TTGGAATGCT AGTTGGAGTA ATAAATCTCT GGAACAGATT TGGAATAACA TGACCTGGAT      8100

GGAGTGGGAC AGAGAAATTA ACAATTACAC AAGCTTAATA CACTCCTTAA TTGAAGAATC      8160

GCAAAACCAG CAAGAAAAGA ATGAACAAGA ATTATTGGAA TTAGATAAAT GGGCAAGTTT      8220

GTGGAATTGG TTTAACATAA CAAATTGGCT GTGGTATATA AAATTATTCA TAATGATAGT      8280

AGGAGGCTTG GTAGGTTTAA GAATAGTTTT TGCTGTACTT TCTATAGTGA ATAGAGTTAG      8340

GCAGGGATAT TCACCATTAT CGTTTCAGAC CCACCTCCCA ATCCCGAGGG GACCCGACAG      8400

GCCCGAAGGA ATAGAAGAAG AAGGTGGAGA GAGAGACAGA GACAGATCCA TTCGATTAGT      8460

GAACGGATCC TTAGCACTTA TCTGGGACGA TCTGCGGAGC CTGTGCCTCT TCAGCTACCA      8520

CCGCTTGAGA GACTTACTCT TGATTGTAAC GAGGATTGTG GAACTTCTGG GACGCAGGGG      8580

GTGGGAAGCC CTCAAATATT GGTGGAATCT CCTACAGTAT TGGAGTCAGG AACTAAAGAA      8640

TAGTGCTGTT AACTTGCTCA ATGCCACAGC CATAGCAGTA GCTGAGGGGA CAGATAGGGT      8700

TATAGAAGTA TTACAAGCAG CTTATAGAGC TATTCGCCAC ATACCTAGAA GAATAAGACA      8760

GGGCTTGGAA AGGATTTTGC TATAAGATGG GTGGCAAGTG GTCAAAAAGT AGTGTGATTG      8820
```

```
GATGGCCTGC TGTAAGGGAA AGAATGAGAC GAGCTGAGCA AGAAATGGCT AGCAAAGGAG    8880

AAGAACTCTT CACTGGAGTT GTCCCAATTC TTGTTGAATT AGATGGTGAT GTTAACGGCC    8940

ACAAGTTCTC TGTCAGTGGA GAGGGTGAAG GTGATGCAAC ATACGGAAAA CTTACCCTGA    9000

AGTTCATCTG CACTACTGGC AAACTGCCTG TTCCATGGCC AACACTTGTC ACTACTCTCT    9060

CTTATGGTGT TCAATGCTTT TCAAGATACC CGGATCATAT GAAACGGCAT GACTTTTTCA    9120

AGAGTGCCAT GCCCGAAGGT TATGTACAGG AAAGGACCAT CTTCTTCAAA GATGACGGCA    9180

ACTACAAGAC ACGTGCTGAA GTCAAGTTTG AAGGTGATAC CCTTGTTAAT AGAATCGAGT    9240

TAAAAGGTAT TGACTTCAAG GAAGATGGCA ACATTCTGGG ACACAAATTG GAATACAACT    9300

ATAACTCACA CAATGTATAC ATCATGGCAG ACAAACAAAA GAATGGAATC AAAGTGAACT    9360

TCAAGACCCG CCACAACATT GAAGATGGAA GCGTTCAACT AGCAGACCAT TATCAACAAA    9420

ATACTCCAAT TGGCGATGGC CCTGTCCTTT TACCAGACAA CCATTACCTG TCCACACAAT    9480

CTGCCCTTTC GAAAGATCCC AACGAAAAGA GAGACCACAT GGTCCTTCTT GAGTTTGTAA    9540

CAGCTGCTGG GATTACACAT GGCATGGATG AACTGTACAA CGGACTCGAG ACCTAGAAAA    9600

ACATGGAGCA ATCACAAGTA GCAATACAGC AGCTAACAAT GCTGCTTGTG CCTGGCTAGA    9660

AGCACAAGAG GAGGAAGAGG TGGGTTTTCC AGTCACACCT CAGGTACCTT TAAGACCAAT    9720

GACTTACAAG GCAGCTGTAG ATCTTAGCCA CTTTTTAAAA GAAAAGGGGG GACTGGAAGG    9780

GCTAATTCAC TCCCAAAGAA GACAAGATAT CCTTGATCTG TGGATCTACC ACACACAAGG    9840

CTACTTCCCT GATTGGCAGA ACTACACACC AGGGCCAGGG GTCAGATATC CACTGACCTT    9900

TGGATGGTGC TACAAGCTAG TACCAGTTGA GCCAGATAAG GTAGAAGAGG CCAATAAAGG    9960

AGAGAACACC AGCTTGTTAC ACCCTGTGAG CCTGCATGGA ATGGATGACC CTGAGAGAGA   10020

AGTGTTAGAG TGGAGGTTTG ACAGCCGCCT AGCATTTCAT CACGTGGCCC GAGAGCTGCA   10080

TCCGGAGTAC TTCAAGAACT GCTGACATCG AGCTTGCTAC AAGGGACTTT CCGCTGGGGA   10140

CTTTCCAGGG AGGCGTGGCC TGGGCGGGAC TGGGGAGTGG CGAGCCCTCA GATGCTGCAT   10200

ATAAGCAGCT GCTTTTTGCC TGTACTGGGT CTCTCTGGTT AGACCAGATC TGAGCCTGGG   10260

AGCTCTCTGG CTAACTAGGG AACCCACTGC TTAAGCCTCA ATAAAGCTTG CCTTGAGTGC   10320

TTCAAGTAGT GTGTGCCCGT CTGTTGTGTG ACTCTGGTAA CTAGAGATCC CTCAGACCCT   10380

TTTAGTCAGT GTGGAAAATC TCTAGCACCC CCCAGGAGGT AGAGGTTGCA GTGAGCCAAG   10440

ATCGCGCCAC TGCATTCCAG CCTGGGCAAG AAAACAAGAC TGTCTAAAAT AATAATAATA   10500

AGTTAAGGGT ATTAAATATA TTTATACATG GAGGTCATAA AAATATATAT ATTTGGGCTG   10560

GGCGCAGTGG CTCACACCTG CGCCCGGCCC TTTGGGAGGC CGAGGCAGGT GGATCACCTG   10620

AGTTTGGGAG TTCCAGACCA GCCTGACCAA CATGGAGAAA CCCCTTCTCT GTGTATTTTT   10680

AGTAGATTTT ATTTTATGTG TATTTTATTC ACAGGTATTT CTGGAAAACT GAAACTGTTT   10740

TTCCTCTACT CTGATACCAC AAGAATCATC AGCACAGAGG AAGACTTCTG TGATCAAATG   10800

TGGTGGGAGA GGGAGGTTTT CACCAGCACA TGAGCAGTCA GTTCTGCCGC AGACTCGGCG   10860

GGTGTCCTTC GGTTCAGTTC CAACACCGCC TGCCTGGAGA GAGGTCAGAC CACAGGGTGA   10920

GGGCTCAGTC CCCAAGACAT AAACACCCAA GACATAAACA CCCAACAGGT CCACCCCGCC   10980

TGCTGCCCAG GCAGAGCCGA TTCACCAAGA CGGGAATTAG GATAGAGAAA GAGTAAGTCA   11040

CACAGAGCCG GCTGTGCGGG AGAACGGAGT TCTATTATGA CTCAAATCAG TCTCCCCAAG   11100

CATTCGGGGA TCAGAGTTTT TAAGGATAAC TTAGTGTGTA GGGGGCCAGT GAGTTGGAGA   11160
```

```
TGAAAGCGTA GGGAGTCGAA GGTGTCCTTT TGCGCCGAGT CAGTTCCTGG GTGGGGCCA      11220

CAAGATCGGA TGAGCCAGTT TATCAATCCG GGGGTGCCAG CTGATCCATG GAGTGCAGGG     11280

TCTGCAAAAT ATCTCAAGCA CTGATTGATC TTAGGTTTTA CAATAGTGAT GTTACCCCAG     11340

GAACAATTTG GGGAAGGTCA GAATCTTGTA GCCTGTAGCT GCATGACTCC TAAACCATAA     11400

TTTCTTTTTT GTTTTTTTTT TTTTATTTTT GAGACAGGGT CTCACTCTGT CACCTAGGCT     11460

GGAGTGCAGT GGTGCAATCA CAGCTCACTG CAGCCTCAAC GTCGTAAGCT CAAGCGATCC     11520

TCCCACCTCA GCCTGCCTGG TAGCTGAGAC TACAAGCGAC GCCCCAGTTA ATTTTTGTAT     11580

TTTTGGTAGA GGCAGCGTTT TGCCGTGTGG CCCTGGCTGG TCTCGAACTC CTGGGCTCAA     11640

GTGATCCAGC CTCAGCCTCC CAAAGTGCTG GGACAACCGG GGCCAGTCAC TGCACCTGGC     11700

CCTAAACCAT AATTTCTAAT CTTTTGGCTA ATTTGTTAGT CCTACAAAGG CAGTCTAGTC     11760

CCCAGGCAAA AAGGGGGTTT GTTTCGGGAA AGGGCTGTTA CTGTCTTTGT TTCAAACTAT     11820

AAACTAAGTT CCTCCTAAAC TTAGTTCGGC CTACACCCAG GAATGAACAA GGAGAGCTTG     11880

GAGGTTAGAA GCACGATGGA ATTGGTTAGG TCAGATCTCT TTCACTGTCT GAGTTATAAT     11940

TTTGCAATGG TGGTTCAAAG ACTGCCCGCT TCTGACACCA GTCGCTGCAT TAATGAATCG     12000

GCCAACGCGC GGGGAGAGGC GGTTTGCGTA TTGGCGCTCT TCCGCTTCCT CGCTCACTGA     12060

CTCGCTGCGC TCGGTCGTTC GGCTGCGGCG AGCGGTATCA GCTCACTCAA AGGCGGTAAT     12120

ACGGTTATCC ACAGAATCAG GGGATAACGC AGGAAAGAAC ATGTGAGCAA AAGGCCAGCA     12180

AAAGGCCAGG AACCGTAAAA AGGCCGCGTT GCTGGCGTTT TTCCATAGGC TCCGCCCCCC     12240

TGACGAGCAT CACAAAAATC GACGCTCAAG TCAGAGGTGG CGAAACCCGA CAGGACTATA     12300

AAGATACCAG GCGTTTCCCC CTGGAAGCTC CCTCGTGCGC TCTCCTGTTC CGACCCTGCC     12360

GCTTACCGGA TACCTGTCCG CCTTTCTCCC TTCGGGAAGC GTGGCGCTTT CTCAATGCTC     12420

ACGCTGTAGG TATCTCAGTT CGGTGTAGGT CGTTCGCTCC AAGCTGGGCT GTGTGCACGA     12480

ACCCCCCGTT CAGCCCGACC GCTGCGCCTT ATCCGGTAAC TATCGTCTTG AGTCCAACCC     12540

GGTAAGACAC GACTTATCGC CACTGGCAGC AGCCACTGGT AACAGGATTA GCAGAGCGAG     12600

GTATGTAGGC GGTGCTACAG AGTTCTTGAA GTGGTGGCCT AACTACGGCT ACACTAGAAG     12660

GACAGTATTT GGTATCTGCG CTCTGCTGAA GCCAGTTACC TTCGGAAAAA GAGTTGGTAG     12720

CTCTTGATCC GGCAAACAAA CCACCGCTGG TAGCGGTGGT TTTTTTGTTT GCAAGCAGCA     12780

GATTACGCGC AGAAAAAAAG GATCTCAAGA AGATCCTTTG ATCTTTTCTA CGGGGTCTGA     12840

CGCTCAGTGG AACGAAAACT CACGTTAAGG GATTTTGGTC ATGAGATTAT CAAAAAGGAT     12900

CTTCACCTAG ATCCTTTTAA ATTAAAAATG AAGTTTTAAA TCAATCTAAA GTATATATGA     12960

GTAAACTTGG TCTGACAGTT ACCAATGCTT AATCAGTGAG GCACCTATCT CAGCGATCTG     13020

TCTATTTCGT TCATCCATAG TTGCCTGACT CCCCGTCGTG TAGATAACTA CGATACGGGA     13080

GGGCTTACCA TCTGGCCCCA GTGCTGCAAT GATACCGCGA GACCCACGCT CACCGGCTCC     13140

AGATTTATCA GCAATAAACC AGCCAGCCGG AAGGGCCGAG CGCAGAAGTG GTCCTGCAAC     13200

TTTATCCGCC TCCATCCAGT CTATTAATTG TTGCCGGGAA GCTAGAGTAA GTAGTTCGCC     13260

AGTTAATAGT TTGCGCAACG TTGTTGCCAT TGCTACAGGC ATCGTGGTGT CACGCTCGTC     13320

GTTTGGTATG GCTTCATTCA GCTCCGGTTC CCAACGATCA AGGCGAGTTA CATGATCCCC     13380

CATGTTGTGC AAAAAAGCGG TTAGCTCCTT CGGTCCTCCG ATCGTTGTCA GAAGTAAGTT     13440

GGCCGCAGTG TTATCACTCA TGGTTATGGC AGCACTGCAT AATTCTCTTA CTGTCATGCC     13500

ATCCGTAAGA TGCTTTTCTG TGACTGGTGA GTACTCAACC AAGTCATTCT GAGAATAGTG     13560
```

-continued

```
TATGCGGCGA CCGAGTTGCT CTTGCCCGGC GTCAATACGG GATAATACCG CGCCACATAG    13620

CAGAACTTTA AAAGTGCTCA TCATTGGAAA ACGTTCTTCG GGGCGAAAAC TCTCAAGGAT    13680

CTTACCGCTG TTGAGATCCA GTTCGATGTA ACCCACTCGT GCACCCAACT GATCTTCAGC    13740

ATCTTTTACT TTCACCAGCG TTTCTGGGTG AGCAAAAACA GGAAGGCAAA ATGCCGCAAA    13800

AAAGGGAATA AGGGCGACAC GGAAATGTTG AATACTCATA CTCTTCCTTT TTCAATATTA    13860

TTGAAGCATT TATCAGGGTT ATTGTCTCAT GAGCGGATAC ATATTTGAAT GTATTTAGAA    13920

AAATAAACAA ATAGGGGTTC CGCGCACATT TCCCCGAAAA GTGCCACCTG ACGTCTAAGA    13980

AACCATTATT ATCATGACAT TAACCTATAA AAATAGGCGT ATCACGAGGC CCTTTCGTCT    14040

TCAAGAACTG CCTCGCGCGT TTCGGTGATG ACGGTGAAAA CCTCTGACAC ATGCAGCTCC    14100

CGGAGACGGT CACAGCTTGT CTGTAAGCGG ATGCCGGGAG CAGACAAGCC CGTCAGGGCG    14160

CGTCAGCGGG TGTTGGCGGG TGTCGGGGCG CAGCCATGAC CCAGTCACGT AGCGATAGCG    14220

GAGTGTACTG GCTTAACTAT GCGGCATCAG AGCAGATTGT ACTGAGAGTG CACCATATGC    14280

GGTGTGAAAT ACCGCACAGA TGCGTAAGGA GAAAATACCG CATCAGGCGC CATTCGCCAT    14340

TCAGGCTGCG CAACTGTTGG GAAGGGCGAT CGGTGCGGGC CTCTTCGCTA TTACGCCAGC    14400

GCGGGAGGC AGAGATTGCA GTAAGCTGAG ATCCAGCAC TGCACTCCAG CCTGGGCGAC    14460

AGAGTAAGAC TCTGTCTCAA AAATAAAATA AATAAATCAA TCAGATATTC AATCTTTTC    14520

CTTTATTTAT TTATTTATTT CTATTTTGG AAACACAGTC CTTCCTTATT CCAGAATTAC    14580

ACATATATTC TATTTTTCTT TATATGCTCC AGTTTTTTTT AGACCTTCAC CTGAAATGTG    14640

TGTATACAAA ATCTAGGCCA GTCCAGCAGA GCCTAAAGGT AAAAAATAAA ATAATAAAAA    14700

ATAAATAAAA TCTAGCTCAC TCCTTCACAT CAAAATGGAG ATACAGCTGT TAGCATTAAA    14760

TACCAAATAA CCCATCTTGT CCTCAATAAT TTTAAGCGCC TCTCTCCACC ACATCTAACT    14820

CCTGTCAAAG GCATGTGCCC CTTCCGGGCG CTCTGCTGTG CTGCCAACCA ACTGGCATGT    14880

GGACTCTGCA GGGTCCCTAA CTGCCAAGCC CCACAGTGTG CCCTGAGGCT GCCCCTTCCT    14940

TCTAGCGGCT GCCCCCACTC GGCTTTGCTT TCCCTAGTTT CAGTTACTTG CGTTCAGCCA    15000

AGGTCTGAAA CTAGGTGCGC ACAGAGCGGT AAGACTGCGA GAGAAAGAGA CCAGCTTTAC    15060

AGGGGGTTTA TCACAGTGCA CCCTGACAGT CGTCAGCCTC ACAGGGGGTT TATCACATTG    15120

CACCCTGACA GTCGTCAGCC TCACAGGGGG TTTATCACAG TGCACCCTTA CAATCATTCC    15180

ATTTGATTCA CAATTTTTTT AGTCTCTACT GTGCCTAACT TGTAAGTTAA ATTTGATCAG    15240

AGGTGTGTTC CCAGAGGGGA AAACAGTATA TACAGGGTTC AGTACTATCG CATTTCAGGC    15300

CTCCACCTGG GTCTTGGAAT GTGTCCCCCG AGGGGTGATG ACTACCTCAG TTGGATCTCC    15360

ACAGGTCACA GTGACACAAG ATAACCAAGA CACCTCCCAA GGCTACCACA ATGGGCCGCC    15420

CTCCACGTGC ACATGGCCGG AGGAACTGCC ATGTCGGAGG TGCAAGCACA CCTGCGCATC    15480

AGAGTCCTTG GTGTGGAGGG AGGGACCAGC GCAGCTTCCA GCCATCCACC TGATGAACAG    15540

AACCTAGGGA AAGCCCCAGT TCTACTTACA CCAGGAAAGG C                        15581
```

(2) INFORMATION FOR SEQ ID NO:36:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA -continued

```
    (ix) FEATURE:
         (A) NAME/KEY: -
         (B) LOCATION: 1..74
         (D) OTHER INFORMATION: /note= "primer #17982"

(xi) SEQUENCE DESCRIPTION: SEQ ID NO:36:

GGGGCGTACG GAGCGCTCCG AATTCGGTAC CGTTTAAACG GGCCCTCTCG AGTCCGTTGT     60

ACAGTTCATC CATG                                                     74

(2) INFORMATION FOR SEQ ID NO:37:

(i) SEQUENCE CHARACTERISTICS:
         (A) LENGTH: 66 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..66
         (D) OTHER INFORMATION: /note= "primer #17983"

(xi) SEQUENCE DESCRIPTION: SEQ ID NO:37:

GGGGGAATTC GCGCGCGTAC GTAAGCGCTA GCTGAGCAAG AAATGGCTAG CAAAGGAGAA     60

GAACTC                                                              66
```